(12) United States Patent
Merchant et al.

(10) Patent No.: US 12,343,159 B2
(45) Date of Patent: Jul. 1, 2025

(54) SYSTEMS AND METHODS FOR MODELING THE BREAST USING SPHERICAL HARMONICS

(71) Applicant: University of Houston System, Houston, TX (US)

(72) Inventors: Fatima Merchant, Houston, TX (US); Audrey Cheong, Richmond, TX (US)

(73) Assignee: UNIVERSITY OF HOUSTON SYSTEM, Houston, TX (US)

( * ) Notice: Subject to any disclaimer, the term of this patent is extended or adjusted under 35 U.S.C. 154(b) by 879 days.

(21) Appl. No.: 17/605,720

(22) PCT Filed: Apr. 24, 2020

(86) PCT No.: PCT/US2020/029783
§ 371 (c)(1),
(2) Date: Oct. 22, 2021

(87) PCT Pub. No.: WO2020/219856
PCT Pub. Date: Oct. 29, 2020

(65) Prior Publication Data
US 2022/0304619 A1  Sep. 29, 2022

Related U.S. Application Data

(60) Provisional application No. 62/838,997, filed on Apr. 26, 2019.

(51) Int. Cl.
*A61B 5/00* (2006.01)
*A61B 5/107* (2006.01)
(Continued)

(52) U.S. Cl.
CPC .......... *A61B 5/4312* (2013.01); *A61B 5/1079* (2013.01); *A61B 34/10* (2016.02);
(Continued)

(58) Field of Classification Search
CPC ..... A61B 6/502; A61B 5/4312; A61B 8/0825; A61B 5/055; A61B 8/5223; A61B 8/085;
(Continued)

(56) References Cited

U.S. PATENT DOCUMENTS

| | | | |
|---|---|---|---|
| 2013/0267850 A1 | 10/2013 | Berman | |
| 2014/0254910 A1* | 9/2014 | Jerebko | G06T 7/0012 |
| | | | 382/132 |
| 2015/0286785 A1* | 10/2015 | Hielscher | G16H 50/20 |
| | | | 382/131 |

OTHER PUBLICATIONS

International Preliminary Report on Patentability issued by The International Bureau of WIPO in connection with International Application No. PCT/US20/29783, dated Sep. 28, 2021.
(Continued)

*Primary Examiner* — Ajibola A Akinyemi
(74) *Attorney, Agent, or Firm* — George Likourezos; Carter, DeLuca & Farrell LLP

(57) ABSTRACT

A system and a computer implemented method are disclosed to model breast shape using three-dimensional spherical harmonics with adjustable parameters to modulate breast size, projection, and/or ptosis. The method includes receiving a 3D image including a breast, identifying the breast in the 3D image, extracting 3D image data of the breast from the 3D image, forming a closed object using the 3D image data of the breast to create a zero-genus surface, mapping the 3D image data of the breast to a predefined template using spherical coordinates, and determining a 3D spherical harmonic descriptor of the 3D image data of the breast.

20 Claims, 56 Drawing Sheets

(51) Int. Cl.
    *A61B 34/10*          (2016.01)
    *G16H 30/40*        (2018.01)
    *G16H 50/70*        (2018.01)

(52) U.S. Cl.
    CPC .............. *G16H 30/40* (2018.01); *G16H 50/70* (2018.01); *A61B 5/004* (2013.01); *A61B 2034/105* (2016.02)

(58) Field of Classification Search
    CPC . A61B 10/0041; A61B 6/032; A61B 2576/02; A61B 5/015; A61B 5/0091; A61B 6/025; A61B 6/037; A61B 6/5247; A61B 2034/2055; A61B 34/20
    USPC .......................................................... 382/128
    See application file for complete search history.

(56) References Cited

OTHER PUBLICATIONS

International Search Report and Written Opinion issued by the International Searching Authority/US in connection with International Application No. PCT/US20/29783, dated Jul. 23, 2020.

\* cited by examiner

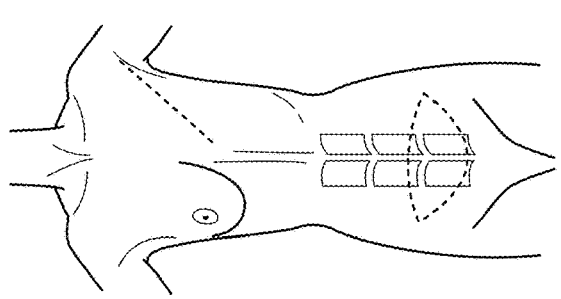
FIG. 1A
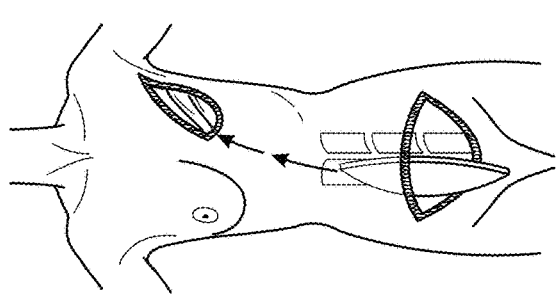
FIG. 1B
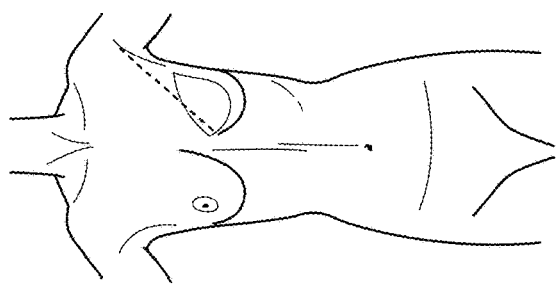
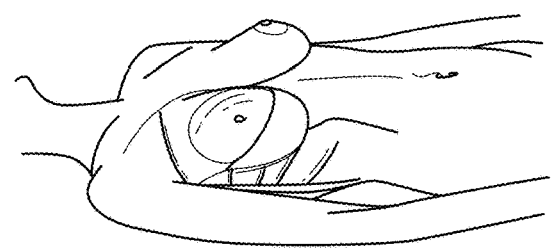
FIG. 2A
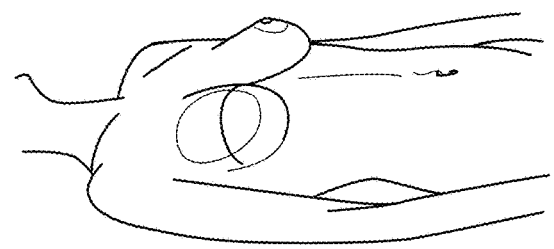
FIG. 2B
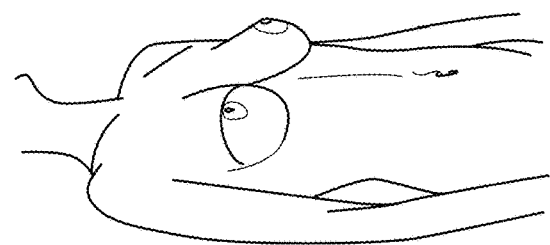
FIG. 2C

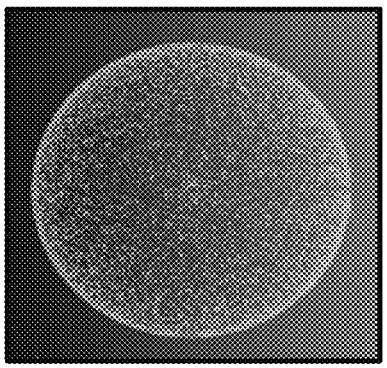
FIG. 5A
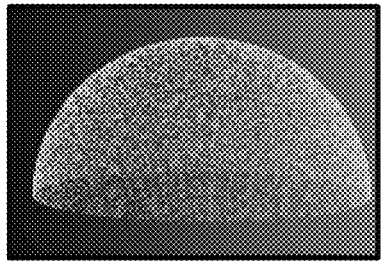
FIG. 5B
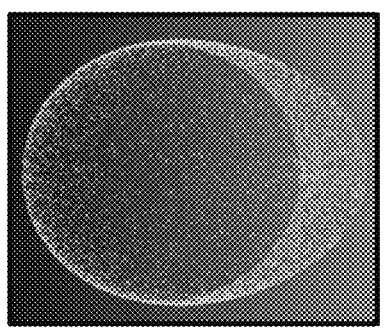
FIG. 5C
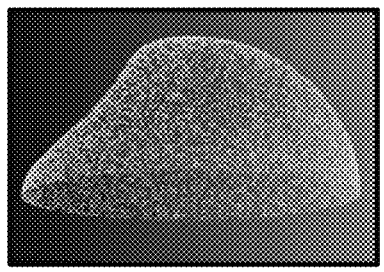
FIG. 5D
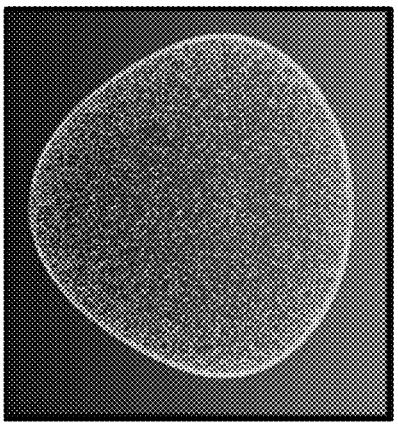
FIG. 5E
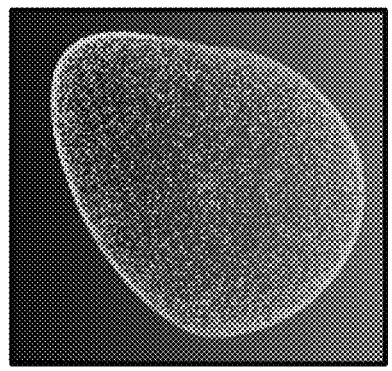
FIG. 5F
FIG. 5G

| VARIABLES | STATISTICS |
|---|---|
| AGE, YEARS | |
| MEAN ± STD | 48.6 ± 10.5 |
| MEDIAN (RANGE) | 47 (RANGE: 28 TO 73) |
| BMI, kg/m² | |
| MEAN ± STD | 26.7 ± 5.1 |
| MEDIAN (RANGE) | 25.6 (RANGE: 18 TO 41) |
| TUMOR SIZE, cm | |
| MEAN ± STD | 2.31 ± 2.04 |
| MEDIAN (RANGE) | 1.55 (RANGE: 0.07 TO 11.00) |
| VARIABLES | NO. (%) |
| RACE | |
| CAUCASIAN | 65 (72.2) |
| AFRICAN AMERICAN | 6 (6.7) |
| ASIAN | 4 (4.4) |
| OTHER | 4 (4.4) |
| NOT AVAILABLE | 4 (8.9) |
| ETHNICITY | |
| HISPANIC | 13 (14.9) |
| NOT HISPANIC | 64 (73.6) |
| NOT AVAILABLE | 10 (11.5) |
| DIAGNOSIS | |
| UNILATERAL BREAST CANCER | 69 (79.3) |
| BILATERAL BREAST CANCER | 3 (3.4) |
| UNKNOWN CANCER SIDE | 1 (1.1) |
| NO CANCER | 14 (16.1) |
| PRE-OPERATIVE CHEMOTHERAPY | |
| YES | 34 (40.2) |
| NO | 53 (62.1) |

FIG. 6A

| VARIABLES | NO. (%) |
|---|---|
| NUMBER OF BREASTS | 76 |
| TUMOR TYPE | |
| DUCTAL CARCINOMA IN SITU (DCIS) | 19 (25) |
| LOBULAR CARCINOMA IN SITU (LCIS) | 1 (1.3) |
| INVASIVE DUCTAL CARCINOMA (IDC) | 50 (65.8) |
| INVASIVE LOBULAR CARCINOMA (ILC) | 4 (5.3) |
| DCIS AND IDC | 2 (2.6) |
| POSITION OF THE TUMOR(S) | |
| LOWER-INNER QUADRANT | 2 (2.6) |
| UPPER-INNER QUADRANT | 11 (14.5) |
| UPPER-OUTER QUADRANT | 19 (25) |
| LOWER-OUTER QUADRANT | 10 (13.2) |
| CENTRAL | 3 (3.9) |
| NIPPLE | 1 (1.3) |
| OVERLAPPING LESION | 15 (19.7) |
| NOS (EXCLUDES SKIN) | 12 (15.8) |
| UNKNOWN | 3 (3.9) |

FIG. 6B

| Variables | TRAM Flap | Implant |
|---|---|---|
| Number of Patients | 18 | 15 |
| Number of Breasts | 29 | 24 |
| Age, yrs | | |
| Mean ± STD | 47.5 ± 10.7 | 49.2 ± 8.0 |
| Median (Range) | 50.5 (Range: 33 to 63) | 48 (Range: 27 to 67) |
| BMI, kg/m² | | |
| Mean ± STD | 29.8 ± 4.2 | 27.0 ± 6.4 |
| Median (Range) | 29.5 (Range: 22.4 to 40.9) | 25.7 (Range: 18.5 to 40) |
| Race | | |
| Caucasian | 14 | 13 |
| African American | 2 | 1 |
| Asian | 1 | 0 |
| Other | 1 | 1 |
| Ethnicity | | |
| Hispanic | 4 | 5 |
| Not Hispanic | 14 | 9 |
| Not Available | 0 | 1 |

FIG. 6C

| Procedure | Number of Breasts |
|---|---|
| TRAM Flap | 24 |
| DIEP Flap | 1 |
| LD Flap | 1 |
| Implant | 21 |
| Revision (To Natural Breast) | 6 |
| Total | 53 |

FIG. 6D

| Variables | Statistics |
|---|---|
| Age, Years | |
| Mean ± STD | 48.0 ± 9.4 |
| Median (Range) | 49 (Range: 24 to 66) |
| BMI, kg/m$^2$ | |
| Mean ± STD | 28.7 ± 5.7 |
| Median (Range) | 27.7 (Range: 18.5 to 40.9) |
| Race | |
| Caucasian | 24 |
| African American | 3 |
| Asian | 1 |
| Other | 1 |
| Ethnicity | |
| Hispanic | 7 |
| Not Hispanic | 21 |
| Not Available | 1 |

FIG. 6E

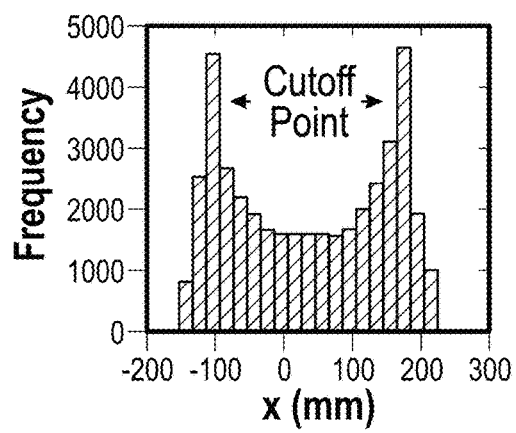
FIG. 7A
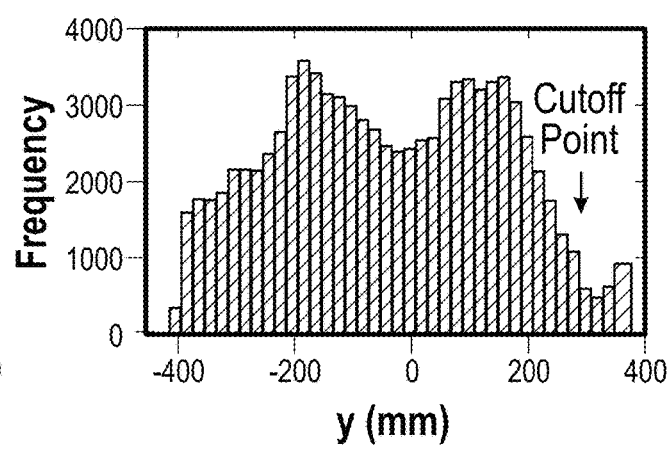
FIG. 7B
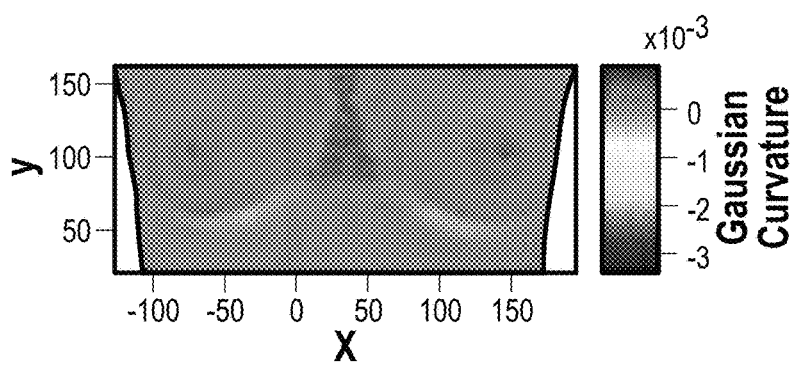
FIG. 7C
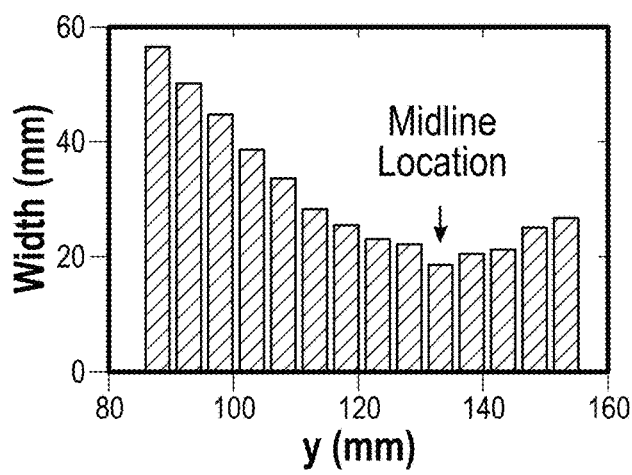
FIG. 7D
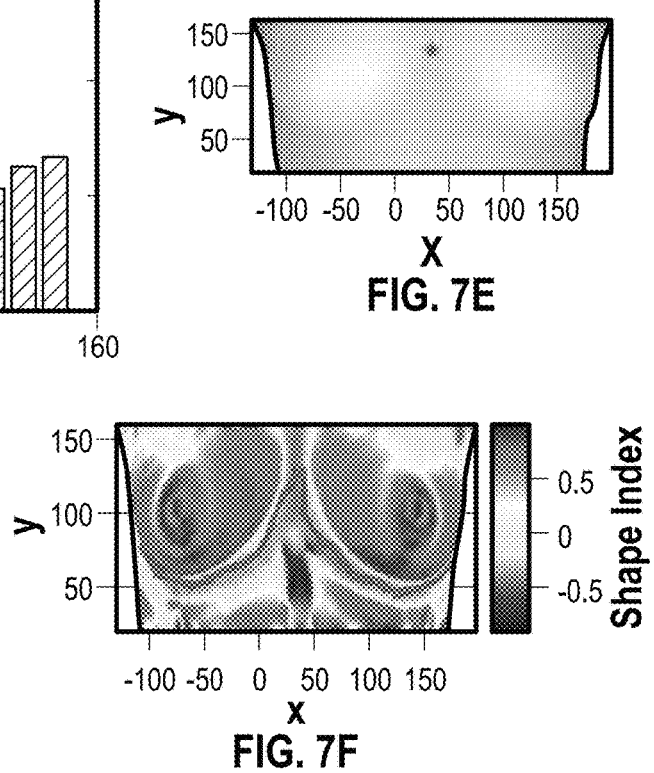
FIG. 7E
FIG. 7F

- Connect T and L: $\dfrac{(X-T_x)^2}{(2(T_x-L_x))^2} + \dfrac{(Y-L_y)^2}{(2(T_y-L_y))^2} = 1$

- Connect M and T: $\dfrac{(X-T_x)^2}{(2(M_x-T_x))^2} + \dfrac{(Y-M_y)^2}{(2(M_y-T_y))^2} = 1$

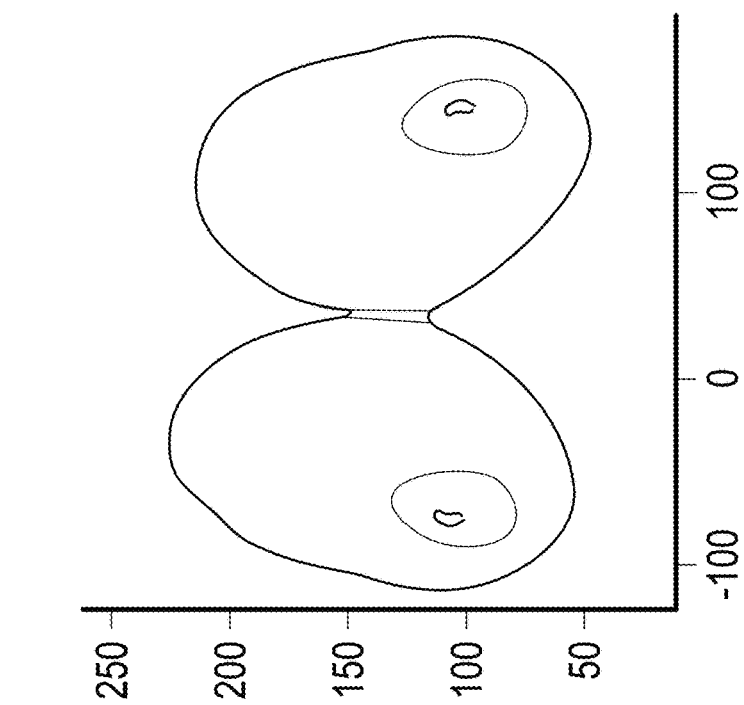
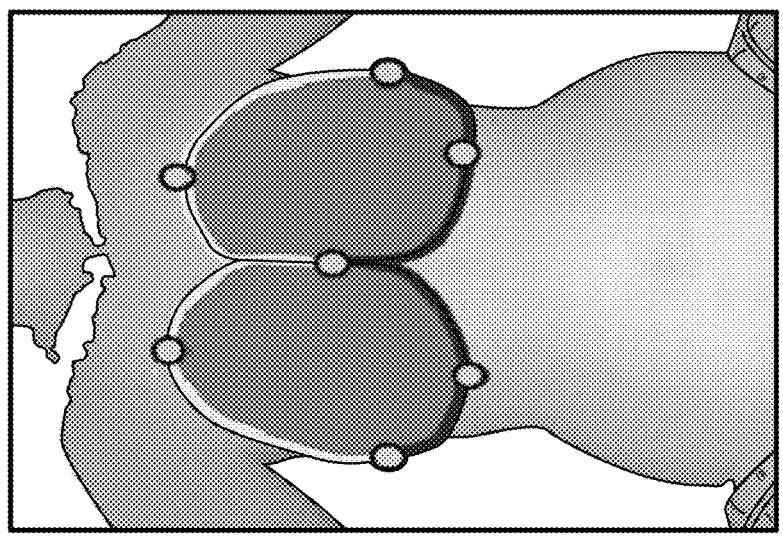
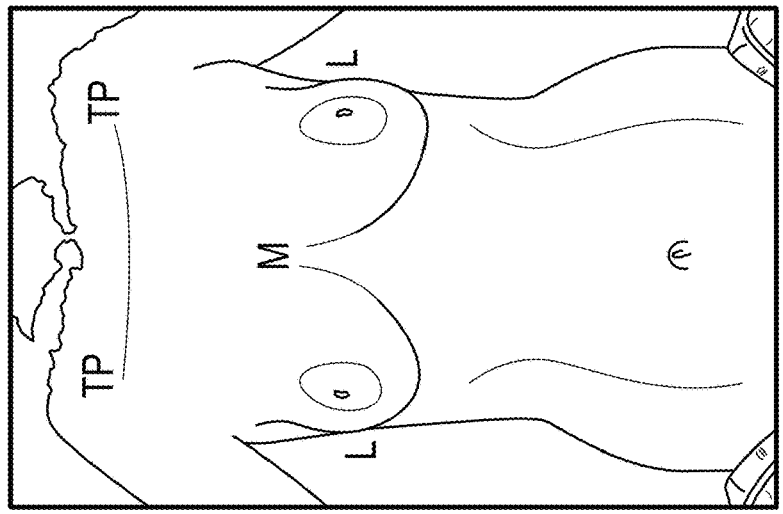
FIG. 9C
FIG. 9B
FIG. 9A

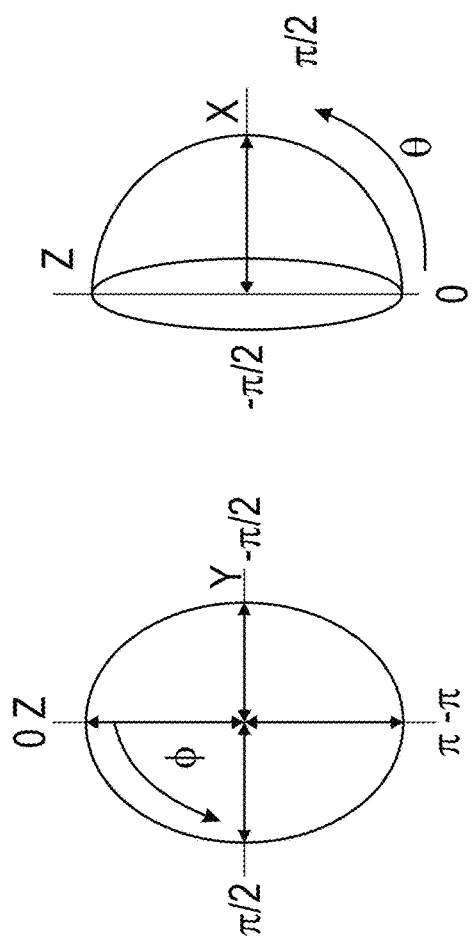
FIG. 11A
FIG. 11B
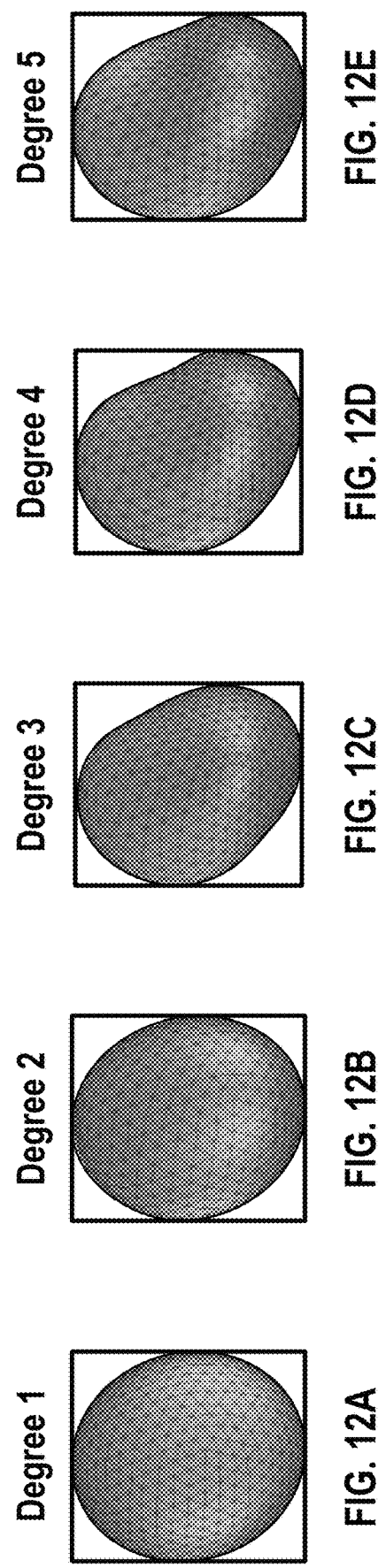
FIG. 12A
FIG. 12B
FIG. 12C
FIG. 12D
FIG. 12E

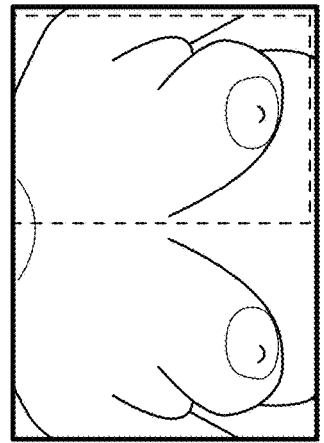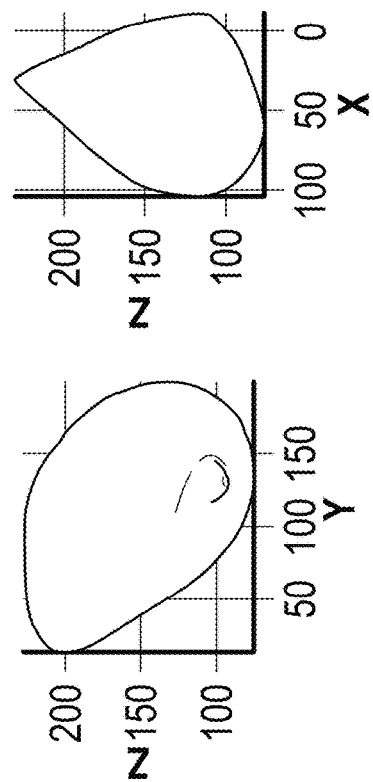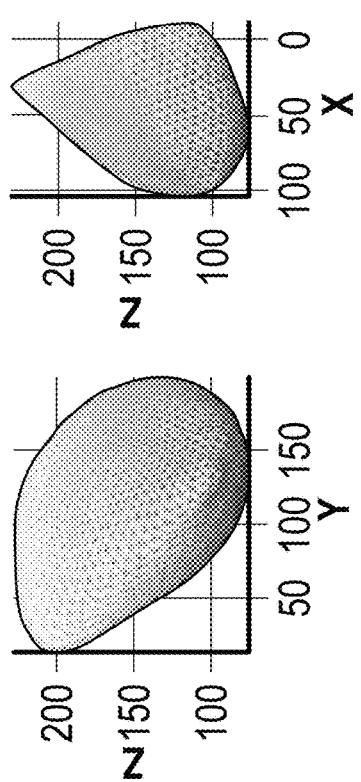
FIG. 16B
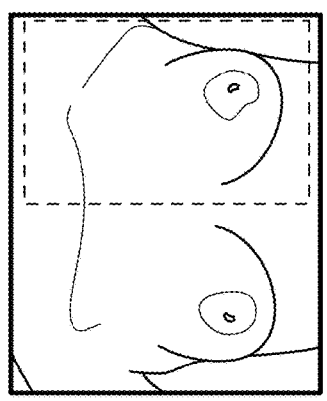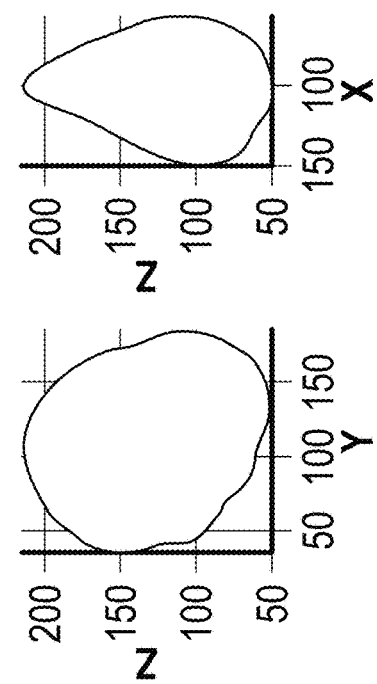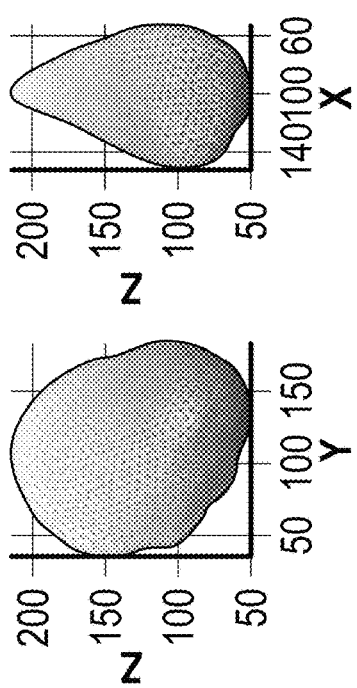
FIG. 16A

|  | Minimum | Median | Mean | Maximum | Standard Deviation |
|---|---|---|---|---|---|
| Height | 116.6 | 159.4 | 162.4 | 235.8 | 24.4 |
| Width | 131.9 | 160.6 | 162.5 | 224.7 | 17.5 |
| Depth | 16.4 | 59.2 | 60.5 | 98.2 | 15.7 |
|  |  |  |  |  |  |
| Height / Width | 0.73 | 0.99 | 1.00 | 1.31 | 0.11 |
| Depth / Height | 0.12 | 0.37 | 0.38 | 0.65 | 0.10 |
|  |  |  |  |  |  |
| # of Vertices | 4025 | 10069 | 10652 | 28820 | 3557 |
| # of Faces | 8046 | 20134 | 21300 | 57636 | 7114 |

FIG. 18A

| RMSD Between Models | Model B | Model C | Model D | Model E |
|---|---|---|---|---|
| Model A | 10.47 | 20.90 | 31.33 | 41.74 |
| Model B | - | 10.44 | 20.86 | 31.27 |
| Model C | - | - | 10.42 | 20.83 |
| Model D | - | - | - | 10.41 |

FIG. 18B

| RMSE Between Models | Model B | Model C | Model D | Model E |
|---|---|---|---|---|
| Model A | 11.56 | 23.10 | 34.65 | 46.20 |
| Model B | - | 11.54 | 23.09 | 34.64 |
| Model C | - | - | 11.55 | 23.09 |
| Model D | - | - | - | 11.55 |

FIG. 19A

| HD Between Models | Model B | Model C | Model D | Model E |
|---|---|---|---|---|
| Model A | 19.98 | 39.91 | 59.82 | 79.71 |
| Model B | - | 19.96 | 39.86 | 59.77 |
| Model C | - | - | 19.91 | 39.82 |
| Model D | - | - | - | 19.91 |

FIG. 19B

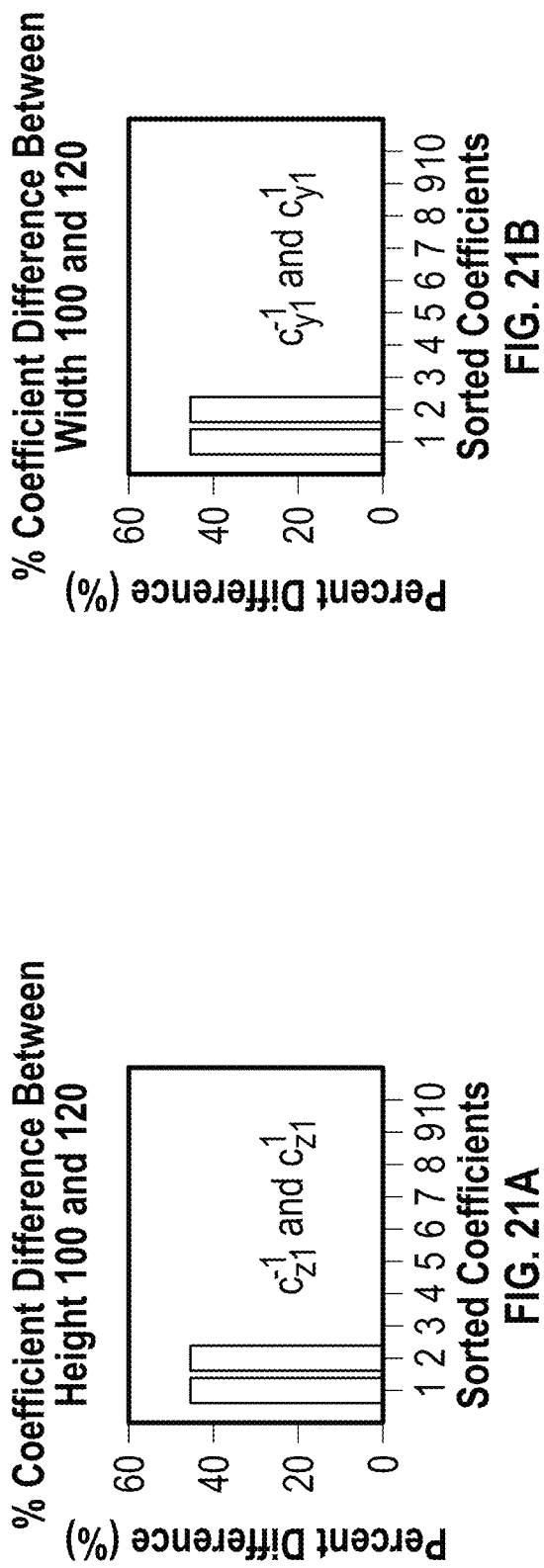
FIG. 21A
FIG. 21B
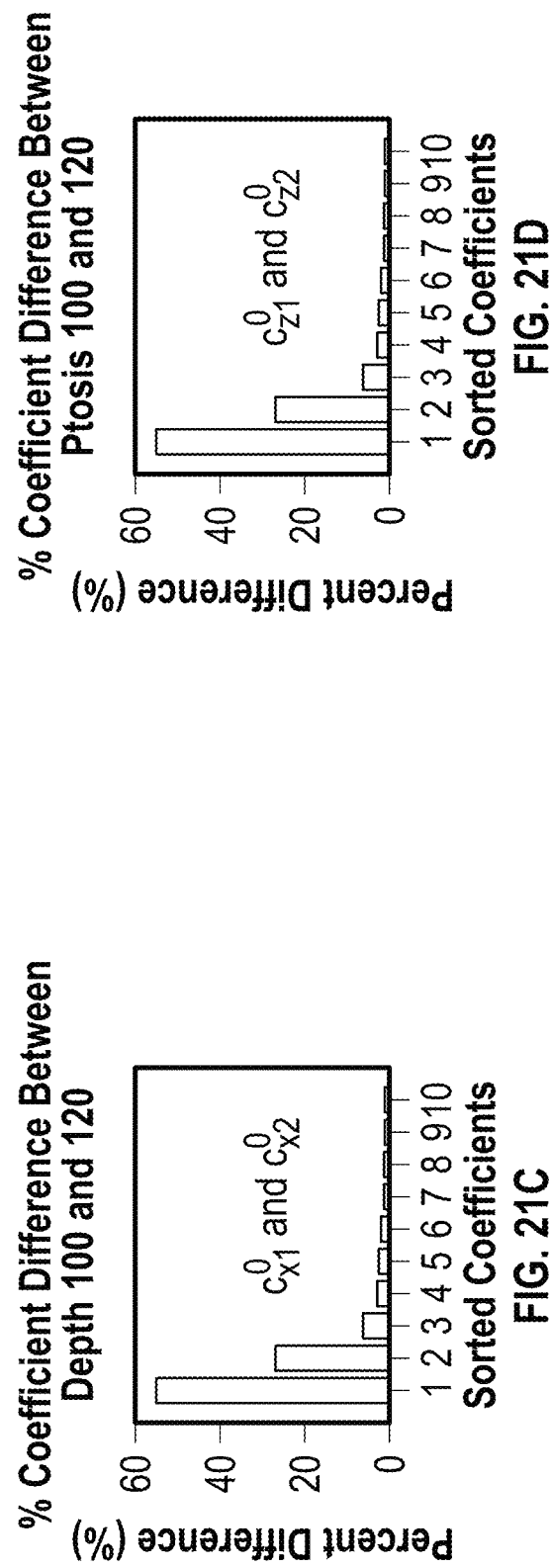
FIG. 21C
FIG. 21D

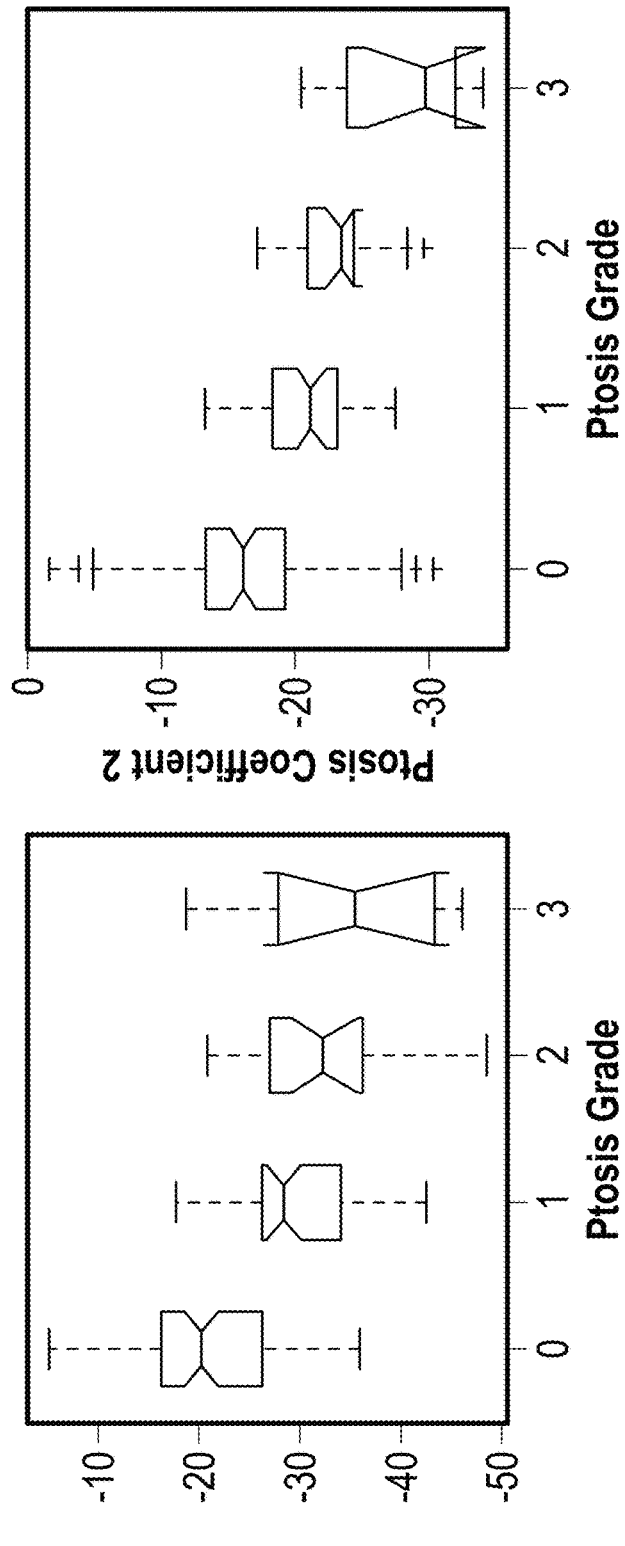

| Degree | Number of Computed SPHARM Models Where RMSE < 10mm (% Successful) N = 161 Samples Total | RMSE | | | |
|---|---|---|---|---|---|
| | | Minimum | Median | Mean | Maximum | Standard Deviation |
| 10 | 161 (100%) | 0.943 | 1.503 | 1.701 | 6.240 | 0.739 |
| 20 | 161 (100%) | 0.658 | 1.109 | 1.314 | 5.651 | 0.718 |
| 30 | 161 (100%) | 0.559 | 1.010 | 1.215 | 5.442 | 0.732 |
| 40 | 151 (93.8%) | 0.508 | 1.040 | 25.970 | 1728.378 | 182.042 |
| 50 | 87 (54.0%) | 0.493 | 5.842 | 5.52E+07 | 5.92E+09 | 5.19E+08 |

FIG. 26A

| Degree | Number of Computed SPHARM Models HD < 21mm (% Successful) N = 161 Samples Total | Hausdorff Distance (HD) | | | |
|---|---|---|---|---|---|
| | | Minimum | Median | Mean | Maximum | Standard Deviation |
| 10 | 161 (100%) | 2.331 | 5.026 | 5.668 | 20.782 | 2.610 |
| 20 | 161 (100%) | 2.109 | 3.489 | 4.149 | 20.234 | 2.406 |
| 30 | 159 (98.1%) | 2.353 | 3.595 | 4.933 | 70.601 | 6.460 |
| 40 | 129 (80.1%) | 2.43 | 4.65 | 891.41 | 56876.99 | 6096.27 |
| 50 | 60 (37.3%) | 37% | 2.82 | 157.38 | 1.30E+09 | 1.24E+11 |

FIG. 26B

| | Magnitude of the Coefficient Value (Mean ± Standard Deviation) | | | | |
|---|---|---|---|---|---|
| | Height ($c_{z1}^{-1}$) | Width ($c_{y1}^{1}$) | Depth($c_{x1}^{0}$) | Ptosis 1 ($c_{z1}^{0}$) | Ptosis 2 ($c_{z2}^{0}$) |
| Degree 10 | 101.23 ± 13.29 | 96.42 ± 9.63 | 61.91 ± 15.13 | 25.31 ± 8.33 | 18.51 ± 5.88 |
| Degree 20 | 101.18 ± 13.28 | 96.4 ± 9.63 | 61.89 ± 15.15 | 25.19 ± 8.3 | 18.64 ± 5.93 |
| Degree 30 | 101.2 ± 13.29 | 96.4 ± 9.63 | 61.89 ± 15.15 | 25.19 ± 8.3 | 18.62 ± 5.92 |
| Degree 40 | 99.72 ± 21.35 | 96.97 ± 19.08 | 61.78 ± 17.28 | 25.68 ± 13.48 | 20.2 ± 18.76 |
| Degree 50 | 7.04 × 10$^5$ ± 7.91 × 10$^6$ | 1.32 × 10$^6$ ± 1.77 × 10$^7$ | 4.51 × 10$^6$ ± 6.30 × 10$^7$ | 1.83 × 10$^6$ ± 3.08 × 10$^7$ | 1.23 × 10$^6$ ± 2.02 × 10$^7$ |

FIG. 28

| Degree A | Degree B | Height | Width | Depth | Ptosis 1 | Ptosis 2 |
|---|---|---|---|---|---|---|
| 10 | 20 | 0.911 | 0.958 | 0.945 | 0.842 | 0.784 |
| 10 | 30 | 0.967 | 0.972 | 0.952 | 0.835 | 0.809 |
| 10 | 40 | 0.941 | 0.990 | 0.989 | 0.958 | 0.951 |
| 20 | 30 | 0.941 | 0.946 | 0.937 | 0.962 | 0.758 |
| 20 | 40 | 0.989 | 0.934 | 0.985 | 0.908 | 0.973 |
| 30 | 40 | 0.940 | 0.953 | 0.986 | 0.884 | 0.936 |
| 10 | 50 | <0.001 | <0.001 | 0.002 | 0.030 | 0.030 |
| 20 | 50 | <0.001 | <0.001 | 0.002 | 0.022 | 0.047 |
| 30 | 50 | <0.001 | <0.001 | 0.002 | 0.020 | 0.045 |
| 40 | 50 | <0.001 | <0.001 | 0.002 | 0.027 | 0.048 |

FIG. 29

| Degree A | Degree B | Height | Width | Depth | Ptosis 1 | Ptosis 2 |
|---|---|---|---|---|---|---|
| 10 | 20 | 0.04 ± 0.05% | 0.03 ± 0.03% | 0.08 ± 0.07% | 0.45 ± 0.21% | 0.77 ± 0.76% |
| 10 | 30 | 0.04 ± 0.07% | 0.04 ± 0.06% | 0.08 ± 0.09% | 0.48 ± 0.22% | 0.63 ± 0.46% |
| 20 | 30 | 0.03 ± 0.03% | 0.02 ± 0.06% | 0.02 ± 0.04% | 0.07 ± 0.08% | 0.27 ± 0.56% |
| 10 | 40 | 0.52 ± 2.65% | 1.71 ± 11.8% | 1.47 ± 9.87% | 3.86 ± 27.8% | 11.3 ± 86.3% |
| 20 | 40 | 0.5 ± 2.66% | 1.69 ± 11.8% | 1.44 ± 9.89% | 3.58 ± 28.0% | 11.0 ± 87.4% |
| 30 | 40 | 0.5 ± 2.67% | 1.7 ± 11.8% | 1.42 ± 9.89% | 3.56 ± 28.1% | 11.1 ± 88.2% |
| 10 | 50 | >1000% | >1000% | >1000% | >1000% | >1000% |
| 20 | 50 | >1000% | >1000% | >1000% | >1000% | >1000% |
| 30 | 50 | >1000% | >1000% | >1000% | >1000% | >1000% |
| 40 | 50 | >1000% | >1000% | >1000% | >1000% | >1000% |

FIG. 30

| | MIDLINE AND INFRAMAMMARY FOLD DETECTION | BREAST CROPPING | CLOSED MESH OBJECT | SPHERICAL PARAMETERIZATION | SPHARM EXPANSION |
|---|---|---|---|---|---|
| SET 0 (GT) | 161 (100%) | 161 (100%) | 161 (100%) | 161 (100%) | 161 (100%) |
| SET 1 | 161 (100%) | 160 (99.4%) | 137 (85.1%) | 137 (85.1%) | 137 (85.1%) |
| SET 2 | 161 (100%) | 160 (99.4%) | 144 (89.4%) | 144 (89.4%) | 144 (89.4%) |
| SET 3 | 161 (100%) | 151 (93.8%) | 81 (50.3%) | 81 (50.3%) | 81 (50.3%) |
| SET 4 | 161 (100%) | 160 (99.4%) | 79 (49.1%) | 79 (49.1%) | 79 (49.1%) |

FIG. 33

| | EUCLIDEAN DISTANCE (MM) | | | | |
|---|---|---|---|---|---|
| | MINIMUM | MEDIAN | MEAN | MAXIMUM | STANDARD DEVIATION |
| LATERAL POINT | 0.00 | 17.48 | 19.02 | 75.29 | 13.60 |
| TRANSITION POINT | 3.31 | 27.72 | 28.50 | 59.96 | 13.21 |

FIG. 34

| | | EUCLIDEAN DISTANCE (MM) | | | | |
|---|---|---|---|---|---|---|
| | SET | MINIMUM | MEDIAN | MEAN | MAXIMUM | STANDARD DEVIATION |
| LATERAL POINT | 1 | 54.61 | 118.63 | 115.70 | 181.26 | 23.14 |
| | 2 | 56.87 | 112.95 | 112.38 | 183.27 | 20.08 |
| | 3 | 42.33 | 94.83 | 100.29 | 184.65 | 29.03 |
| | 4 | 2.40 | 83.40 | 82.63 | 178.45 | 26.43 |
| TRANSITION POINT | 1 | 52.27 | 89.50 | 89.87 | 126.32 | 13.97 |
| | 2 | 59.38 | 94.94 | 93.14 | 128.69 | 14.40 |
| | 3 | 22.07 | 75.33 | 73.81 | 128.78 | 20.57 |
| | 4 | 15.07 | 89.63 | 88.63 | 132.97 | 18.69 |

FIG. 35

| | MIDLINE AND INFRAMAMMARY FOLD DETECTION | BREAST CROPPING | CLOSED MESH OBJECT | SPHERICAL PARAMETERIZATION | SPHARM EXPANSION |
|---|---|---|---|---|---|
| SET 1 (GT) | 161 (100%) | 161 (100%) | 161 (100%) | 161 (100%) | 161 (100%) |
| SET 2 | 161 (100%) | 161 (100%) | 158 (98.1%) | 158 (98.1%) | 158 (98.1%) |
| SET 3 | 161 (100%) | 161 (100%) | 160 (99.4%) | 160 (99.4%) | 159 (98.8%) |
| SET 4 | 161 (100%) | 161 (100%) | 159 (98.8%) | 159 (98.8%) | 159 (98.8%) |
| SET 5 | 161 (100%) | 161 (100%) | 159 (98.8%) | 159 (98.8%) | 159 (98.8%) |
| SET 6 | 161 (100%) | 161 (100%) | 159 (98.8%) | 159 (98.8%) | 159 (98.8%) |
| SET 7 | 161 (100%) | 161 (100%) | 159 (98.8%) | 159 (98.8%) | 158 (98.1%) |
| SET 8 | 161 (100%) | 161 (100%) | 160 (99.4%) | 160 (99.4%) | 159 (98.8%) |
| SET 9 | 161 (100%) | 161 (100%) | 159 (98.8%) | 159 (98.8%) | 159 (98.8%) |

| | MIDLINE AND INFRAMAMMARY FOLD DETECTION | BREAST CROPPING | CLOSED MESH OBJECT | SPHERICAL PARAMETERIZATION | SPHARM EXPANSION |
|---|---|---|---|---|---|
| SET 1 (GT) | 161 (100%) | 161 (100%) | 161 (100%) | 161 (100%) | 161 (100%) |
| SET 2 | 161 (100%) | 161 (100%) | 161 (100%) | 161 (100%) | 161 (100%) |
| SET 3 | 161 (100%) | 161 (100%) | 159 (98.8%) | 159 (98.8%) | 159 (98.8%) |
| SET 4 | 161 (100%) | 161 (100%) | 160 (99.4%) | 160 (99.4%) | 160 (99.4%) |
| SET 5 | 161 (100%) | 161 (100%) | 160 (99.4%) | 160 (99.4%) | 160 (99.4%) |
| SET 6 | 161 (100%) | 161 (100%) | 159 (98.8%) | 159 (98.8%) | 159 (98.8%) |
| SET 7 | 161 (100%) | 161 (100%) | 161 (100%) | 161 (100%) | 161 (100%) |
| SET 8 | 161 (100%) | 161 (100%) | 160 (99.4%) | 160 (99.4%) | 160 (99.4%) |
| SET 9 | 161 (100%) | 161 (100%) | 160 (99.4%) | 160 (99.4%) | 160 (99.4%) |

| TP Movement | N Samples | Projection % Difference | | | | |
|---|---|---|---|---|---|---|
| | | Minimum | Median | Mean | Maximum | Standard Deviation |
| Lateral 6 mm | 161 | 0.00% | 0.17% | 0.30% | 3.34% | 0.43% |
| Lateral 3 mm | 159 | 0.00% | 0.11% | 0.24% | 3.37% | 0.43% |
| Medial 3 mm | 160 | 0.00% | 0.10% | 0.20% | 3.04% | 0.35% |
| Medial 6 mm | 160 | 0.00% | 0.14% | 0.23% | 1.78% | 0.29% |
| Down 6 mm | 159 | 0.01% | 0.45% | 0.69% | 4.90% | 0.84% |
| Down 3 mm | 161 | 0.01% | 0.30% | 0.47% | 3.53% | 0.57% |
| Up 3 mm | 160 | 0.00% | 0.24% | 0.35% | 3.19% | 0.40% |
| Up 6 mm | 160 | 0.00% | 0.35% | 0.55% | 5.07% | 0.66% |

FIG. 40

| TP Movement | N Samples | Volume % Difference | | | | |
|---|---|---|---|---|---|---|
| | | Minimum | Median | Mean | Maximum | Standard Deviation |
| Lateral 6 mm | 161 | 0.00% | 0.13% | 0.20% | 1.78% | 0.26% |
| Lateral 3 mm | 159 | 0.00% | 0.10% | 0.20% | 11.13% | 0.89% |
| Medial 3 mm | 160 | 0.00% | 0.11% | 0.12% | 0.43% | 0.10% |
| Medial 6 mm | 160 | 0.00% | 0.14% | 0.18% | 0.71% | 0.14% |
| Down 6 mm | 159 | 0.29% | 2.44% | 2.65% | 12.72% | 1.26% |
| Down 3 mm | 161 | 0.04% | 1.19% | 1.32% | 11.82% | 0.99% |
| Up 3 mm | 160 | 0.02% | 1.18% | 1.26% | 4.00% | 0.53% |
| Up 6 mm | 160 | 0.39% | 2.39% | 2.53% | 6.01% | 0.91% |

FIG. 41

Projection % Difference

| LP Movement | N Samples | Minimum | Median | Mean | Maximum | Standard Deviation |
|---|---|---|---|---|---|---|
| Down 6 mm | 158 | 0.01% | 0.65% | 0.81% | 5.31% | 0.82% |
| Down 3 mm | 160 | 0.00% | 0.36% | 0.55% | 3.57% | 0.60% |
| Up 3 mm | 159 | 0.00% | 0.37% | 0.54% | 3.43% | 0.58% |
| Up 6 mm | 159 | 0.00% | 0.44% | 0.58% | 5.24% | 0.60% |
| Forward 6 mm | 159 | 0.02% | 1.63% | 1.67% | 9.98% | 1.21% |
| Forward 3 mm | 159 | 0.01% | 0.74% | 0.86% | 3.09% | 0.63% |
| Backward 3 mm | 160 | 0.01% | 0.82% | 0.96% | 4.56% | 0.76% |
| Backward 6 mm | 159 | 0.01% | 1.73% | 1.83% | 5.73% | 1.12% |

FIG. 42

Volume % Difference

| LP Movement | N Samples | Minimum | Median | Mean | Maximum | Standard Deviation |
|---|---|---|---|---|---|---|
| Down 6 mm | 158 | 0.01% | 0.69% | 0.87% | 4.83% | 0.77% |
| Down 3 mm | 160 | 0.00% | 0.39% | 0.53% | 2.87% | 0.47% |
| Up 3 mm | 159 | 0.01% | 0.43% | 0.53% | 3.64% | 0.48% |
| Up 6 mm | 159 | 0.00% | 0.71% | 0.80% | 4.29% | 0.67% |
| Forward 6 mm | 159 | 0.05% | 2.52% | 2.55% | 11.07% | 1.17% |
| Forward 3 mm | 159 | 0.04% | 1.21% | 1.23% | 3.02% | 0.57% |
| Backward 3 mm | 160 | 0.13% | 1.29% | 1.33% | 4.59% | 0.64% |
| Backward 6 mm | 159 | 0.79% | 2.59% | 2.68% | 5.57% | 0.99% |

FIG. 43

| k-NN (k=3) | | Predicted Class | | | | Naïve Bayes | | Predicted Class | | |
|---|---|---|---|---|---|---|---|---|---|---|
| | | Implant | TRAM | Precision | | | | Implant | TRAM | Precision |
| Actual Class | Implant | 15 | 9 | 62.5% | | Actual Class | Implant | 15 | 9 | 62.5% |
| | TRAM | 5 | 24 | 82.8% | | | TRAM | 12 | 17 | 58.6% |
| | Recall | 75.0% | 72.7% | 73.6% | | | Recall | 55.6% | 65.4% | 60.4% |
| k-NN (k=5) | | Predicted Class | | | | QDA | | Predicted Class | | |
| | | Implant | TRAM | Precision | | | | Implant | TRAM | Precision |
| Actual Class | Implant | 15 | 9 | 62.5% | | Actual Class | Implant | 16 | 8 | 66.7% |
| | TRAM | 3 | 26 | 89.7% | | | TRAM | 10 | 19 | 65.5% |
| | Recall | 83.3% | 74.3% | 77.4% | | | Recall | 61.5% | 70.4% | 66.0% |

FIG. 46A

| k-NN (k=3) | | Predicted Class | | Precision | Naïve Bayes | | | Predicted Class | | Precision |
|---|---|---|---|---|---|---|---|---|---|---|
| | | Implant | TRAM | | | | | Implant | TRAM | |
| Actual Class | Implant | 13 | 11 | 54.2% | Actual Class | Implant | | 16 | 8 | 66.7% |
| | TRAM | 6 | 25 | 79.3% | | TRAM | | 13 | 16 | 55.2% |
| | Recall | 68.4% | 67.6% | 67.9% | | Recall | | 55.2% | 66.7% | 60.4% |
| k-NN (k=5) | | Predicted Class | | Precision | QDA | | | Predicted Class | | Precision |
| | | Implant | TRAM | | | | | Implant | TRAM | |
| Actual Class | Implant | 13 | 11 | 54.2% | Actual Class | Implant | | 14 | 10 | 58.3% |
| | TRAM | 3 | 26 | 89.7% | | TRAM | | 10 | 19 | 65.5% |
| | Recall | 81.3% | 70.3% | 73.6% | | Recall | | 58.3% | 65.5% | 62.3% |

FIG. 46B

Breast Images | Corresponding SPHARM Models
Reference
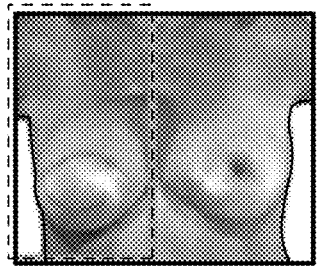
RMSD: 5.5071
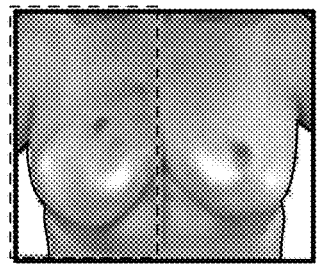
RMSD: 6.0221
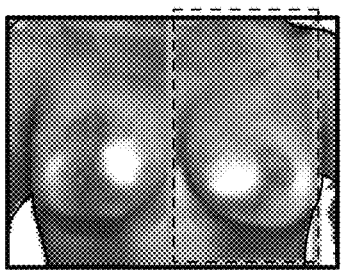
RMSD: 6.0341
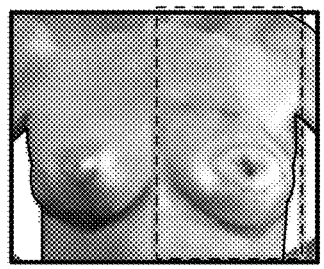
RMSD: 7.1552
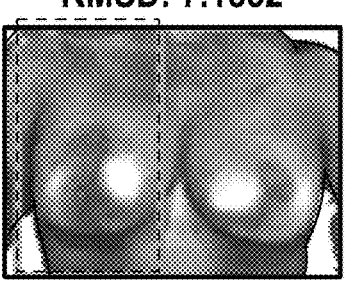
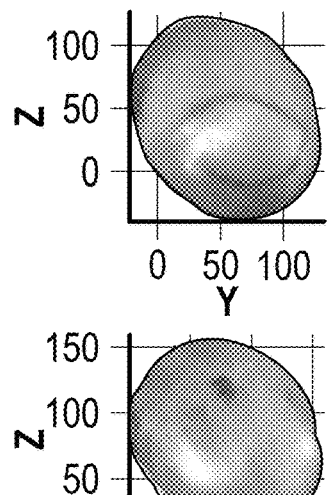 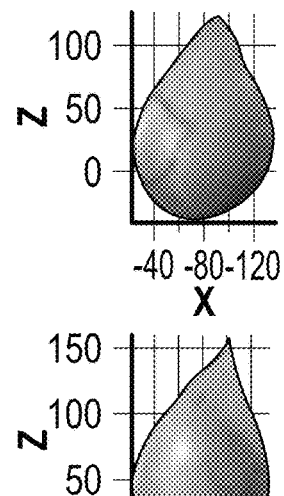
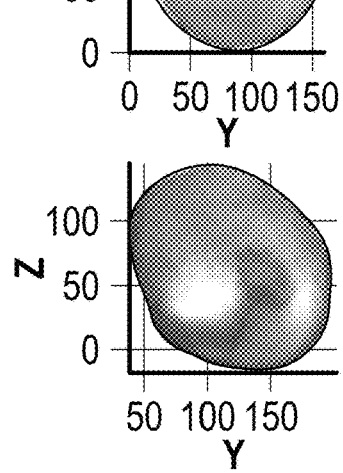 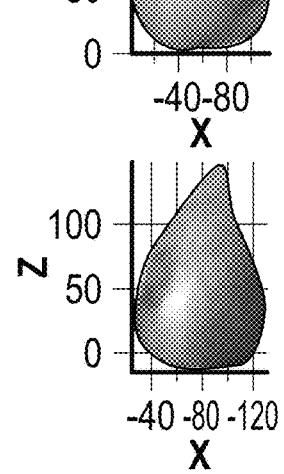
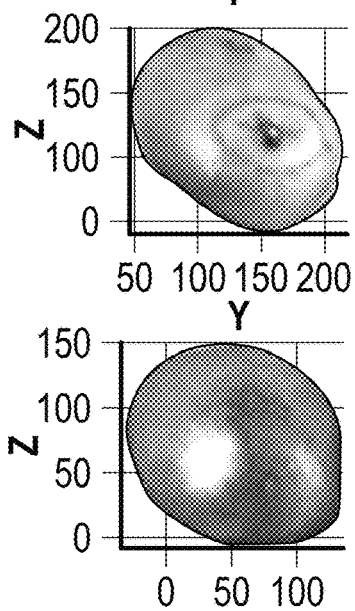 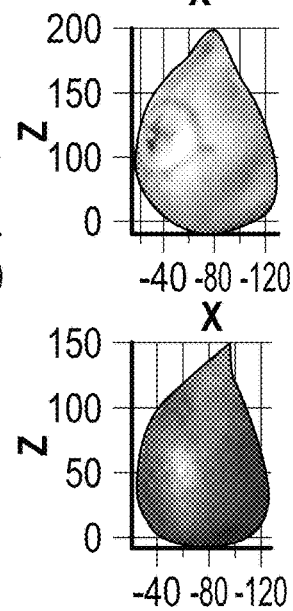
FIG. 49A
FIG. 49B Breast Images | Corresponding SPHARM Models
Front View | Side View
Reference
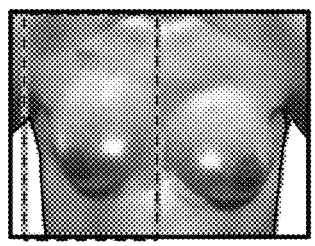
RMSD: 3.8898
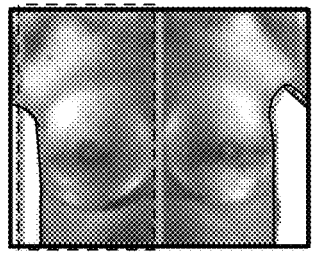
RMSD: 4.7804
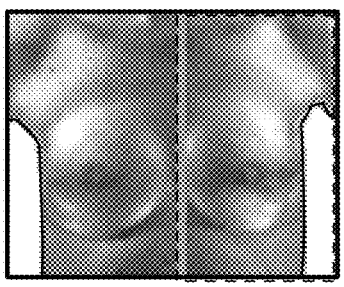
RMSD: 5.342
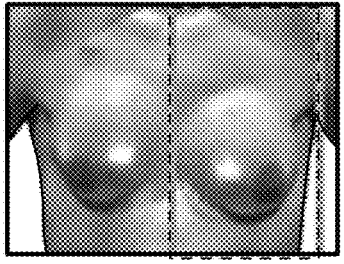
RMSD: 5.5427
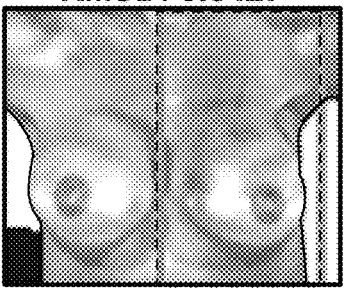
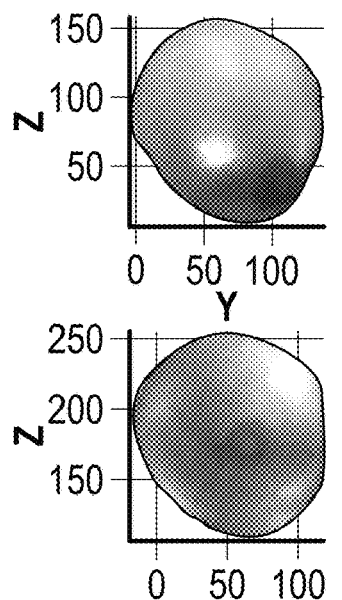
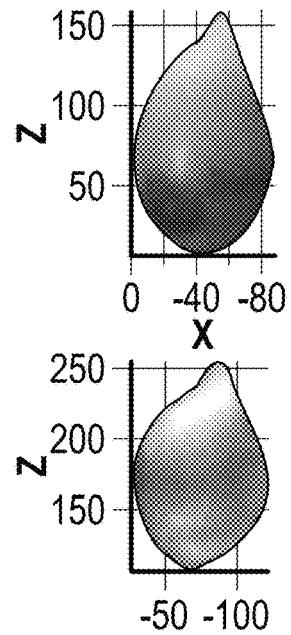
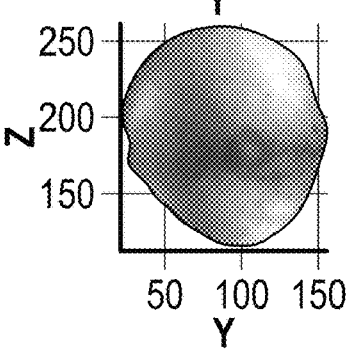
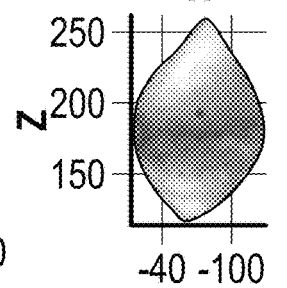
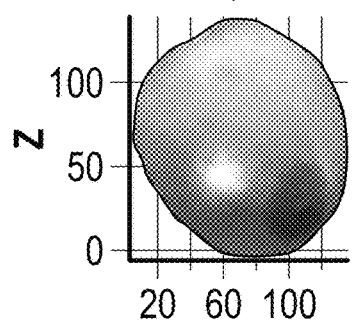
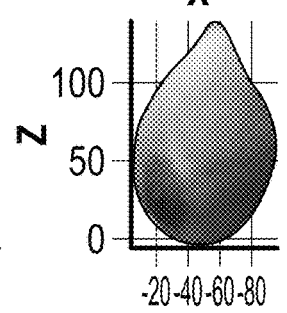
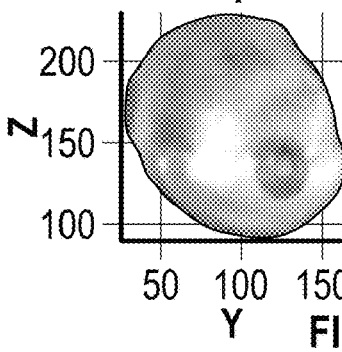
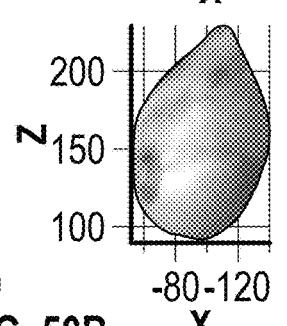
FIG. 50A
FIG. 50B

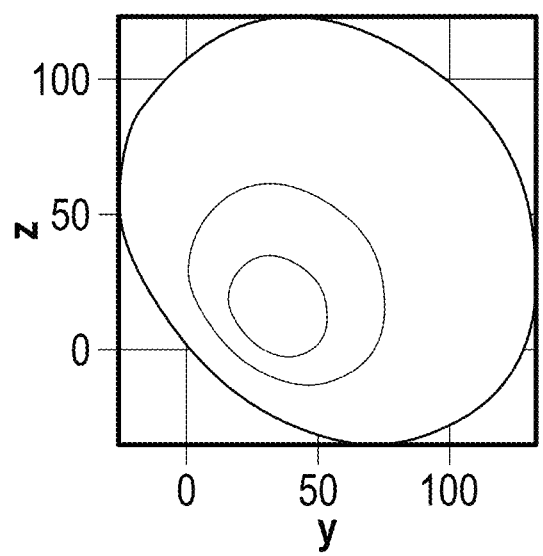
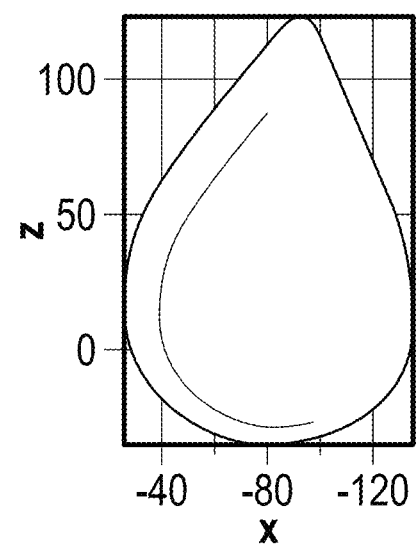
FIG. 51A
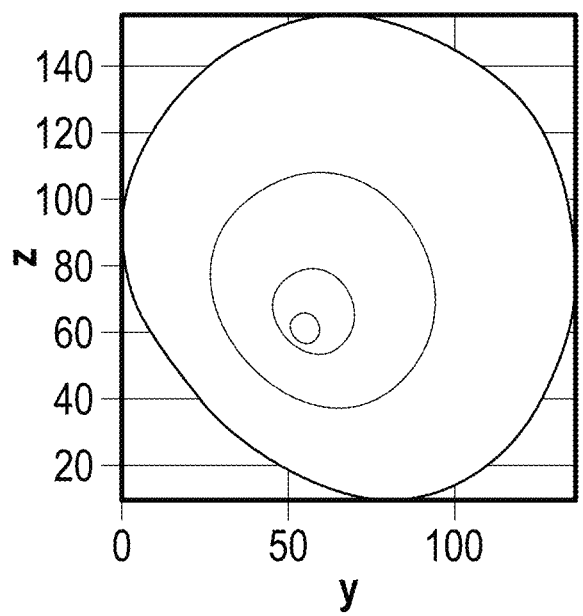
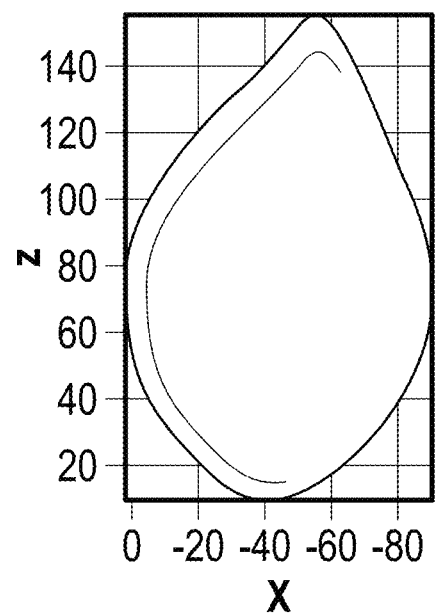
FIG. 51B

| Comparisons | | N Patients | RMSD | |
|---|---|---|---|---|
| Left Breast | Right Breast | | Average | Std |
| Implant | Implant | 9 | 6.51 | 2.23 |
| TRAM flap | TRAM flap | 10 | 8.98 | 3.99 |
| Natural | TRAM flap | 1 | 9.60 | - |
| DIEP flap | TRAM flap | 1 | 11.31 | - |
| Revision | Implant | 3 | 8.46 | 1.35 |
| TRAM flap | Revision | 3 | 10.04 | 4.64 |
| Implant | LD | 1 | 4.95 | - |
| TRAM flap | Implant | 1 | 9.96 | - |

FIG. 52A

| Comparisons | N Comparisons | Root-Mean-Squared Distance (RMSD) | | | | |
|---|---|---|---|---|---|---|
| | | Min | Median | Mean | Max | Std |
| Preoperative: Left Breast - Right Breast | 29 | 2.81 | 7.02 | 8.88 | 22.84 | 5.64 |
| Postoperative: Left Breast - Right Breast | 29 | 4.25 | 8.26 | 8.27 | 16.37 | 3.26 |
| Preoperative: One Breast - Other Breast | 1711 | 2.81 | 16.69 | 17.38 | 38.68 | 5.71 |
| Postoperative: One Breast - Other Breast | 1891 | 3.89 | 14.75 | 15.56 | 38.22 | 5.92 |
| Postoperative: Actual - Predicted (Closest Shape Without Averaging) | 53 | 7.12 | 14.13 | 14.24 | 28.13 | 4.12 |
| Postoperative: Actual - Predicted (Closest Shape Using First 27 Coefficients) | 53 | 7.45 | 13.60 | 14.09 | 28.06 | 4.02 |
| Postoperative: Actual - Predicted (Farthest Shape Without Averaging) | 53 | 12.56 | 19.07 | 20.99 | 35.70 | 5.69 |
| Postoperative: Actual - Predicted (Closest Shape With Averaging) | 53 | 5.93 | 12.56 | 12.99 | 24.43 | 3.52 |
| Postoperative: Actual - Predicted (Farthest Shape With Averaging) | 53 | 9.52 | 15.57 | 16.09 | 29.52 | 4.60 |
| Preoperative - Postoperative | 53 | 5.42 | 14.54 | 13.83 | 29.75 | 4.76 |
| Preoperative - Predicted (Closest Shape With Averaging) | 53 | 4.94 | 10.46 | 10.28 | 20.18 | 3.55 |

FIG. 52B

| BMI | N | Minimum | Median | Mean | Maximum | STD |
|---|---|---|---|---|---|---|
| | | | | RMSD | | |
| <25 | 13 | 6.17 | 9.22 | 9.64 | 14.93 | 2.60 |
| 25-29.9 | 21 | 6.19 | 8.86 | 10.25 | 17.11 | 2.87 |
| >30 | 19 | 9.21 | 14.46 | 14.31 | 22.82 | 3.49 |

FIG. 52C

| BMI | N | Minimum | Median | Mean | Maximum | STD |
|---|---|---|---|---|---|---|
| | | | | Hausdorff Distance | | |
| <25 | 13 | 11.23 | 18.03 | 19.76 | 31.04 | 5.99 |
| 25-29.9 | 21 | 10.02 | 19.15 | 20.49 | 37.58 | 6.49 |
| >30 | 19 | 18.73 | 28.03 | 28.37 | 52.51 | 8.41 |

FIG. 52D

| Patient ID | Procedure | RMSD | | |
|---|---|---|---|---|
| | | (P1, P2) | (Transformed P1, P2) | (Transformed P1, P1) |
| 581 | Reduction | 10.1185 | 1.28E-14 | 10.1185 |
| 700 | Augmentation | 14.3231 | 5.56E-15 | 14.3231 |
| 766 | Mastopexy | 11.6918 | 4.43E-15 | 11.6918 |

FIG. 56

SYSTEMS AND METHODS FOR MODELING THE BREAST USING SPHERICAL HARMONICS

CROSS-REFERENCE TO RELATED APPLICATIONS

This application is a U.S. National Stage Application filed under 35 U.S.C. § 371(a) claiming the benefit of and priority to International Patent Application No. PCT/US2020/029783, filed on Apr. 24, 2020, which claims the benefit of and priority to U.S. Provisional Patent Application Ser. No. 62/838,997, filed on Apr. 26, 2019, the entire contents of both applications are incorporated by reference herein.

GOVERNMENT SUPPORT

This invention was made with government support under CA143190 and CA203984 awarded by the National Institutes of Health. The government has certain rights in the invention.

TECHNICAL FIELD

The present application relates to systems and methods for the modeling of breasts, and in particular, to the modeling of breasts using spherical harmonics.

SUMMARY

This disclosure relates to systems and methods for the modeling of breasts using spherical harmonics. In accordance with aspects of the present disclosure, a computer implemented method of modeling breast shape is presented. The method includes receiving a three-dimensional (3D) image including a breast, identifying the breast in the 3D image, extracting 3D image data of the breast from the 3D image, forming a closed object using the 3D image data of the breast to create a zero-genus surface, mapping the 3D image data of the breast to a predefined template using spherical coordinates, and determining a 3D spherical harmonic descriptor of the 3D image data of the breast based on a least squares estimation.

In an aspect of the present disclosure, the method further includes identifying parameters of the 3D spherical harmonic descriptor that represent anatomical breast parameters including at least one of a height, a width, a depth, or ptosis.

In another aspect of the present disclosure, the method further includes identifying different types of breast shapes, including at least one of a natural breast shape, a surgically altered breast shape, an autologous breast, an implant reconstructed breast, and/or a combination of autologous and implant breasts, based on spherical harmonic (SPHARM) coefficients.

In an aspect of the present disclosure, the 3D image is a patient's preoperative image. The method further includes, predicting a post-operative breast shape from the 3D image based on the 3D SPHARM model, and outputting a predicted 3D image based on the predicted post-operative breast shape.

In yet another aspect of the present disclosure, the predicting may include searching a database for a 3D image of at least one second patient with similar demographics and/or medical history, to the patient of the received 3D image. The database may include pre-operative and post-operative 3D images. The predicting may further include locating a pre-operative 3D image of a second patient with a similar age, BMI (Body Mass Index), breast size, and/or breast shape, locating a post-operative 3D image of the second patient with the similar age, breast size, and/or breast shape, generating an average pre-operative 3D image based on the pre-operative 3D images, generating an average post-operative 3D image based on the post-operative 3D images, determining SPHARM coefficients of at least one of the average post-operative and/or pre-operative 3D image or a located post-operative 3D image, determining SPHARM coefficients of the received 3D image, determining a difference between SPHARM coefficients of the received 3D image and SPHARM coefficients of the average post-operative 3D image, and/or determining a difference between SPHARM coefficients of the average pre-operative image and SPHARM coefficients of the average post-operative 3D image, applying the difference in SPHARM coefficients to the received 3D image, and morphing the breast of the received 3D image based on the determined SPHARM coefficients.

In yet another aspect of the present disclosure, the predicting may include identifying, in a database, a post-op 3D image of at least one second patient with similar demographics or medical history, to the patient of the received 3D image, wherein the database may include post-operative 3D images of breasts, generating a template post-operative 3D image based on the identified post-operative images to represent a particular outcome and patient type based on at least one of age, BMI, ethnicity/race, determining SPHARM coefficients of the received 3D image and the SPHARM coefficients of the template, determining a difference between the SPHARM coefficients of the received 3D image and the SPHARM coefficients of the template, applying the difference in SPHARM coefficients to the received 3D image, and morphing the breast of the received 3D image based on the determined SPHARM coefficients.

In a further aspect of the present disclosure, the predicting may include using a machine learning algorithm, where training data inputs include pre-operation image and/or model data, post operation image and/or model data, and/or patient demographic data.

In a further aspect of the present disclosure, the machine learning algorithm may include a neural network, random forest regression, linear regression (LR), ridge regression (RR), least-angle regression (LARS), and/or least absolute shrinkage and selection operator regression (LASSO).

In a further aspect of the present disclosure, the method may include identifying different types of breast shapes based on position including at least one of upright, supine, prone, or any position there between, generating position specific templates. The outputting may be based on patient position including at least one of upright, supine, prone, or any position there between.

In an aspect of the present disclosure, the different types of breast shapes may include natural, unnatural, surgically altered, and/or aged.

In an aspect of the present disclosure, the forming of a closed object may include identifying holes in a first mesh by finding boundary edges, which are edges that are not shared by two faces, calculating the angle between adjacent boundary edges at a vertex, and locating the smallest angle and creating a new triangle at the vertex. Creating a second mesh to substantially fill the identified holes. A location of a second vertex may be determined by an average edge length and the shortest direction to close a gap across the two meshes. Forming of a closed object may further include computing a distance between every newly created vertex and every related boundary vertex, and in a case where the distance between them is less than a predetermined threshold they are merged. Forming of a closed object may further include updating the mesh based on the computed distance.

In an aspect of the present disclosure, the 3D image may be a patient's preoperative image. The instructions, when executed, may further cause the system to: predict a post-operative breast shape from the 3D image based on the 3D spherical harmonic (SPHARM) model and output a predicted 3D image based on the predicted post-operative breast shape.

In an aspect of the present disclosure, a system for modeling a breast shape includes a processor and a memory. The memory includes instructions, which when executed by the processor, cause the system to receive a 3D image including a breast, identify the breast in the 3D image, extract 3D image data of the breast from the 3D image, form a closed object using the 3D image data of the breast to create a zero-genus surface, map the 3D image data of the breast to a predefined template using spherical coordinates, and determine a 3D spherical harmonic descriptor of the 3D image data of the breast.

In an aspect of the present disclosure, the instructions, when executed, may further cause the system to identify parameters of the 3D spherical harmonic descriptor that represent anatomical breast parameters including a height, a width, a depth, and/or ptosis.

In an aspect of the present disclosure, the instructions, when executed, may further cause the system to identify different types of breast shapes, including natural breast shape, cosmetically altered breast shape, surgically reconstructed breast shape, reduction mammoplasty, reduction mastopexy, augmentation mammoplasty, augmentation mastopexy, or correction of any breast shape deformities, based on spherical harmonic coefficients.

In an aspect of the present disclosure, the 3D image may be a patient's preoperative image. The instructions, when executed, may further cause the system to: predict a post-operative breast shape from the 3D image based on the 3D SPHARM model and output a predicted 3D image based on the predicted post-operative breast shape.

In an aspect of the present disclosure, when predicting, the instructions, when executed, may further cause the system to search a database for a 3D image of at least one second patient with similar demographics or medical history, to the received the patient of the 3D image, wherein the database includes pre-operative and post-operative 3D images, determine SPHARM coefficients of the received 3D image, locate a pre-operative 3D image of a second patient with a similar age, breast size, and/or breast shape based on the SPHARM coefficients, locate a post-operative 3D image of the second patient, generate an average pre-operative 3D image based on the pre-operative 3D images, generate an average post-operative 3D image based on the post-operative 3D images, determine SPHARM coefficients of at least one of the average pre-operative 3D image, determine SPHARM coefficients of the average post-operative 3D image and/or a located post-operative 3D image, determine a difference between SPHARM coefficients of the received 3D image and/or the average pre-operative image and SPHARM coefficients of the average post-operative 3D image, apply the difference in SPHARM coefficients to the received 3D image, and morph the breast of the received 3D image based on the determined SPHARM coefficients.

In an aspect of the present disclosure, when predicting, the instructions, when executed, may further cause the system to identify, in a database, a post-op 3D image of at least one second patient with similar demographics or medical history, or breast shape to the patient of the received 3D image. The database may include post-operative 3D images of breasts. When predicting, the instructions may further cause the system to generate a template post-operative 3D image based on the identified post-operative images to represent a particular outcome, determine SPHARM coefficients of the received 3D image and the SPHARM coefficients of the template, determine a difference between the SPHARM coefficients of the received 3D image and the SPHARM coefficients of the template, apply the difference in SPHARM coefficients to the received 3D image, and morph the breast of the received 3D image based on the determined SPHARM coefficients.

In an aspect of the present disclosure, the predicting may include using a machine learning algorithm, where training data inputs include at least one of pre and post operation image data or patient demographic data, wherein the machine learning algorithm includes a neural network, random forest regression, linear regression (LR), ridge regression (RR), least-angle regression (LARS), and/or least absolute shrinkage and selection operator regression (LASSO).

In an aspect of the present disclosure, a non-transitory storage medium that stores a program causing a computer to execute a method for modeling a breast shape. The method includes receiving a 3D image including a breast, identifying the breast in the 3D image, extracting 3D image data of the breast from the 3D image, forming a closed object using the 3D image data of the breast to create a zero-genus surface, mapping the 3D image data of the breast to a predefined template using spherical coordinates, and determining a 3D spherical harmonic descriptor of the 3D image data of the breast.

Further details and aspects of exemplary embodiments of the present disclosure are described in more detail below with reference to the accompanying drawings.

BRIEF DESCRIPTION OF THE DRAWINGS

A better understanding of the features and advantages of the disclosed technology will be obtained by reference to the following detailed description that sets forth illustrative embodiments, in which the principles of the technology are utilized, and the accompanying drawings of which:

FIGS. 1A-B are diagrams of autologous reconstruction and implant reconstruction, in accordance with aspects of the present disclosure;

FIGS. 2A-C are examples of a 3D image of the front torso, in accordance with aspects of the present disclosure;

FIGS. 5A-G are examples of five global deformations applied to an asymmetric superquadric, in accordance with aspects of the present disclosure;

FIG. 6A is a table of the baseline characteristics of 87 patients;

FIG. 6B is a table of the baseline clinical characteristics of the patients' breasts, in accordance with aspects of the present disclosure;

FIG. 6C is a table of the demographics of 32 patients who underwent TRAM flap and/or implant reconstruction, in accordance with aspects of the present disclosure;

FIG. 6D is a table of the procedure for each breast, in accordance with aspects of the present disclosure;

FIG. 6E is a table of the patient demographics at the time of their preoperative image, in accordance with aspects of the present disclosure;

FIGS. 7A-B are histograms of the number of vertices along the x direction and the y direction, in accordance with aspects of the present disclosure;

FIGS. 7C-E are midline point detection graphs, in accordance with aspects of the present disclosure;

FIG. 7F is a graph of inframammary fold detection, in accordance with aspects of the present disclosure;

FIGS. 9A-C are diagrams of breast cropping, in accordance with aspects of the present disclosure;

FIGS. 11A-B are diagrams of the front and side views of the breast model and its associated coordinate system, in accordance with aspects of the present disclosure;

FIGS. 12A-E are diagrams of a breast modeled with different degrees using a spherical harmonic MATLAB (SPHARM-MAT) toolbox, in accordance with aspects of the present disclosure;

FIGS. 16A-C are graphs of spherical harmonic (SPHARM) models of a small, a medium, and a large breast, in accordance with aspects of the present disclosure;

FIG. 18A is a table summarizing the height, width, depth, and number of faces and vertices of the SPHARM breast models, in accordance with aspects of the present disclosure;

FIG. 18B is a table of the root-mean-squared distance (RMSD) between the synthetic models, in accordance with aspects of the present disclosure;

FIG. 19A is a table of the RMSE between the synthetic models, in accordance with aspects of the present disclosure;

FIG. 19B is a table of the Hausdorff distance (HD) between the synthetic models, in accordance with aspects of the present disclosure;

FIGS. 21A-D are bar plots of the coefficient differences for height, width, depth, and ptosis, in accordance with aspects of the present disclosure;

FIGS. 23A-B are boxplots of the ptosis coefficients versus the ptosis grade rating, in accordance with aspects of the present disclosure;

FIGS. 24A-B are tables of the P-values, in accordance with aspects of the present disclosure;

FIG. 26A is a table of the statistics of the RMSE between the ground truth data set and the reconstructed SPHARM models, in accordance with aspects of the present disclosure;

FIG. 26B is a table of the statistics of the Hausdorff distance between the ground truth data set and the reconstructed SPHARM models, in accordance with aspects of the present disclosure;

FIG. 28 is a table of the magnitude of the SPHARM coefficients for different degrees, in accordance with aspects of the present disclosure;

FIG. 29 is a table of the P-values from the Wilcoxon rank-sum test comparing the five coefficient values between different degrees, in accordance with aspects of the present disclosure;

FIG. 30 is a table of the average percent difference in the SPHARM coefficients correlated to height, width, depth, and ptosis between different degrees relative to the SPHARM coefficient, in accordance with aspects of the present disclosure;

FIG. 33 is a table of the rate of successful processing at each step of the algorithm for different landmark positions, in accordance with aspects of the present disclosure;

FIG. 34 is a table of the Euclidean distance of the user selection relative to the ground truth selection for 10 images, in accordance with aspects of the present disclosure;

FIG. 35 is a table of the Euclidean distance of the corner selections relative to the ground truth selection, in accordance with aspects of the present disclosure;

FIG. 40 is a table depicting statistics on the projection percent difference between the ground truth selection and shifting the transition point (TP) 3 and 6 mm in different directions, in accordance with aspects of the present disclosure;

FIG. 41 is a table depicting statistics on the volume percent difference between the ground truth selection and shifting the transition point (TP) 3 and 6 mm in different directions, in accordance with aspects of the present disclosure;

FIG. 42 is a table depicting statistics on the projection percent difference between the ground truth selection and shifting the lateral point (LP) 3 and 6 mm in different directions, in accordance with aspects of the present disclosure;

FIG. 43 is a table depicting statistics on the volume percent difference between the ground truth selection and shifting the lateral point (LP) 3 and 6 mm in different directions, in accordance with aspects of the present disclosure;

FIG. 46A is a set of confusion matrices for k-nearest neighbor classification, quadratic discriminate analysis, and Naïve Bayes classifier using the SPHARM coefficients, in accordance with aspects of the present disclosure;

FIG. 46B is a set of confusion matrices for k-nearest neighbor classification, quadratic discriminate analysis, and Naïve Bayes classifier using BMI, breast volume, and breast dimensions, in accordance with aspects of the present disclosure;

FIGS. 49A-B are depictions of examples of a TRAM reconstructed breast (reference) and its four nearest neighbors based on the RMSD, in accordance with aspects of the present disclosure;

FIGS. 50A-B are depictions of examples of an implant reconstructed breast and its four nearest neighbors based on the RMSD, in accordance with aspects of the present disclosure;

FIG. 51A is a graph of the front and side views of the average breast model, in accordance with aspects of the present disclosure;

FIG. 51B is a graph of the front and side views of the average breast model, in accordance with aspects of the present disclosure;

FIG. 52A is a table of the procedures conducted on the left and right breast of each patient and the average RMSD for each set of patients with the same procedures, in accordance with aspects of the present disclosure;

FIG. 52B is a table of the statistics on the RMSD comparing preoperative, postoperative, and predicted breast shapes, in accordance with aspects of the present disclosure;

FIG. 52C is a table of the RMSD between the true postoperative models and the predicted models organized into three BMI groups, in accordance with aspects of the present disclosure;

FIG. 52D is a table of the Hausdorff distance between the true postoperative models and the predicted models organized into three BMI groups, in accordance with aspects of the present disclosure;

FIG. 56 is a table of RMSD comparisons between the pre-op breast shape SPHARM coefficients, the transformed pre-op breast coefficient, and actual post—op coefficients for three patients, in accordance with aspects of the present disclosure;

Figure 3A:
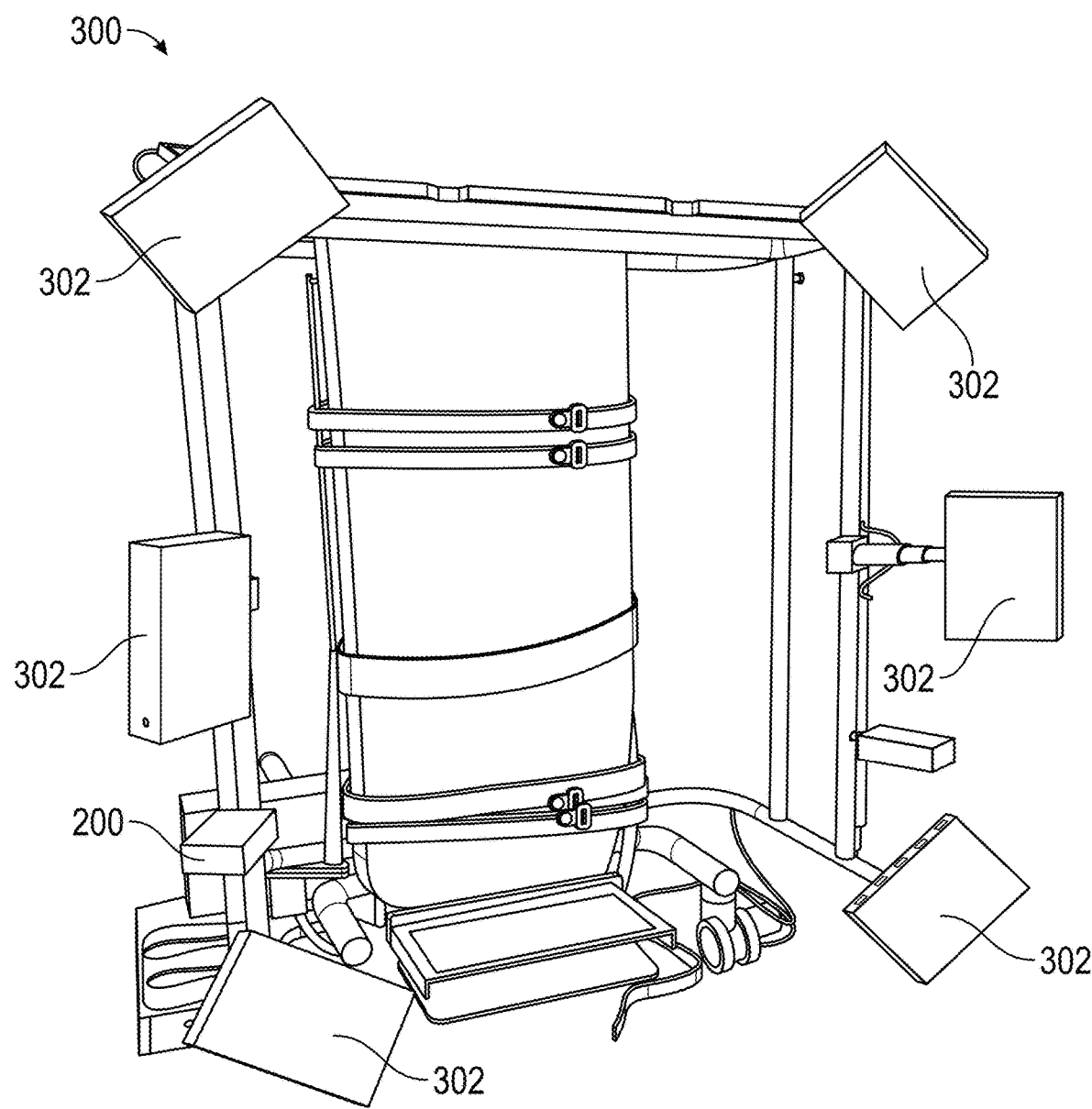
FIG. 3A is an image of a medical imaging system, in accordance with aspects of the present disclosure.

Further details and aspects of various embodiments of the present disclosure are described in more detail below with reference to the appended drawings.

DETAILED DESCRIPTION

This disclosure relates to the modeling of breasts using spherical harmonics.

Although the present disclosure will be described in terms of specific embodiments, it will be readily apparent to those skilled in this art that various modifications, rearrangements, and substitutions may be made without departing from the spirit of the present disclosure. The scope of the present disclosure is defined by the claims appended hereto.

For purposes of promoting an understanding of the principles of the present disclosure, reference will now be made to exemplary embodiments illustrated in the drawings, and specific language will be used to describe the same. It will nevertheless be understood that no limitation of the scope of the present disclosure is thereby intended. Any alterations and further modifications of the inventive features illustrated herein, and any additional applications of the principles of the present disclosure as illustrated herein, which would occur to one skilled in the relevant art and having possession of this disclosure, are to be considered within the scope of the present disclosure.

As the number of cosmetic and reconstructive breast surgeries performed has been steadily increasing over the years, there is a greater need for improved technologies, such as developing a computational three-dimensional breast model. Referring to FIGS. 1A-B, two general types of cosmetic and reconstructive breast procedures are shown. Two common procedures performed are autologous reconstruction using a transverse rectus abdominis (TRAM) flap is shown in FIG. 1A and implant reconstruction is shown in 1B. In order to improve the results of these surgeries, computational three-dimensional breast model may be used. According the present disclosure, a method using spherical harmonics is employed to produce the three-dimensional breast models.

Spherical harmonics are a complete series of orthogonal functions defined on the surface of a sphere. The spherical harmonic (SPHARM) method, converts a 3D object of spherical topology into three sets of SPHARM coefficients that describe its overall shape in terms of three sets of spherical harmonics basis functions (one set for each dimension). SPHARM has applicability to several fields including computer vision and computer graphics but has been most aptly applied in studying medical images, particularly in brain morphometry. There are several inherent properties of this shape descriptor that make it an advantageous method for medical image analysis. It can be compactly represented, allows for efficient shape comparison, incorporates implicit interpolation since the spherical domain is continuous, and can be used to establish surface correspondence. In addition, it can be processed in both the spatial and frequency domain.

A 3D imaging system may be used to record 3D images of the frontal portion of female torsos. The imaging system may represent a 3D image in the form of a triangular mesh that contains, for example about 75,000 vertices and 140,000 faces for each patient image. Each face also has texture associated with it, so a 3D texture image can also be viewed. The vertices may be spaced about 3 mm apart from each other and the stated error is less than 0.5 mm. Referring to FIGS. 2A-C, the 3D surface image can be viewed as a 3D point cloud (FIG. 2A), a triangular mesh (FIG. 2B), or a 3D texture image overlaid on the triangular mesh (FIG. 2C).

With reference to FIG. 3A an exemplary imaging system 300 is shown. The exemplary imaging system 300 may include six modular camera units 302 and may use, for example, stereophotogrammetry to estimate a 3D surface image from pairs of 2D photographs. These camera units 302 may be effectively positioned around a person (top, middle, and bottom) to improve the 3D surface coverage of the front torso. Each camera unit 302 may be equipped with a pair of stereo cameras and a color camera. The stereo cameras may be synchronized to initiate together and has a 1.5 millisecond capture speed. A half millisecond later, the color cameras may be triggered to capture 2D photographs from six different viewpoints. The system then employs a sophisticated software algorithm to unify the images from the six camera units. Once the 3D surface image is fully generated, the color photographs are mapped to the generated triangular mesh. The illustrated example uses stereophotogrammetry, however, other forms of 3D imaging (such as a portable handheld 3D scanner, or IPAD Pro, or others) are contemplated.

Figure 3B:
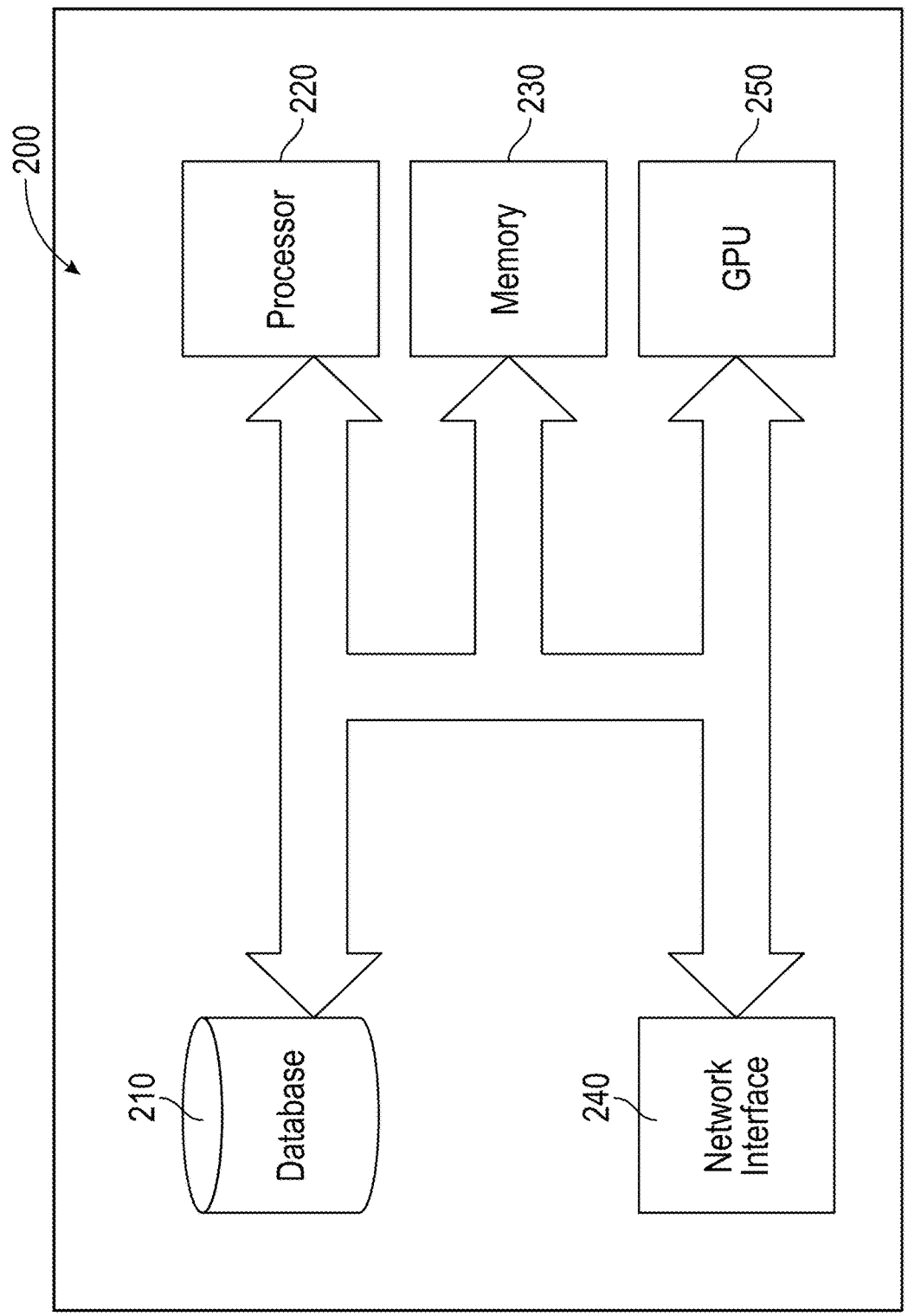
FIG. 3B is diagram of an exemplary controller, in accordance with aspects of the present disclosure.

Referring now to FIG. 3B, there is shown an illustration of exemplary components in the controller 200 of FIG. 3A, in accordance with aspects of the present disclosure. The controller 200 includes, for example, a database 210, one or more processors 220, at least one memory 230, and a network interface 240.

The database 210 can be located in a storage. The term "storage" may refer to any device or material from which information may be capable of being accessed, reproduced, and/or held in an electromagnetic or optical form for access by a computer processor. A storage may be, for example, volatile memory such as RAM, non-volatile memory, which permanently hold digital data until purposely erased, such as flash memory, magnetic devices such as hard disk drives, and optical media such as a CD, DVD, Blu-ray disc, cloud storage, or the like.

A database of 3D torso images of breast reconstruction patients and volunteers and demographic data (e.g., age, BMI, race, previous surgeries, diagnosis, etc.) may be used. The database may also include a non-limiting list of, breast size, breast shape, breast feeding, gravidity and parity, and medical history. The patients may consist of those who underwent autologous reconstruction (TRAM flap, latissimus dorsi flap (LD), and deep inferior epigastric perforators (DIEP) flap) and implant-based reconstruction (saline or silicone implants). They may have also received additional procedures, such as mastopexy (for symmetry with the reconstructed breast and reducing ptosis), fat grafting, tissue expander placement, and nipple reconstruction. Tissue expanders, or temporary saline implants, are sometimes used to slowly stretch the skin and pectoralis muscle (large chest muscle). They may be later replaced with tissue or a permanent implant. Within the database, the average age of the patients was 49.9±10.3 years (range: 24 to 75), and BMI was 28.0±5.5 (range: 18.1 to 69.8). During imaging, patients may be generally in a standing position with their hands on their hips. Images may be taken, typically but not consistently, at three-month intervals (for up to a period of two years) during the reconstructive process. Some, but not all, patients may have had a preoperative image.

Figure 4A:
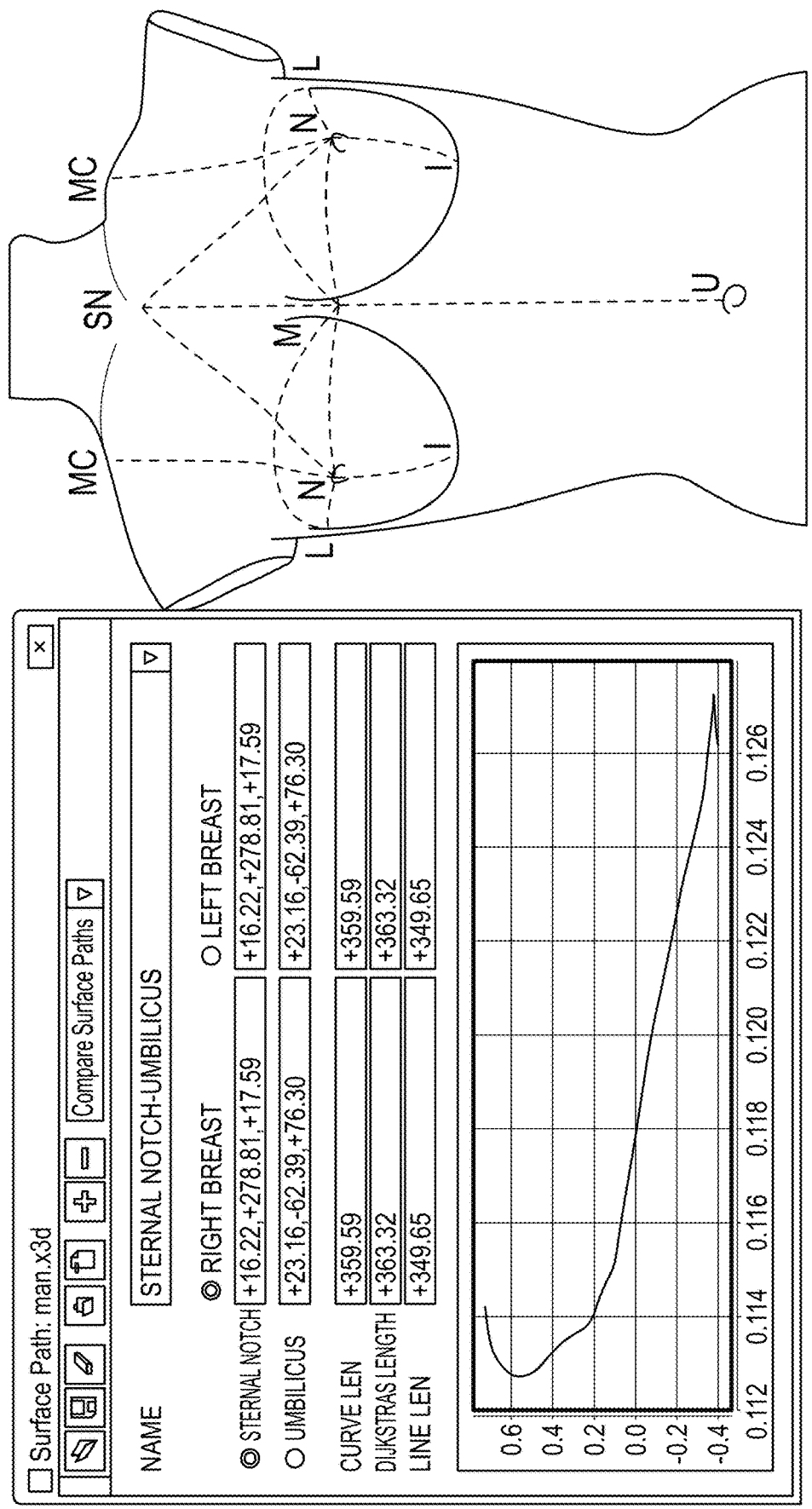
FIG. 4A is an image of linear and contour distances, in accordance with aspects of the present disclosure.
Figure 4B:
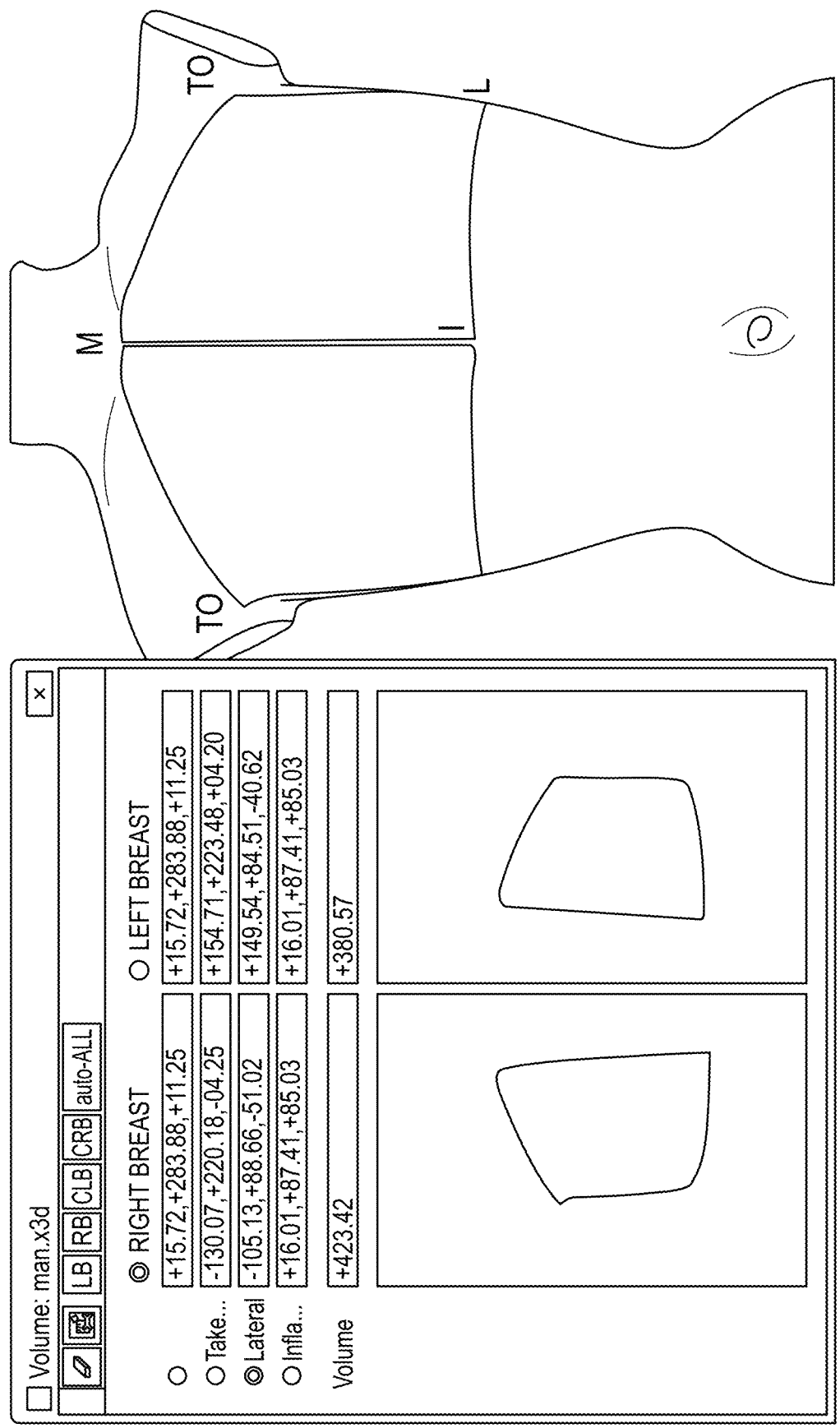
FIG. 4B is a diagram of volume measurements in customized software, in accordance with aspects of the present disclosure.

Referring to FIGS. 4A-B, a Java-based visualization and analysis tool (customized software), may be used to manipulate 3D images of the female torso (translate, rotate, scale, and crop), manually mark fiducial points, such as the sternal notch, nipples, lateral points, inframammary fold (IMF) points, midline point, transition points, and umbilicus, and extract linear, contour, and volume measurements. Customized software may be used to align the images in the xyz coordinate space, manually mark fiducial points, and calculate breast volumes. FIG. 4A is an example image of customized software showing linear and contour distances. FIG. 4B is an example image of customized software showing volume measurements of a front female torso.

As the number of cosmetic and reconstructive breast surgeries performed has been steadily increasing over the years, there is a greater need for improved technologies, such as developing a computational three-dimensional breast model. A breast model for simulating, evaluating, and interactively adjusting breast shape will be a tool for surgeons in surgical planning and for clinical consultations with patients in shared decision making.

Breast models may be used to predict breast deformations subject to various gravitational positions. For example, breast surgical procedures are typically performed on a patient lying down, but the patient may have to be moved into an upright position a number of times for the surgeon to assess the shape of the breast. Breast models may also be used to predict breast deformation due to compression from different imaging modalities in order to view the breasts in an uncompressed state or to register images. For example, in diagnostic imaging, mammograms show two-dimensional projections of the compressed breast while MRI shows three-dimensional images of the breast in the prone position. Registering the two types of images may assist radiologists in multimodal diagnosis and help in localizing structures, such as tumors. Other reasons for breast simulation models may include planning and rehearsing surgeries, predicting outcomes, and testing new methods and techniques.

Conversely, very few parametric breast models have been proposed. For example, a parametric breast model proposed by Chen, may be used either to create a breast model or fit a model to breast data. They initially create an asymmetric superquadric and then perform five global deformations to model five major features of breast shape.

Referring to FIGS. 5A-G, these five global deformations/features are called lower pole deformation, upper pole deformation, horizontal deviation deformation, medial deformation, and axillary tail deformation. FIG. 5A and FIG. 5B show the front and side views of a breast model without any deformations applied. FIG. 5C shows a front view example of lower pole deformation, which models breast sagging. FIG. 5D is a side view example of upper pole deformation, which controls the slope and curvature of the upper half of the breast. In FIG. 5E, a front view example is shown of horizontal deviation deformation, which controls the turn of the breast whether to the right and left. FIG. 5F is a front view example of medial deformation, which flattens out the sides of the breast. FIG. 5G is a front view example of axillary tail deformation, which adjusts the top half of the breast to point toward the shoulder. The 17 parameters that control the breast size and shape can be used to quantitatively analyze the degrees of key shape variables of the breast. However, Chen's model had limited capability in accurately fitting to breast data due to its basic design. Breasts contain many different curves and shape features that an asymmetric superquadric and five global deformations is unable to fully capture. Still, due to the strict control of breast shape and size through the 17 parameters, it is helpful to simulate different elliptical models to evaluate the parameters of the disclosed spherical harmonic model and correlate the parameters to clinically relevant parameters, such as breast height, width, depth, and ptosis. The modeling technique that is introduced in this disclosure may allow for computing the breast shape "distance" based on coefficients, and the coefficients can be related to specific breast shapes. The breast shapes may include for example, reduction mammoplasty, reduction mastopexy, augmentation mammoplasty, augmentation mastopexy, and/or correction of any breast shape deformities, based on spherical harmonic coefficients.

The disclosed method allows for modeling the original breast shape (accuracy of fitted model), can be used to modify breast shape (shape modulation), establishes correspondence between different breast shapes and sizes (cross model alignment), can be used to compute shape distance between different breasts (parametric shape comparison), and can be used to predict breast shapes.

Surgeons may evaluate breast shape by taking measurements in person using a tape measure in the clinic or using rulers on standard photographs of the frontal and lateral views. These measurements include the linear distance between fiducial points, including the sternal notch, nipples, lateral points, mid-clavicle points, midline, and inframammary fold. Another measurement to describe breast shape is ptosis, which is used to describe sagging of the breasts. The inframammary fold is often designated as a reference point for evaluating the degree of ptosis. However, grading ptotic breasts can be difficult as the inframammary fold is hidden when the woman is standing in an upright position. Using a modified Regnault's classification of ptosis, the breasts may be assigned a grade ranging from 0 to 3, where Grade 0 represents no ptosis and Grade 3 represents extreme ptosis. One of skill in the art would know what Regnault's classification is and how to implement it. With the advent of three-dimensional imaging technology, additional objective measurements, such as surface contours and curvature, surface area, volume, and even ptosis can now be quantitatively assessed.

In the illustrated embodiment, the SPHARM modeling method was first tested on three-dimensional preoperative torso surface images of a number of women scheduled to undergo mastectomy for the treatment or prevention of breast cancer and other abnormalities. None of them have previous breast surgeries but may have had a biopsy that did not affect the breast appearance as determined by an experienced plastic surgeon. Patients with rare congenital breast abnormalities, previous radiation therapy, or previous major breast surgeries were excluded.

Referring to FIGS. 6A-E, tables of patient demographics, clinical characteristics of the patients' breasts, patient variables, procedure types, and the procedures underwent are shown. FIG. 6A is a table of the percentages of the patient demographics and characteristics describing the age, BMI, tumor size, race, ethnicity, diagnosis and number treated with pre-operative chemotherapy. FIG. 6B is a table of the baseline clinical characteristics of breasts (N=76) for the 73 cancer patients, describing the percentage of the various tumor types and the positions of the tumors. FIG. 6C is a table of the demographics of 32 patients who underwent TRAM flap and/or implant reconstruction. FIG. 6D is a table of the procedure used for each breast. FIG. 6E is a table of the patient demographics at the time of their preoperative image.

In various embodiments, three-dimensional breast images of patients who underwent unilateral or bilateral TRAM flap and/or implant reconstruction were selected, and SPHARM models were generated from the images. The generated SPHARM models of the reconstructed breasts were classified using standard classification methods: k-nearest neighbor, Naïve Bayes, and quadratic discriminant analysis. In various embodiments, a dataset consisting of a number of patients, including their preoperative and corresponding postoperative images, was created for testing predictive modelling. For the preoperative image set and the postoperative image set, a number of SPHARM models were generated for each set.

In various embodiments, the breasts may be extracted from the torso images by identifying the borders of each breast. In various embodiments, the fiducial locations at the top, bottom, left, and right sides of each breast that would delineate how the breast would be segmented from the torso images may be identified. Before identifying these fiducial locations, the images had to be manually aligned so that the height of a patient from head to foot aligned with the y axis, the width from the right shoulder to the left shoulder aligned with the x axis, and the body faced the positive z direction. Then four fiducial locations were found along the border of each breast from the 3D torso image (FIG. 9A). Two locations were automatically detected: the midline point and inframammary fold. The other two locations, the transition point and the lateral point, may be manually selected. These points may be manually selected as the breast is usually relatively smooth in these regions.

Referring to FIGS. 7A-E, the graphical models of the breasts may be made by finding the number of vertices along the x and y axes (7A-B) and the midline point (7C-E) to show the inframammary folds (7F). Manual fiducial point selection may be conducted in customized software (a customized Java-based visualization tool), and the automatically detected points may be found using code developed in MATLAB 2015a. To automatically locate the midline point, the head, arms, and the torso below the breasts may be cropped out first. The head and arms contained less points than the torso, and the number of points peaked on the sides of the torso. Therefore, using a histogram of the number of points along the width of the torso in bins of 20 millimeters, the left and right borders of the torso may be determined as shown in FIG. 7A. Using this same concept, another histogram may be generated measuring the number of vertices along the y direction in bins of 20 millimeters to determine the top cutoff point as shown in FIG. 7B, where the neck was found to have fewer points relative to the torso. To set the bottom cutoff point, the surface normal in the vertical y direction (corresponding to height) of the mesh vertices may be used to find the lowest visible point of the breasts. The vertices with surface normal within 18.2° (acos(0.95)) of the negative y direction were sub-selected. Then the vertex with the lowest y value was designated as the lowest visible point of the breast and was used as the bottom cutoff point. If there were no valid vertices with a y surface normal within 18.2° (acos(0.95)) of the negative y direction, excluding the nipple, then the bottom cutoff point was set to 33 centimeters below the top cutoff point. It may be determined that the breasts were within 33 centimeters from the top cutoff point. This mostly occurred for relatively small, non-ptotic breasts. Then Gaussian curvature was computed on the remaining mesh contained within the designated borders as shown in FIG. 7C. The area between the breasts, where the midline point is, has negative curvature (concave), while the breasts themselves have positive curvature (convex). The points with negative curvature between the two nipples, or most projecting points on the left and right halves of the torso, were selected as possible midline points. The midline point is not more than 10 mm below the most projecting points. Then the selected points were separated into 5 mm bins along the y direction, and the width (x range) of each bin was found, as shown in FIG. 7D. The bin with the smallest width was selected and its midpoint was designated as the midline point, shown as a blue star in FIG. 7E. Next, using a contour detection algorithm, which also utilizes Gaussian curvature, points may be estimated along the IMF (inferior breast-chest contour) of the left and right breasts. The red line in FIG. 7F delineates the estimated IMF. The partial torso image in FIG. 7F is colored by the shape index for each vertex in the mesh, which was calculated from the contour detection algorithm. The IMF was detected by following the negative curvature path along the underside of the breast. However, for breasts with prominent nipples that have significant negative curvature along the underside of the nipple, the algorithm selected the underside of the nipple as the inframammary fold, hence providing incorrect fiducial points. In order to avoid selecting these incorrect fiducial points, the algorithm was modified to ignore the curvature values of the nipple area. The nipple area was experimentally determined to be within 2.5 centimeters of the most projected points along the z axis on the left and right half of the torso. The nipple diameter for women aged 20-64 years may range from for example, 1 cm to 2.75 cm.

Figure 8:
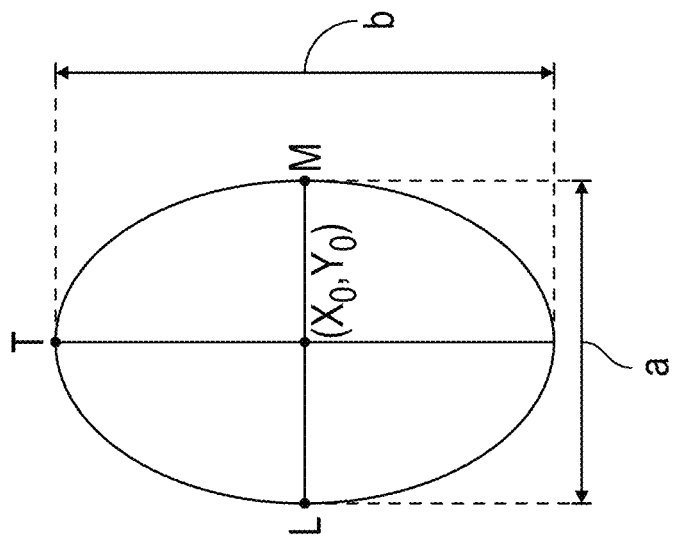
FIG. 8 is a diagram defining ellipse formulas, in accordance with aspects of the present disclosure.

Referring to FIG. 8, in various embodiments, to define the upper border of each breast, the ellipse formula (using only x and y coordinates assuming that the x axis aligns with the width of the breast and the y axis aligns with the breast height):

$$\frac{(x-x_0)^2}{a^2} + \frac{(y-y_0)^2}{b^2} = 1,$$

was used to locate intermediate points between the lateral point (L) and the transition point (TP), and for connecting the midline point (M) and the TP.

FIGS. 9A-C are diagrams of breast cropping, in accordance with aspects of the present disclosure. Dijkstra's shortest path algorithm was used to connect all the points, defining the estimated closed border of the breast as displayed in FIG. 9B. One of skill in the art would be familiar with Dijkstra's shortest path algorithm and understand how to implement it. The white line depicts the border formed using the ellipse formula, and the black line depicts the border formed using the contour detection algorithm. Finally, FIG. 9C shows an example of two breast surface patches that were extracted from the torso image.

To identify which vertices to extract, an initial vertex was selected based on the shortest distance to the average of all the border points. Then neighboring vertices directly connected to the initial vertex and the next neighboring vertices connected those vertices may be iteratively added until the border vertices were selected in which case the iteration is stopped.

In various embodiments, SPHARM may require a genus zero surface and a relatively dense mesh to accurately model an object. Since the cropped breast was an unclosed surface patch, a method to patch the back hole in order to form a closed surface may be used. First, the cropped breast mesh may be pre-processed to clean up non-manifold vertices (i.e., edges that are shared by more than two faces and isolated pieces (disconnected vertices and edges)). Then the advancing front mesh (AFM) technique may be used to fill any small holes that were created due to the removal of the non-manifold vertices following the rules for creating triangles as shown in FIGS. 10C-E. FIG. 10C shows the rule for the condition $\theta i<90°$; FIG. 10D shows the rule for the condition when $90°\leq\theta i<150°$; and FIG. 10E shows the rule for the condition when $\theta i\geq 150$ After that, a single-mesh supplement method was used to smooth the border of the breast mesh by connecting adjacent boundary edges whose angle was less than 90°. Then the breasts may be rotated so that the height of the breast aligned with the z axis, the width aligned with the y axis, and the depth aligned with the x axis.

Figure 10A:
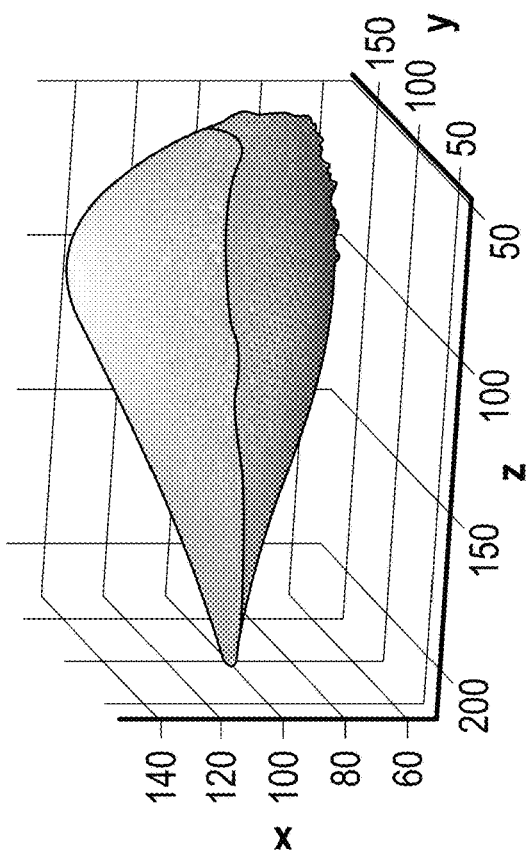
FIGS. 10A-B are graphs of the unclosed breast and back mesh (A) combined to form a closed genus-zero object (B), in accordance with aspects of the present disclosure.
Figure 10B:
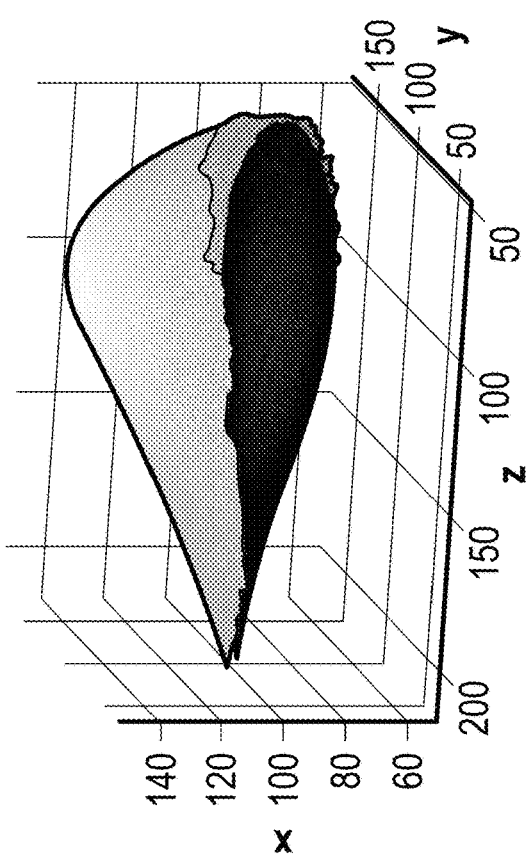
Figure 10C:
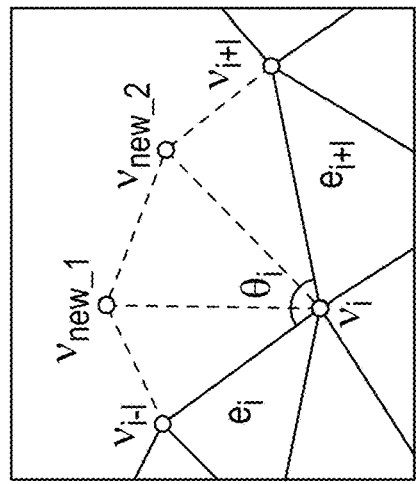
FIGS. 10C-E are diagrams of the rules for creating triangles, in accordance with aspects of the present disclosure.
Figure 10D:
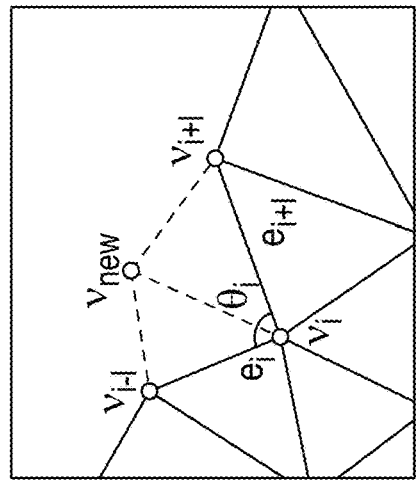
Figure 10E:
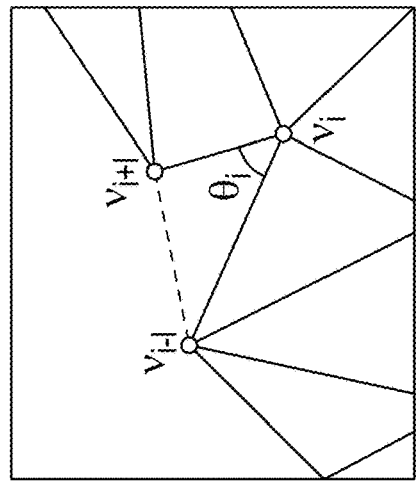

Referring to FIGS. 10A-B, graphs of the unclosed breast mesh and back mesh (A) are combined to form a closed genus-zero object (B). To patch the hole on the backside of the breast surface mesh, a 2D rectangular y-z grid of points was generated based on the size of the hole, and the points were equally spaced according to the average length between the boundary points. Then the points outside of the hole boundary may be removed. Next, Delaunay triangulation was used to connect the generated points to form a mesh. Each point was assigned an x value based on the average x value of the breast border points weighted by the 2D Euclidean distance using the y and z coordinates. Then the new mesh may be attached to the breast mesh, and the remaining gaps were filled using a hole filling algorithm based on the advancing front mesh technique as shown in FIGS. 10A-B. In various embodiments, the method may include first identifying holes in the mesh by finding boundary edges, which are edges that are not shared by two faces. Boundary edges that form a closed loop constitute a hole. Next, calculating the angle $\theta_i$ (0 to 360°) between adjacent boundary edges ($e_i$ and $e_{i+1}$) at each vertex vi. Next, finding the smallest angle $\theta_i$ and create new triangle(s) at vertex vi following the rules shown in FIGS. 10C-E. The location of the new vertices is determined by the average edge length and the shortest direction to close the gap across the two meshes. Next, computing the distance between every newly created vertex and every related boundary vertex; if the distance between them is less than the given threshold (such as the average edge length), they are merged. Next, update the front. Next, repeat until all holes are filled.

In order to obtain spherical topography and a standardized orientation of the modeled breasts, the breast image data were mapped to a specific template using spherical coordinates ($\theta$, $\phi$) as displayed in FIGS. 11A-B. To do this, each vertex in the breast mesh was bijectively mapped to the unit sphere ($\theta=[-\pi/2, \pi/2]$ and $\phi=[-\pi, \pi]$) based on certain landmarks. The nipple (or highest projecting point) was set to $\theta=\pi/2$. The breast's boundary points, at the discontinuity between the breast surface mesh and the connected back mesh, were assigned θ=0. To determine φ for each point, a straight line (CN) extending from the centroid of the breast boundary points (backside of the breast) to the nipple, or most projecting point may be generated. Each point (x, y, z) on the breast surface was then projected onto the CN line, to generate its position (y1, z1) on the line, such that x1, the x-coordinate of the point on the CN line, is equivalent to the x-coordinate of point PP. Then the angle φ can be calculated based on the (y, z) breast point coordinate and point (y1, z1) on the CN line. Following determination of φ, the set of all the points on the breast surface having the same φ, on the positive (front) side of the breast, are used to trace its angular path along the surface, and its length is determined. The relative surface distance of the point P with respect to this length is scaled by π/2 and is assigned to θ accordingly. The front side of the breast was assigned positive values for θ, and the back side was assigned negative values for θ. Also, since the surface of different objects are aligned through spherical parameterization, achieving correspondence across two different breast models is feasible, which allows for comparisons of local and global changes in breast shape and size.

SPHARM Expansion

The Fourier spherical harmonics Y(θ, φ) (or SPHARM functions) of degree l and order m can be defined by $$Y_l^m(\theta, \phi) = \sqrt{\frac{(2l+1)(l-m)!}{4\pi(l+m)!}} P_l^m(\cos\theta) e^{im\phi}$$

Where $P_l^m(\cos\theta)$ are the associated Legendre polynomials defined by the differential equation:

$$P_l^m = \frac{(-1)^m}{(2^l l!)} (1+x^2)^{m/2} \left(\frac{d^{l+m}}{dx^{l+m}}\right)(x^2 - 1)$$

The SPHARM expansion takes the form: $v(\theta, \phi) = \sum_{l=0}^{\infty} \sum_{m=-l}^{l} c_l^m Y_l^m(\theta, \phi)$.

Where $v(\theta, \phi) = (x(\theta, \phi), y(\theta, \phi), z(\theta, \phi))^T$ and $c_l^m = (c_{lx}^m, c_{ly}^m, c_{lz}^m)^T$ are the estimated SPHARM coefficients. $L_{max}$ is a user-specified degree. The function $v(\theta, \phi)$ can be independently decomposed into three functions for the three coordinates:

$$x(\theta, \phi) = \sum_{l=0}^{L_{max}} \sum_{m=-l}^{l} c_{lx}^m Y_l^m(\theta, \phi);$$

$$y(\theta, \phi) = \sum_{l=0}^{L_{max}} \sum_{m=-l}^{l} c_{ly}^m Y_l^m(\theta, \phi); \text{ and}$$

$$z(\theta, \phi) = \sum_{l=0}^{L_{max}} \sum_{m=-l}^{l} c_{lz}^m Y_l^m(\theta, \phi),$$

The function values, $x_{i,j} = Y_l^m(\theta_i, \phi_i)$ for $1 \leq i \leq n$, are inputted into a linear system for each of the three coordinate functions as follows:

$$\begin{pmatrix} y_{1,1} & y_{1,2} & \cdots & y_{1,k} \\ y_{2,1} & y_{2,2} & \cdots & y_{2,k} \\ \vdots & \vdots & & \vdots \\ y_{n,1} & y_{n,2} & \cdots & y_{n,k} \end{pmatrix} \begin{pmatrix} a_1 \\ a_2 \\ \vdots \\ a_k \end{pmatrix} = \begin{pmatrix} x_1 \\ x_2 \\ \vdots \\ x_n \end{pmatrix},$$

where $y_{i,j} = Y_l^m(\theta_i, \phi_i)$, $j = l^2 + l + m + 1$, and $k = (L_{max}+1)^2$.

Lmax is the user specified degree, degree l=0, ..., Lmax, and order m=-l, ..., 0, ..., l. Given the xyz coordinates of an object, the coefficients $(\alpha_1, \ldots, \alpha_k)^T$ can be solved for through least squares fitting. Increasing degree Lmax increases the number of coefficients and provides a more detailed reconstruction. As such, the SPHARM coefficients make up a hierarchical surface descriptor. The number of coefficients is equal to $(L_{max}+1)^2 \times 3$. These coefficients approximate the full underlying surface, which can be used to represent and reconstruct the object.

The SPHARM descriptor (or set of coefficients) was computed using SPHARM-MAT toolbox. The SPHARM-MAT toolbox includes methods to perform spherical parameterization (a different method from the parameterization discussed above), expansion, registration, and statistical analysis and other utilities. Besides inputting the breast image data to calculate the SPHARM descriptor, a degree setting needs to be given. Each additional degree increases the number of coefficients and thereby increases the level of detail as shown in FIGS. 12A-E.

To evaluate the fitting accuracy of the SPHARM model to the original breast data, the root mean square error (RMSE) between the points of the original breast data and the points of the SPHARM model via the Euclidean distance may be used. The RMSE between the original breast data points $x_1$ and the SPHA-RM model points $x_2$ is defined as $$RMSE = \sqrt{\frac{1}{n} \sum_{i=0}^{n} (x1, i - x2, i)^{\wedge}2}$$

Figure 13:
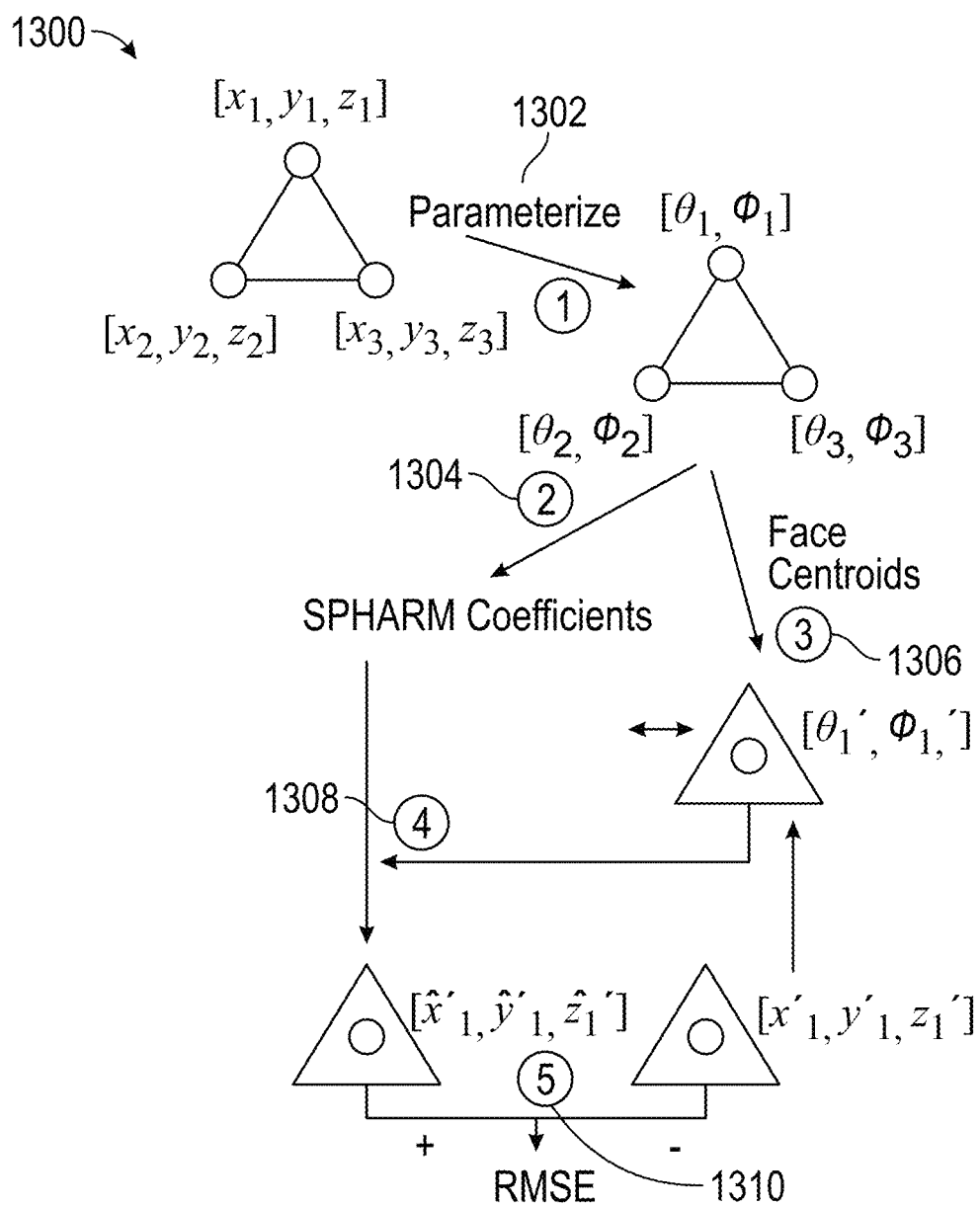
FIG. 13 is a diagram for calculating the root mean square error (RMSE), in accordance with aspects of the present disclosure.

FIG. 13 is a diagram for calculating the root mean square error (RMSE) 1300, in accordance with aspects of the present disclosure. The details of how the RMSE is computed for resampled points on the faces of the surface mesh, instead of the triangle vertices, as discussed below at step 1306. Initially at step 1302, given a closed breast object (input), the object is parameterized so that each vertex is assigned a spherical coordinate ($P_{vertices}(x, y, z) \rightarrow P_{vertices}(\theta, \phi)$). Next at step 1304, the SPHARM coefficients (output), c, are estimated by solving a linear system using the spherical harmonic equations, $Y_l^m(\theta, \phi)$, and the given vertices, $P_{vertices}(\theta, \phi), y(\theta, \phi), z(\theta, \phi)$. Next, at step 1306, since the SPHARM coefficients are fitted (or over-fitted) to the input vertices, new vertices by finding the centroid of each face in the closed breast object (input) may be used, which gives us a new set of vertices ($P_{faces}(x', y', z')$) and the corresponding parameterized spherical coordinates ($P_{faces}(\theta', \phi')$). Next at step 1308, $P_{faces}((x'\theta, \phi), y(\theta, \phi), z(\theta, \phi))$ is estimated using the SPHARM coefficients from step 2 and the spherical coordinates $P_{faces}(\theta', \phi')$, $$P_{faces}^{\wedge}(x', y', z') = \sum_{l=0}^{LMax} \sum_{m=-l}^{l} c_l^m - Y_l^m(\theta, \phi').$$

Next at step 1310, calculate the RMSE between $P_{faces}(x', y', z')$ and $P^{\wedge}_{faces}(x', y', z')$.

The SPHARM coefficients can be used to determine shape similarity between objects, such as between preoperative and postoperative breasts, left and right breasts, and the breasts of different patients using a similarity measure called root mean square distance (RMSD). The RMSD for the coefficients is:

$$RMSD = \sqrt{\frac{1}{4\pi} \sum_{l=0}^{L_{max}} \sum_{m=-l}^{l} \|c_{1,l}^m - c_{2,l}^m\|^2}$$

Where $c_{1,i}^m$ and $c_{2,i}^m$ are SPHARM coefficients of the breast shapes being compared.

For set of patients' pre-op breast images whose post-op shapes are known, the SPHARM coefficients of each breast are computed. Let $x=[x_1, x_2, \ldots, x_{1320}]^T$ be the spherical coefficients obtained from modeling breast at pre-op (P1) and $y=[y_1, y_2, \ldots, y_{1320}]^T$ be the SPHARM coefficients for the post-op (P2) breast. Solving for linear least squares optimization, a set of weights that determine the contribution of each coefficient to the overall breast shape are obtained. A and B are diagonal matrices with x and y as their respective diagonals. W is solved for using least squares optimization to determine the transformation vector:

$$\beta = [\beta_1 \beta_2 \ldots \beta_{1319} \beta_{1320}]^T.$$

$$AW = B$$

Where, $$A = \begin{bmatrix} x_1 & \cdots & 0 \\ \vdots & \ddots & \vdots \\ 0 & \cdots & x_{1320} \end{bmatrix}, B = \begin{bmatrix} y_1 & \cdots & 0 \\ \vdots & \ddots & \vdots \\ 0 & \cdots & y_{1320} \end{bmatrix}, W = \begin{bmatrix} \beta_1 & \cdots & 0 \\ \vdots & \ddots & \vdots \\ 0 & \cdots & \beta_{1320} \end{bmatrix}$$

Least squares optimization fits the given linear model to find the weight vector $\beta$ such that error is minimized.

$$\min/\beta \|AW - B\|^2$$

Figure 57A:
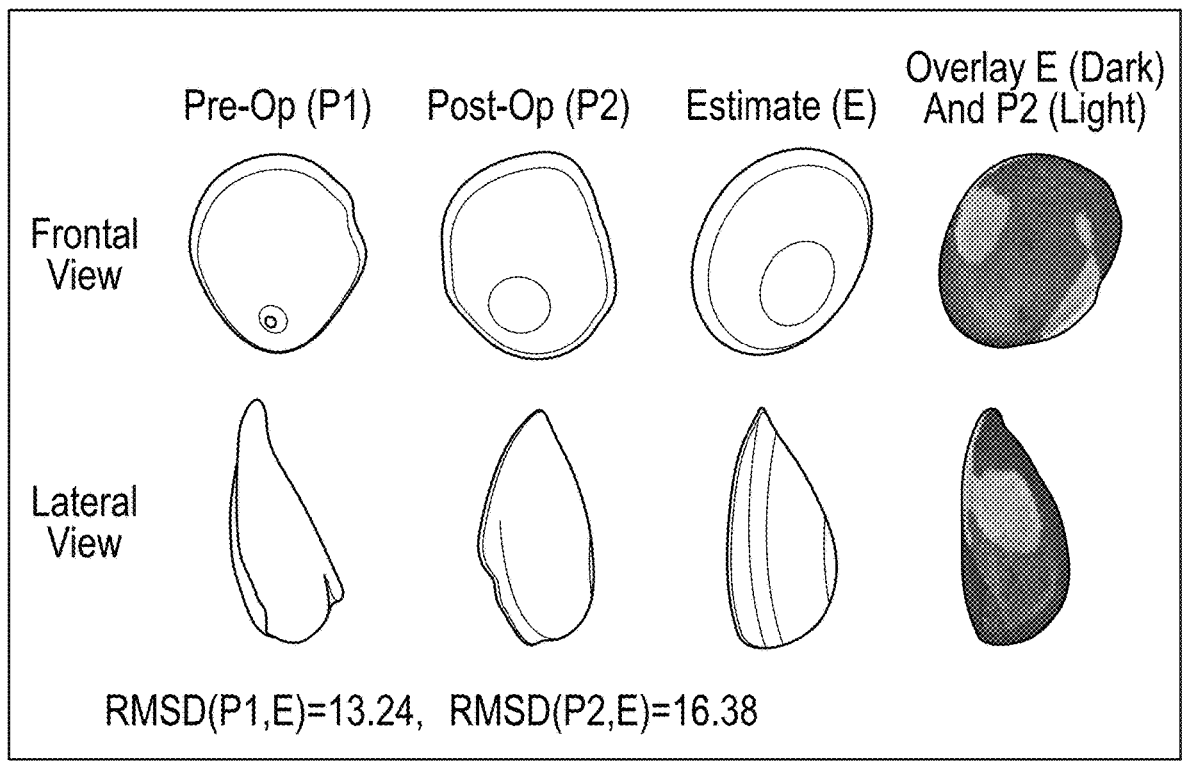
FIG. 57A-D are images of pre-op (P1), post-op (P2), estimate (E) and overlay of estimate on the post-op breast, in accordance with aspects of the present disclosure.
Figure 57B:
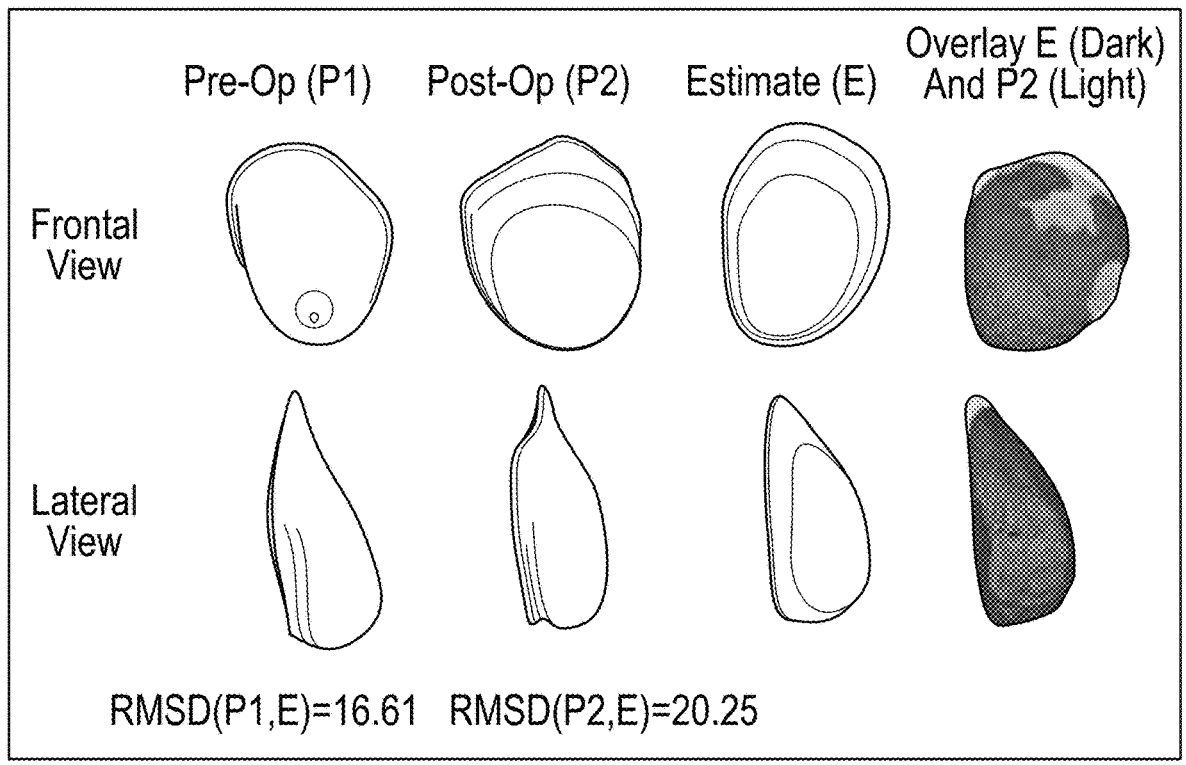
Figure 57C:
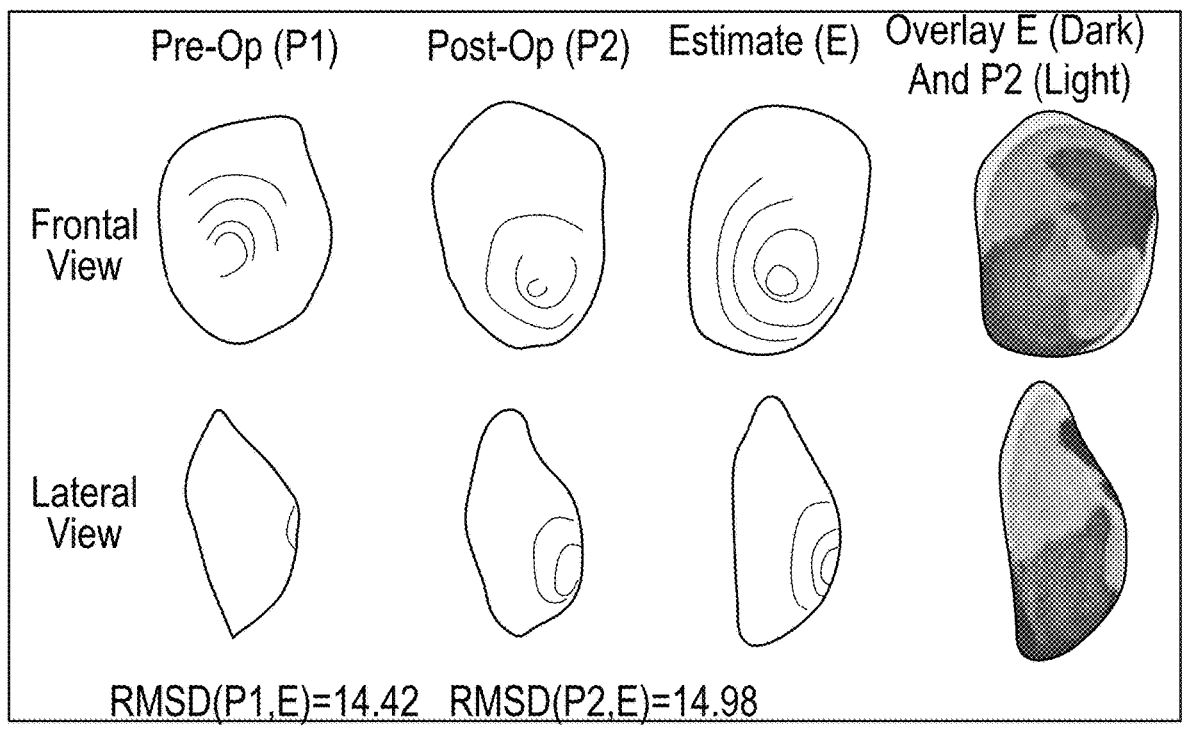
Figure 57D:
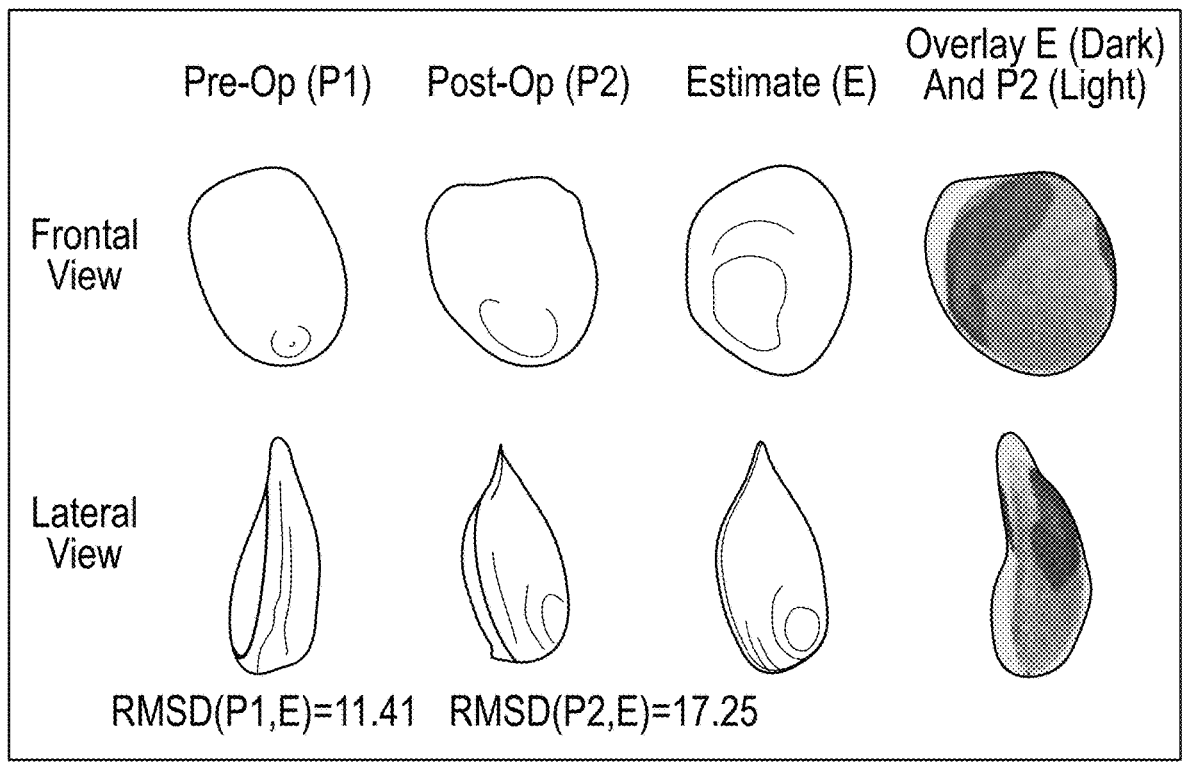

The estimated weight vector $\beta$ is the transformation that when applied to x, results in y. Thus, when the transformation vector $\beta$ is known, it can be applied to the SPHARM coefficients of the pre-op breasts to obtain its post-op shape coefficients. To validate this hypothesis, SPHARM models for pre-op (P1) and their corresponding post-op (P2) breast image pairs of individual patients who have undergone different cosmetic surgical procedures (reduction, augmentation and mastopexy) are generated (see FIGS. 57A-C). The weight vector $\beta$ obtained from least squares optimization to the P1 breast coefficients is applied. This results in transformed P1 which is an estimate of the post-op breast shape P2, as demonstrated by the nearly zero RMSD values (see FIG. 56).

The squared spherical harmonic basis functions integrate to $4\pi$ instead of 1, so a correction is added. The difference between the root mean square error (RMSE) and the RMSD is that the RMSE is computed in the spatial domain while the RMSD is computed in the frequency domain. Their values are similar to each other if comparing the same two objects. While the RMSD is relatively simple to compute from the coefficients themselves, other error measures (e.g., the mean absolute distance and other distance measures) that depend on the points should use a uniform sampling of the spherical parameterization, such as the iterative icosahedron subdivision.

The Hausdorff distance, $d_H(A, B)$, is the maximum distance of points in Set A to the nearest point in Set B and points in Set B to the nearest point in Set A. It is formally defined as:

$$d_H(A, B) = \max\left\{\sup_{a \in A} \inf_{b \in B} d(a, b), \sup_{b \in B} \inf_{a \in A} d(a, b)\right\},$$

where a and b are points of sets A and B, respectively, $d(a, b)$ is the Euclidean distance between points a and b, sup is the supremum, and inf is the infimum. This measure is used to evaluate if there is any point in one object that is distant from the points of another object and vice versa.

The SPHARM coefficients contain both size and shape information, hence the computed mean squared distance reflects differences in both parameters. While the object can be normalized to remove the effect of scale, in the case of breasts, size may be of interest since gravity plays a role in breast shape, especially for large breast sizes.

Figure 47:
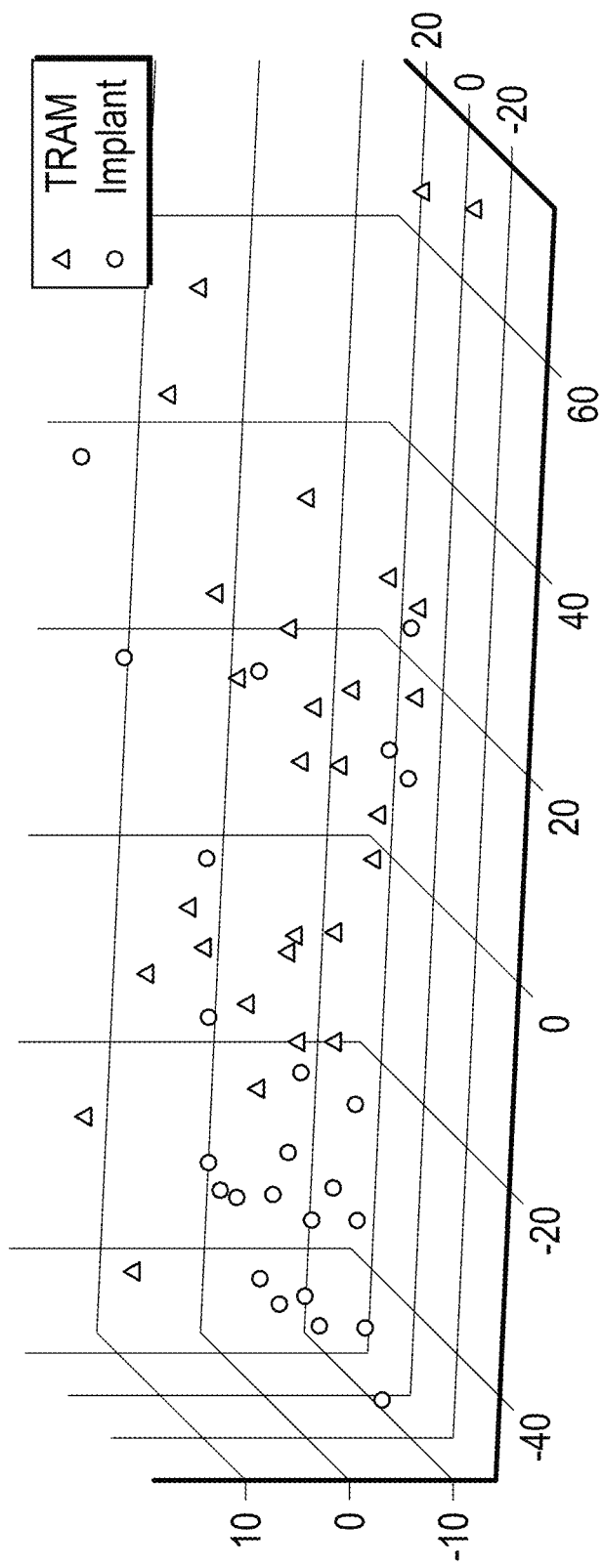
FIG. 47 is a scatterplot of the first three principal components for TRAM flap and implant reconstructed breasts, in accordance with aspects of the present disclosure.

Referring to FIG. 47, a scatterplot of the first three principal components for TRAM flap and implant reconstructed breasts is shown. Principal component analysis is a well-established dimensionality reduction technique that transforms a set of observations with d number of variables such that the first principal component contains the largest possible variance, and each succeeding principal component contains the next largest variance until all the variance is accounted for. The principal components are orthogonal to one another, and the total number of unique principal components may be less than the number of variables. To perform principal component analysis, the mean of each variable is subtracted to center the data. Then the d×d covariance matrix $\Sigma$ is computed from the centered data. The eigenvalues and eigenvectors are computed from the covariance matrix, and the eigenvalues are sorted in a descending order along with their corresponding eigenvectors. The centered data is transformed using the sorted eigenvectors. The first k principal components that explains 95% of the variance can be used for classification tasks.

Classification was performed to evaluate whether the SPHARM coefficients can differentiate breasts that have undergone different reconstruction procedures, such as TRAM flap and implant reconstructions. Three classifiers were used: k-nearest nearest algorithm, quadratic discriminant analysis, and Naïve Bayes. They are described as follows.

The k-nearest neighbor (k-NN) algorithm is a simple nonparametric method for assigning a class label to an object based on the class labels of its k closest neighbors. Unlike decision trees and linear discriminants, k-NN does not require the explicit construction of a feature space. Theoretically, as the sample size tends to infinity, the error rate of k-NN, under very mild conditions, tends to the Bayes optimal. The setting k is a user-defined constant that determines how a test point is classified based on the most frequent label among the k nearest training points using the Euclidean distance. Essentially, the sample's predicted label $R_l$ is $C_i$ if the majority of the k nearest neighbors belong to $C_i$, $$S_i = C_i \text{ if } (C_i/k > C_j/k).$$

Quadratic discriminant analysis uses a quadratic decision surface to separate k classes. QDA is much like linear discriminant analysis, except that it assumes that the covariance matrix, $\Sigma k$, is not identical, so the quadratic terms cannot be removed. The variables X are assumed to be normally distributed for each class. The quadratic discriminant function is:

$$\delta_k(x) = -\frac{1}{2}\log\left|\sum k\right| - \frac{1}{2}(x - \mu_k)^T \sum{}^{-1}(x - \mu_k) + \log \pi_k,$$

where $\delta_k(x)$ is the estimated discriminant that the observation will be in the kth class within the response variable given the predictor variables x, $\Sigma k$ is the covariance matrix, and $\pi_k$ is the prior probability that an observation belongs to the kth class. The observation is assigned to the kth class depending on the largest discriminant score.

Naïve Bayes classifiers assume that variables ($x=(x_1, \ldots, x_n)$) are independent of one another. Each variable $x_i$ contributes independently to the probability that an observation belongs to the kth class regardless of any correlations between different variables. The probability that an observation belongs to a class is given by $$p(C_k \mid x) = \frac{p(C_k)p(x \mid C_k)}{p(x)}.$$

Using the naïve independence assumption that $$p(x_i \mid C_k, x_1, \ldots, x_i+1, \ldots, x_n) = p(x_i \mid C_k),$$

for all θ, then the equation simplifies to:

$$p(C_k \mid x) = \frac{p(C_k)\prod_{i=1}^{n} p(x_i \mid C_k)}{p(x)}.$$

Since (x) is constant given the input, the following classification rule may be used:

$$\hat{C}_k = \underset{C_k}{\mathrm{argmax}}\, p(C_k)\prod_{i=1}^{n} p(x_i \mid C_k).$$

An extension of Naïve Bayes for real-valued attributes is the Gaussian Naïve Bayes, which assumes that the variables of each class are normally distributed. The likelihood of the variables assumes a Gaussian distribution:

$$p(x_i \mid C_k) = \frac{1}{\sqrt{2\pi\sigma_y^2}}\exp\left(-\frac{(x_i - \mu_{C_k})^2}{2\sigma_{C_k}^2}\right).$$

Figure 14:
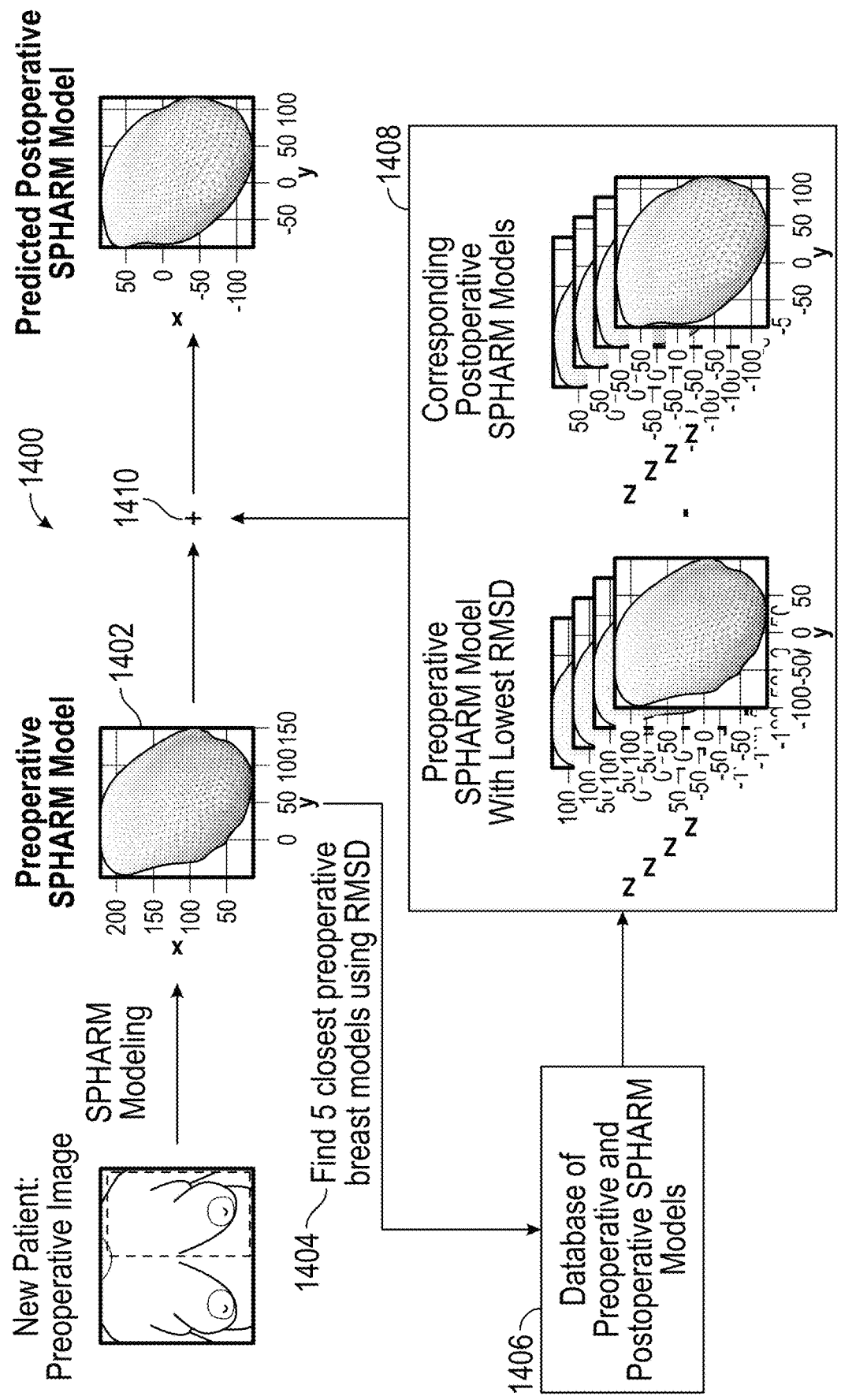
FIG. 14 is a diagram of predicting breast outcomes using the average of five models, in accordance with aspects of the present disclosure.

The SPHARM models were tested to determine their applicability for predicting breast shape after reconstruction based on exemplar data. This way if a new breast cancer patient comes in for a consultation with her surgeon to undergo reconstruction, the surgeon can show her a possible reconstruction outcome that is personalized (that is, she can be shown her predicted reconstructed breast using her own pre-operative image), which may help in the decision making process. A diagram of the example-based prediction method 1400 is shown in FIG. 14. The procedure is as follows: First, at step 1402, input the SPHARM breast model. Next, at step 1404, find the five closest preoperative breast models in the database based on the RMSD value and create an average preoperative breast model. Next, at step 1406, obtain the five corresponding postoperative breast models and create an average postoperative breast model. Next, at step 1408, calculate the coefficient differences between the average preoperative breast model and the average postoperative breast model. Next, at step 1410, add the coefficient differences to the input SPHARM breast model to simulate the predicted breast shape.

Figure 15:
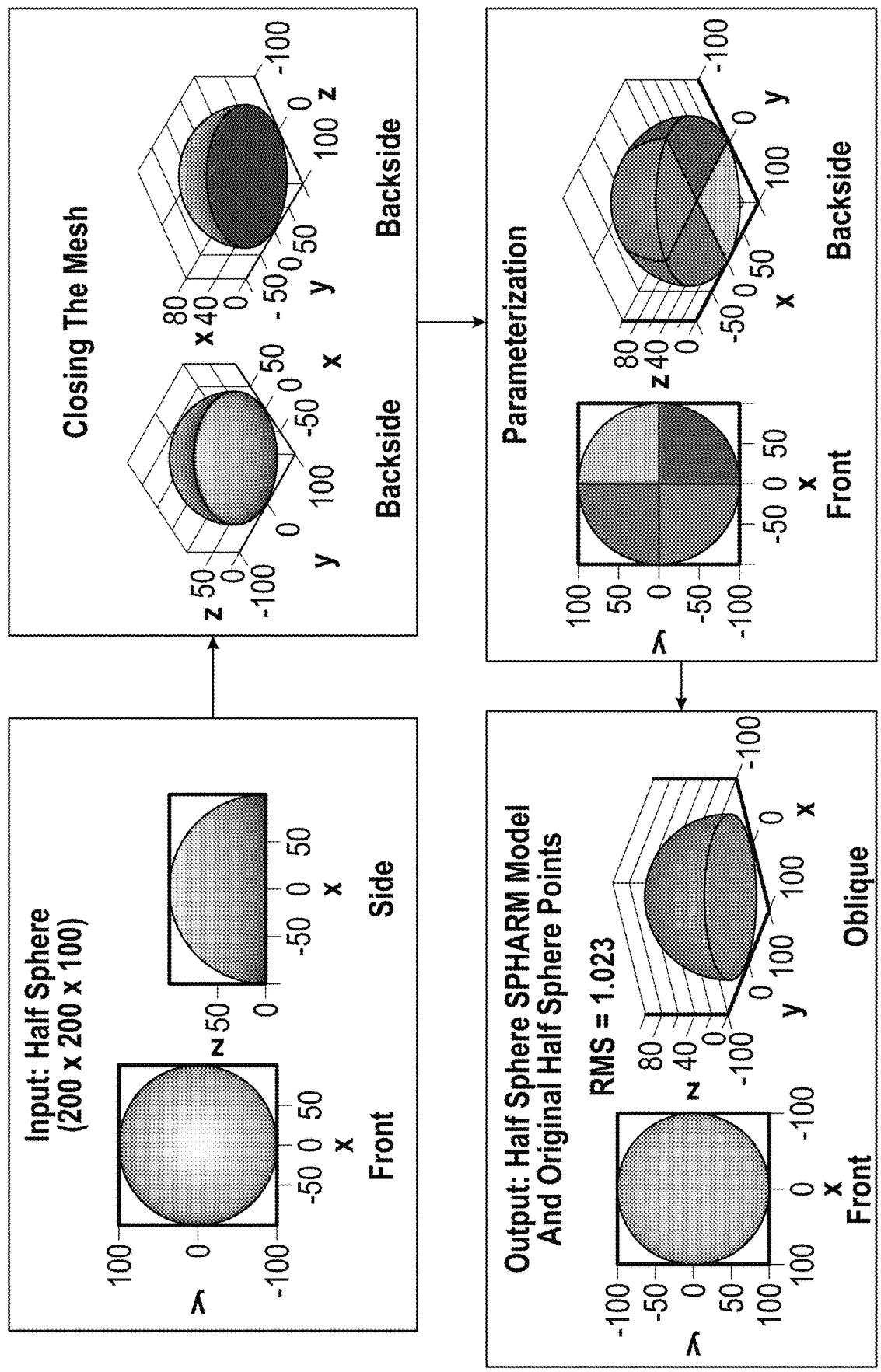
FIG. 15 is a diagram of a half sphere conversion to a SPHARM model, in accordance with aspects of the present disclosure.

The breast modeling method was tested on a half sphere (200×200×100) with an open back. As shown in FIG. 15, the half sphere successfully converted to a SPHARM model using the method described in above. The algorithm closed the hole on the backside of the half sphere and parameterized the closed half sphere, and the SPHARM coefficients was calculated using SPHARM-MAT. The root-mean-squared error between the original half sphere points and the reconstructed half sphere points from the SPHARM coefficients was 1.023.

Figure 16C:
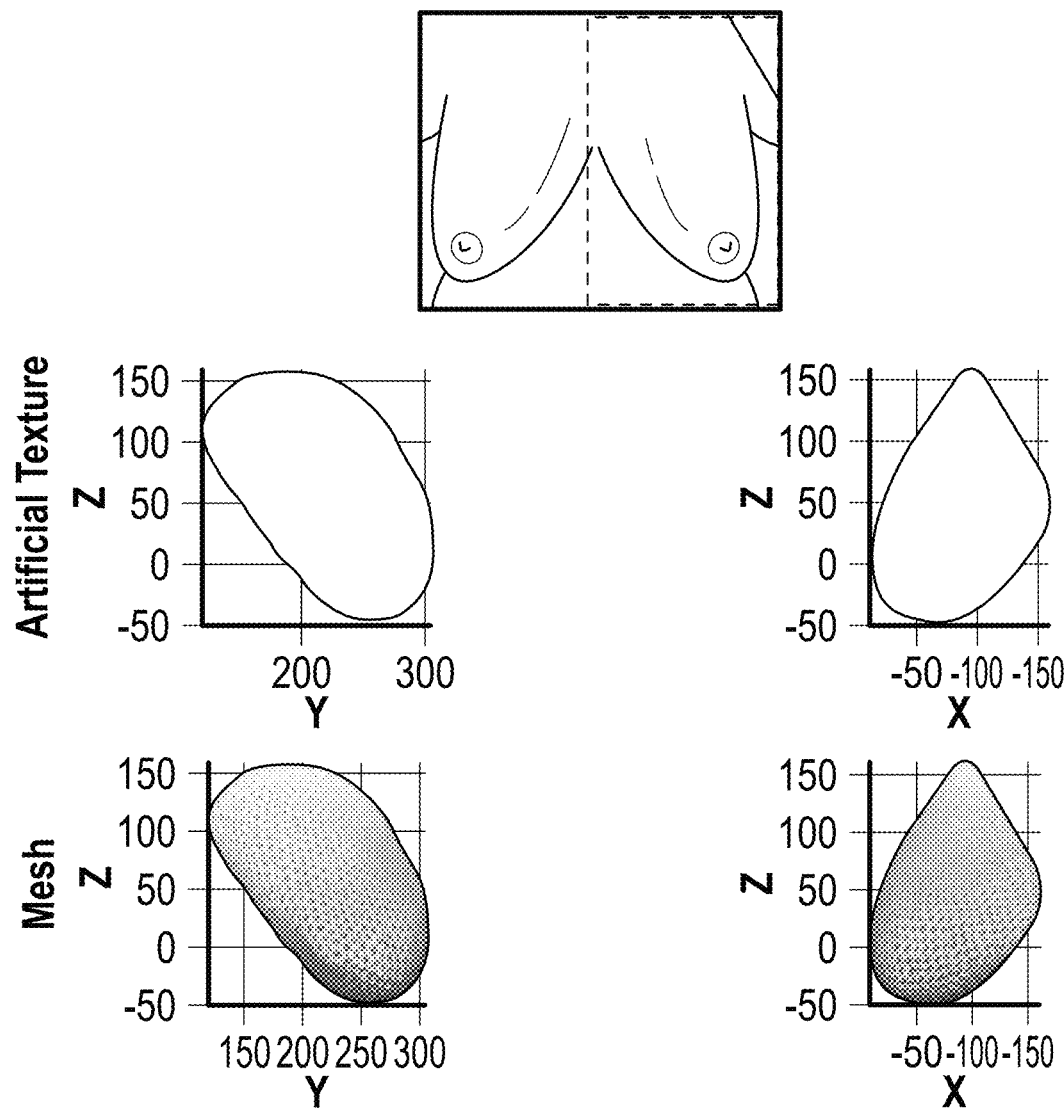

Next, the breast modeling method as described in the sections above was tested on real breast data. The results are shown in FIGS. 16A-C. The real texture or an artificial texture can be applied to the breast model. FIGS. 16A-C are SPHARM models of a small, a medium, and a large breast.

Figure 17:
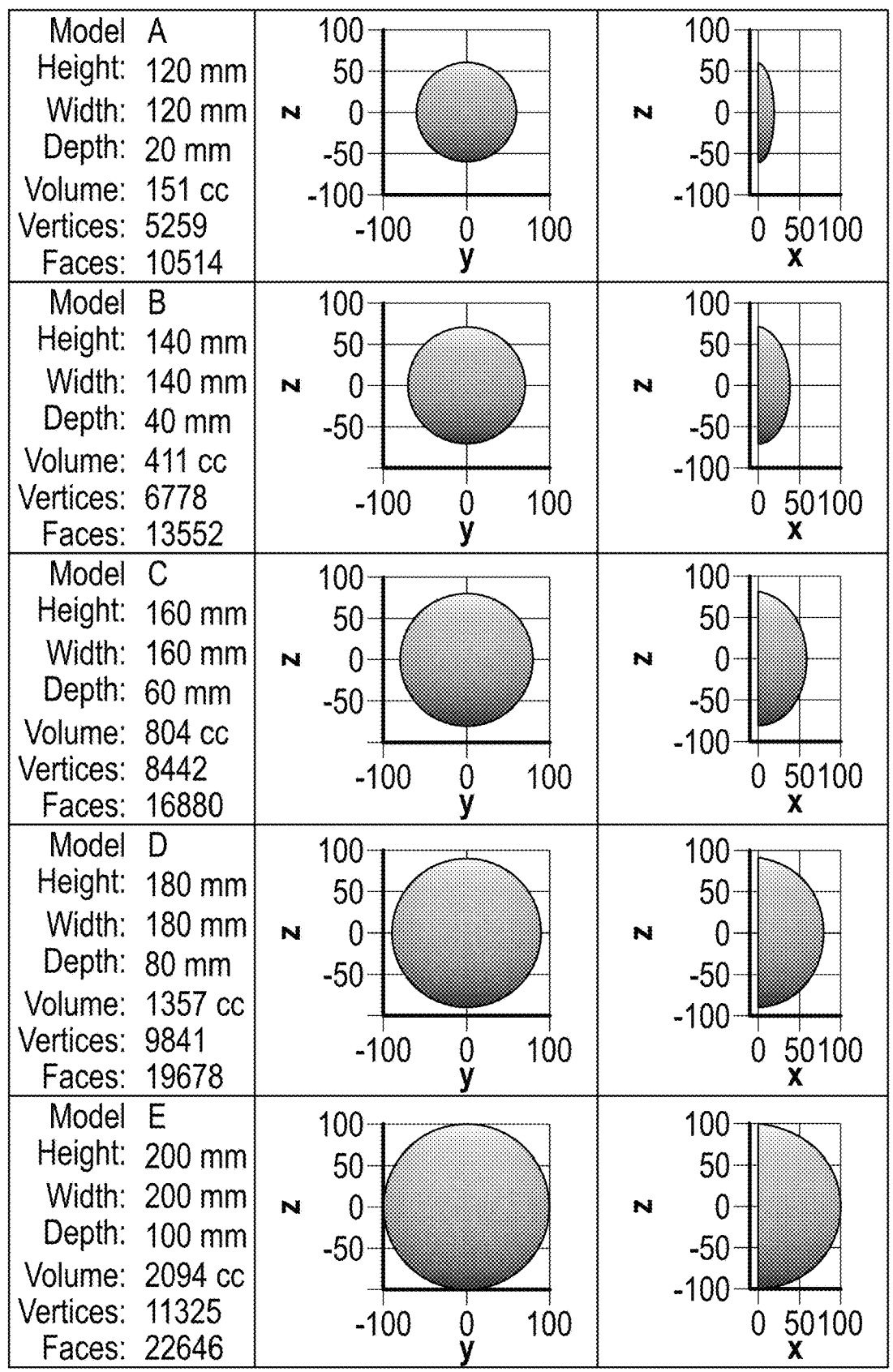
FIG. 17 is a table of synthetic models generated using different parameters, in accordance with aspects of the present disclosure.

The evaluation metrics were validated on synthetic half elliptical models. The parameters of the synthetic models were based on a number of SPHARM models that were generated from a dataset consisting of a number of preoperative images of patients. The height, width, and depth of the SPHARM models and their proportionality to one another as well as the number of vertices and faces are summarized in FIG. 18A. The generated SPHARM models are shown in FIG. 17. FIG. 17 is a table of synthetic models generated using different parameters. The RMSD, RMSE, and Hausdorff distance between the models are shown in FIG. 18B, FIG. 19A, and FIG. 19B, respectively. For each increment of 20 mm in height, width, and depth between the models, the RMSD and RMSE increased by approximately 10 mm, which is half of the increment value since most of the changes occurred only on the front side of the half sphere. The back side remained in place. The Hausdorff distance matched the increment value.

Figure 20A:
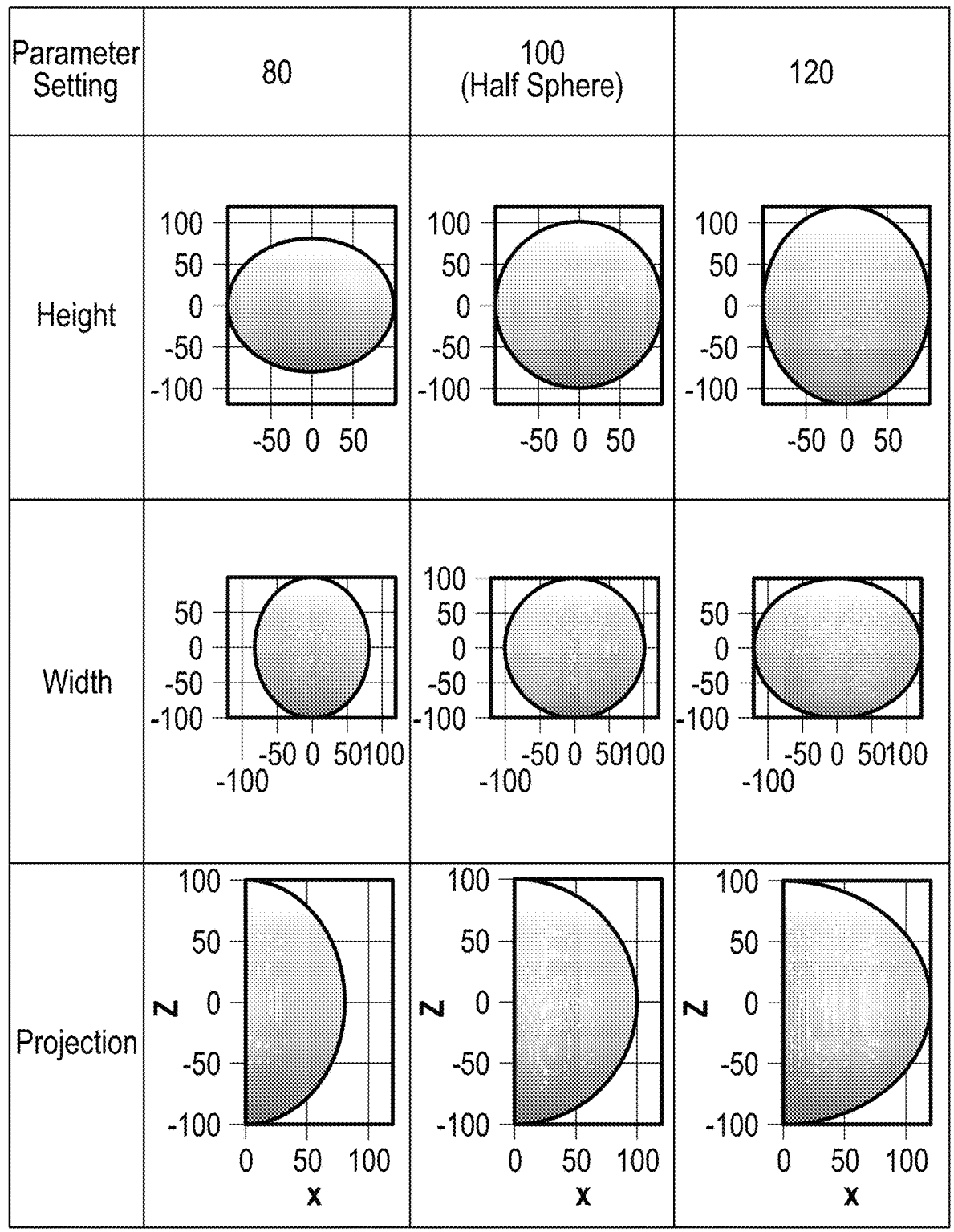
FIG. 20A is a table of different height, width, and projection parameter settings, in accordance with aspects of the present disclosure.
Figure 20B:
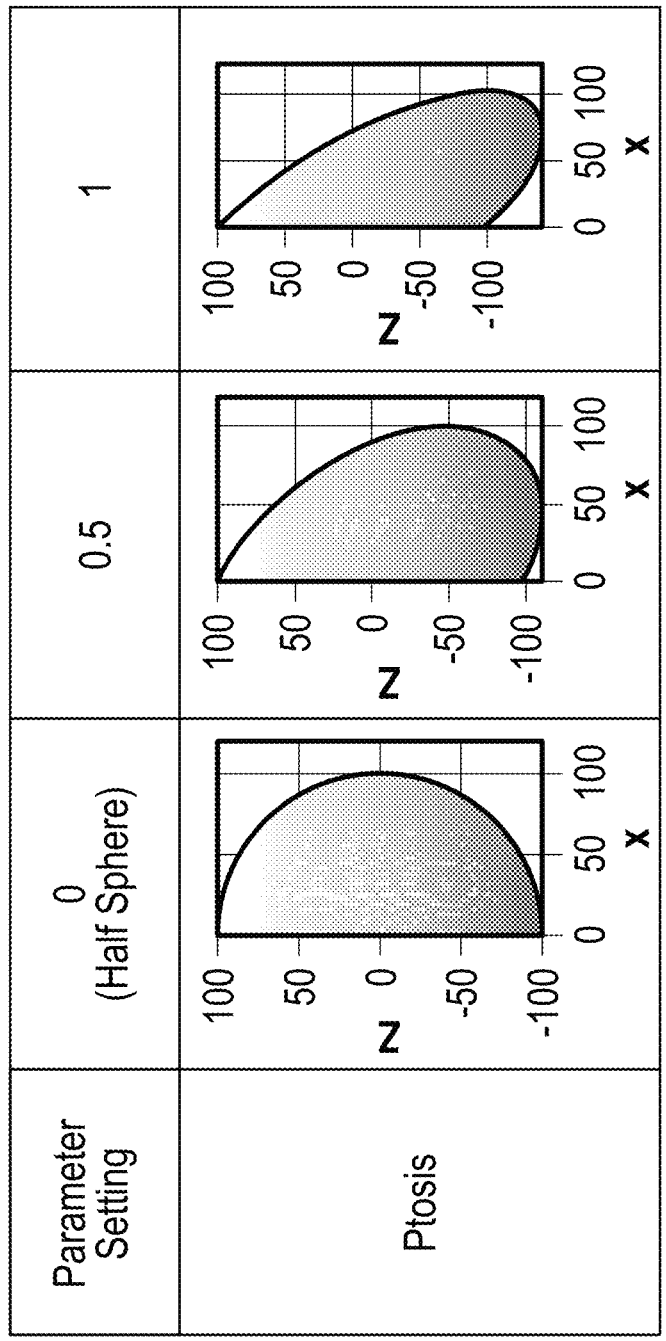
FIG. 20B is a table showing different ptosis settings, in accordance with aspects of the present disclosure.
Figure 22A:
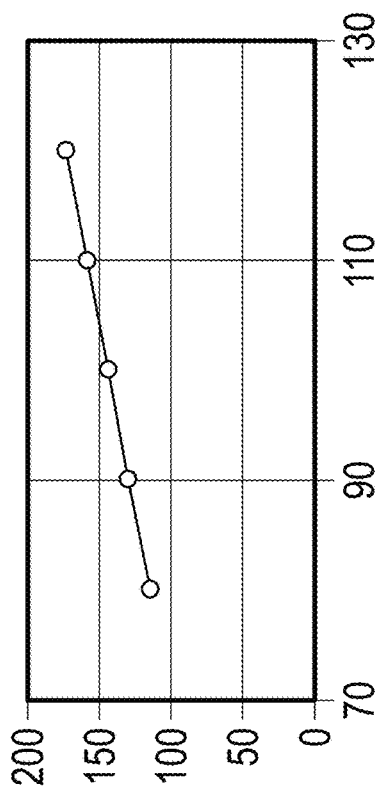
FIGS. 22A-D are graphs of the coefficient differences for height, width, depth and ptosis linearly related to their corresponding parameters, in accordance with aspects of the present disclosure.
Figure 22B:
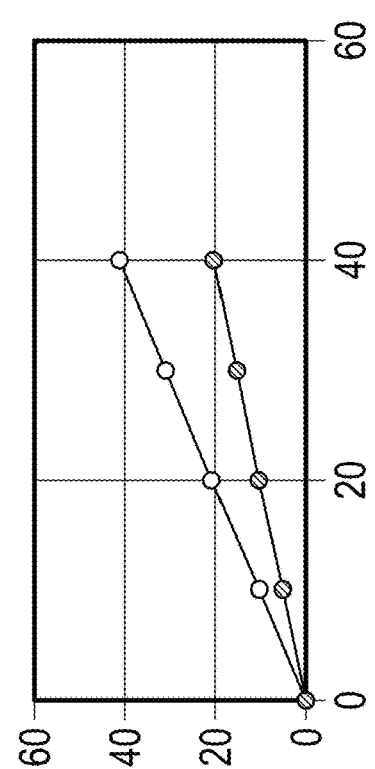
Figure 22C:
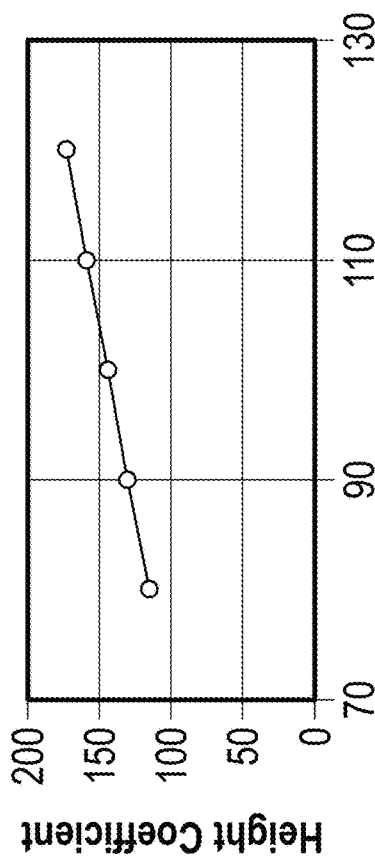
Figure 22D:
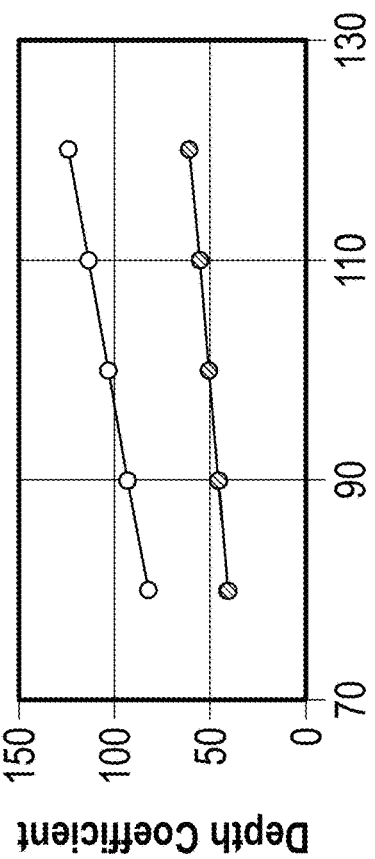
Figure 25A:
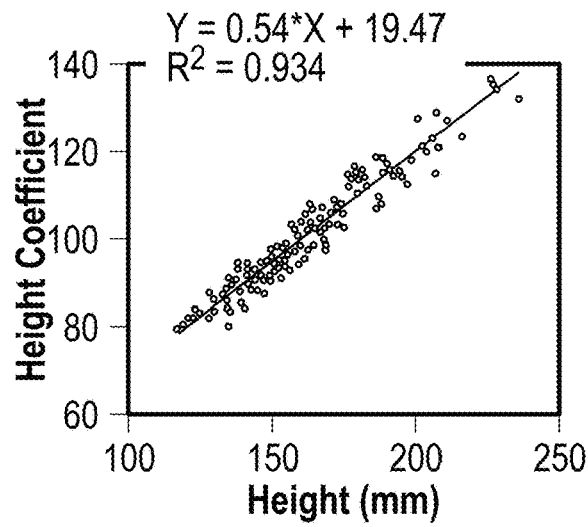
FIGS. 25A-D are scatterplots of selected parameter coefficients vs. the parameter, in accordance with aspects of the present disclosure.
Figure 25B:
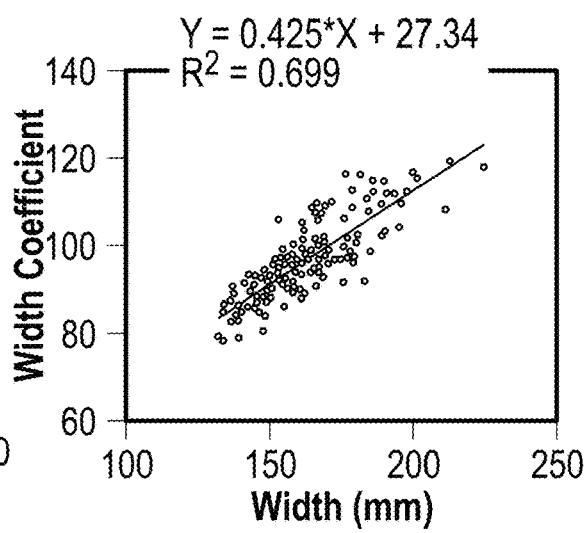
Figure 25C:
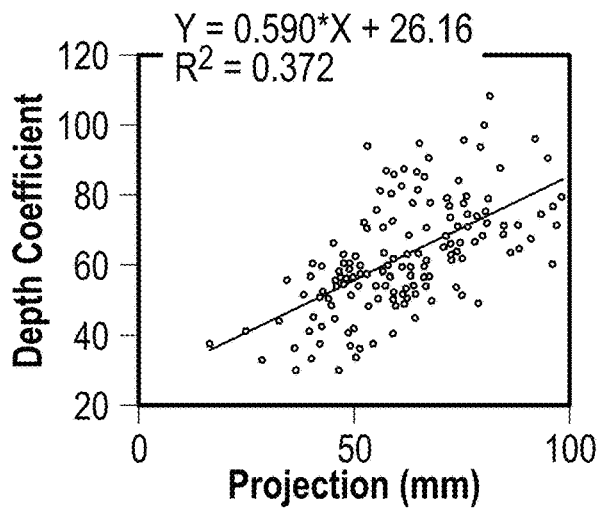
Figure 25D:
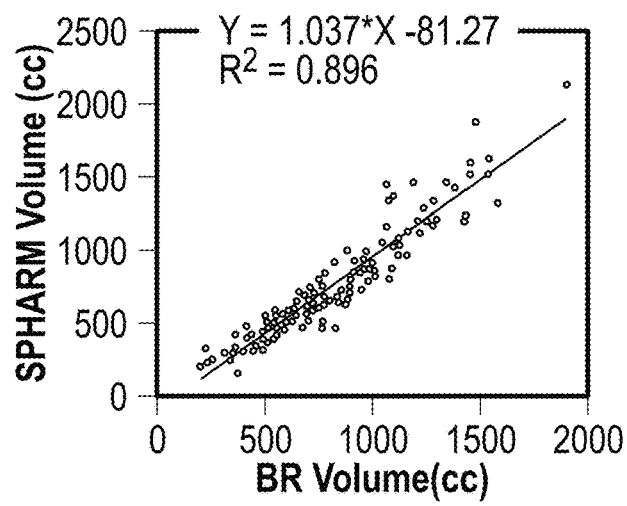

The SPHARM coefficients were evaluated to determine their relation to specific breast measurements that surgeons are familiar with, such as breast height, width, depth (projection), and ptosis. Instead of modifying the coefficients directly, different synthetic models representing different shapes and sizes were generated and their SPHARM coefficients were compared. A half sphere and modified a single parameter to simulate different heights, widths, depths, and ptosis (FIG. 20A and FIG. 20B) may be used. FIG. 20A is a table showing different height, width, and projection parameter settings. FIG. 20B is a table showing different ptosis settings as simulated using Chen's model. Ptosis is one of the five global deformations implemented in the model. FIGS. 21A-D are bar plots of the coefficient differences for height, width, depth, and ptosis. After calculating the SPHARM coefficient differences between two synthetic models with a height parameter of 100 versus 120, two coefficients, $c_{z1}^{-1}$ and $c_{z1}^{1}$, exhibited 91.25% of the total coefficient value differences. These two coefficients had equal value differences as a symmetric object was used. For two models with a width parameter of 100 versus 120, coefficients $c_{y1}^{-1}$ and $c_{y1}^{1}$ contained 92.55% of the total coefficient value differences. These two coefficients were also equal due to the symmetric object. For a depth parameter of 50 versus 100, coefficient $c_{x1}^{0}$ accounted for 54.71% of the total coefficient differences and coefficient $c_{x2}^{0}$ accounted for 26.87%. For a ptosis parameter of 0 versus 1, coefficient $c_{z1}^{0}$ accounted for 54.71% of the coefficient differences and coefficient $c_{z2}^{0}$ accounted for 26.87% of the difference (FIGS. 21A-D). The following coefficients after the first two largest coefficient differences (for height, width, depth, and ptosis) each accounted for less than 6.3% of the total coefficient differences. In various embodiments, breast shape changes may be related to a few SPHARM coefficients. Therefore, at least two coefficients may be changed to modify the size or shape of a model. FIGS. 22A-D shows how the coefficients are linearly related to changes in the parameters.

After finding the SPHARM coefficients most associated with height, depth, projection, and ptosis, the Pearson correlation between real breast measurements and the selected SPHARM coefficients was evaluated. A unit change in the coefficients may modify the breast shape. The volume of the modeled breast against the actual breast volume as measured using Passalis's method, which employs a Coons patch to represent the back wall of the breast was compared.

For example, using a dataset containing 87 preoperative images of patients, 161 of the 174 breasts were successfully converted to SPHARM models. The relationship between the ground truth ptosis rating provided by a surgeon versus the ptosis coefficients, the measured height versus the height coefficient, the measured width versus the width coefficient, the measured projection versus depth coefficient, and the volume measured in customized software versus the SPHARM model volume for the 161 SPHARM models was evaluated. Projection is defined as the distance from the most projected point on the breast to its corresponding point on the back side of the breast. The volume computed in customized software is the space between the breast surface and the estimated Coons patch. The volume for the SPHARM models is the space contained within the closed mesh object that was computed in MATLAB.

Referring to FIGS. 24A-B, tables of the P-values indicating whether the column means are significantly different are shown. Separating the ptosis coefficients based on the ptosis rating, the ptosis coefficients of ptosis grade 0 was significantly different from all the other ptosis grades. The first ptosis coefficient ($c_{z1}^0$ of ptosis grade 2 was not significantly different from ptosis grades 1 and 3. The second ptosis coefficient ($c_{z2}^0$ of ptosis grade 2 was not significantly different from ptosis grade 1, but was significantly different from ptosis grade 3 (FIGS. 24A-B). Ptosis grade 1 for both ptosis coefficients was significantly different from those of ptosis grade 3. The ptosis coefficients' average value of each grade may be progressively lower than that of the previous grade (FIG. 23). With further work, the ptosis coefficients could potentially be used to objectively grade ptosis and to provide consistent results.

Referring to FIGS. 25A-D, scatterplots of the height coefficient versus height, the width coefficient versus width, the depth coefficient versus projection, and the SPHARM volume versus the volume calculated in customized software are shown. The model height was strongly correlated with the height coefficient ($R^2=0.9$). The width coefficient had a lower, but still strong, correlation with the model width ($R^2=0.7$). The breast naturally curves toward the back on the lateral side of the breast, but the model width measurement does not account for this curvature, which may explain the lower correlation in width. The correlation between the SPHARM depth coefficient and the measured projection was moderately positive with $R^2=0.4$. The projection measurement versus its coefficient had a much lower correlation, since it is both highly dependent on the location of the highest projected point and the curvature of the backside of the breast, which are both variable. The SPHARM volume was strongly correlated with the customized volume ($R^2=0.9$), and the ratio was almost 1:1. All correlations were significant based on the Student's t distribution ($p<0.001$).

The SPHARM degree is a user-defined constant that determines the number of coefficients that is used to represent the breast model. While a higher degree increases the number of coefficients and leads to a more detailed reconstruction, there is also the possibility of overfitting with increasing degrees. A degree to use based on a dataset of 87 patients, which is described above. For example, of the 174 breasts, 161 breasts (92.5%) were successfully converted to SPHARM models using the manually selected fiducial points, which may be assigned as the ground truth dataset. Thirteen of the breasts did not convert to SPHARM models due to non-manifold vertices in the mesh. The ground truth breast objects consisted of, on average, 10654±3536 vertices and 21305±7073 faces. The smallest breast object had 4113 vertices and 8222 faces, which sets a limitation on the highest possible degree to 63 degrees or lower (($63+1)^2=4096$ vertices) for calculating the SPHARM coefficients. The triangles can be subdivided to increase the number of vertices and thus increase the maximum degree and reduce overfitting results. To obtain the best degree to represent the breast data, the SPHARM coefficients for degrees 10 to 50 at intervals of 10 for each input breast mesh (consisting of vertices and faces) in the dataset were calculated. The vertices of the reconstructed SPHARM model were compared to the vertices of the original breast mesh using the method described above. Since the coefficients are well-fitted to the input breast mesh, the reconstructed SPHARM models were given new spherical coordinates to estimate the locations of the face centroids in the input breast mesh. The rationale behind generating a model with new vertices is to evaluate if the coefficients generated with the degree used are accurate enough to generate a model close to the original without overfitting. The root-mean-square error (RMSE) and the Hausdorff distance between the vertices of the reconstructed SPHARM model and the face centroids of the original data were measured to determine the degree that resulted in the most accurate reconstructed SPHARM model.

Figure 27C:
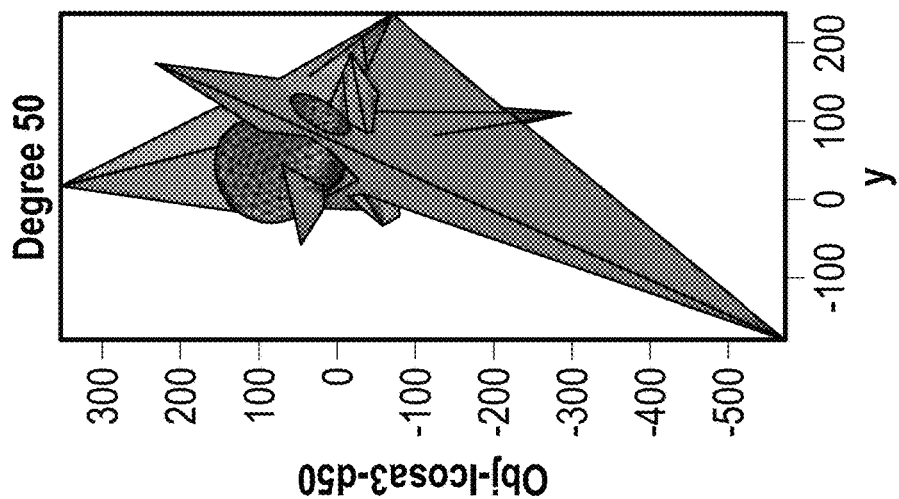
FIGS. 27A-C are diagrams of example SPHARM models based on degree 1, 20, and 50 using level 4 icosahedral subdivision, in accordance with aspects of the present disclosure.
Figure 27B:
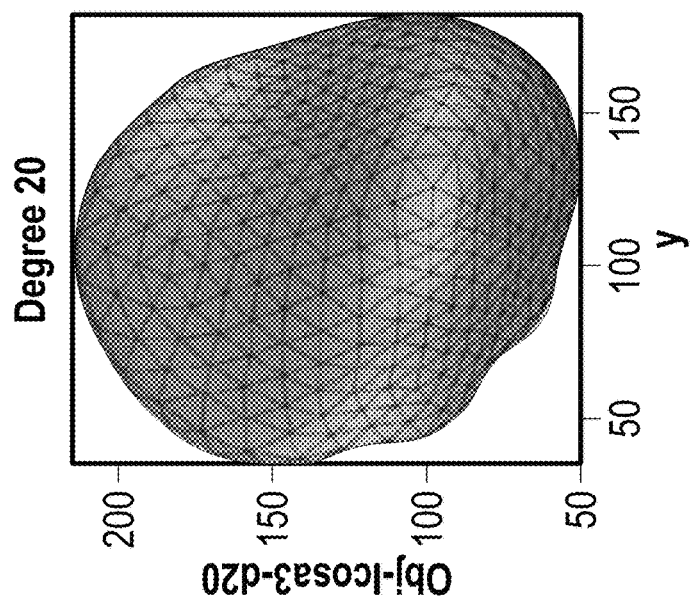
Figure 27A:
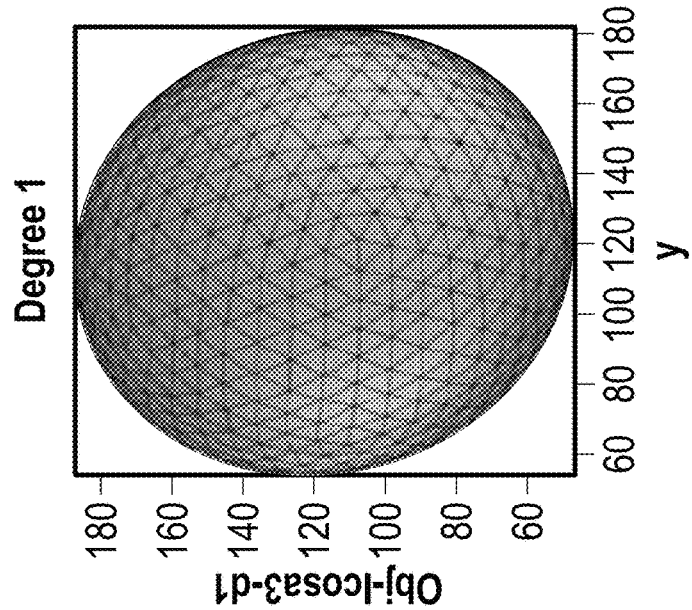

As shown in FIG. 26A, it was found for the data, that degrees 10-30 gave satisfactory results based on the RMSE. All breast samples had RMSE values less than 10 mm when using degrees 10 to 30. Using a degree of 40, 9.9% of the breast samples showed signs of overfitting, while degree 50 led to overfitting in 50.9% of the breast samples, as exemplified in FIG. 26B. However, the Hausdorff distance showed that some breast samples had a few points that were out of place for degree 30 (FIG. 26B). FIGS. 27A-C are depictions of example SPHARM models based on degree 1, 20, and 50 using level 4 icosahedral subdivision, in accordance with aspects of the present disclosure.

The quality of the results of the different degrees against the SPHARM coefficients that were identified to be most associated with height ($c_{z1}^{-1}$), width ($c_{y1}^1$) projection/depth ($c_{x1}^0$), and ptosis ($c_{z1}^0$ and $c_{z2}^0$) was also evaluated. The magnitude of the SPHARM coefficients associated with height, width, depth, and ptosis was calculated for different degrees for each breast sample and the average values are shown in FIG. 28. Using the Shapiro Wilk's normality test, the height and width coefficients were found to have non-normal distributions for all degrees ($p<0.01$). The depth and ptosis coefficients were found to have normal distributions for degrees 10 to 30 ($p>0.05$) but were not normally distributed for degrees 40 and 50 ($p<0.001$). Therefore, the Wilcoxon rank-sum test may be used, a non-parametric test, for evaluating whether the coefficients had different values between different degrees. The Wilcoxon rank-sum test showed that the coefficients were not significantly different between degrees 10-40, but degrees 10-40 were all significantly different from the coefficients calculated for degree 50 as shown in FIG. 29. Since the coefficients from degrees 10 to 30 are similar with <1% difference relative to the coefficient value (FIG. 30), there is flexibility in selecting the degree to represent the model. Different objects may be compared based on these coefficients even if the degree used to calculate the coefficients is different. The degree level of 20 for all simulations was used. Not only does degree 20 take less than half the time to compute than degree 30, it is also relatively accurately. The Hausdorff distance error also showed that degree 30 had a few cases where overfitting occurred.

In order to crop the breasts, two fiducial points had to be manually identified: the transition point and the lateral point. A test was conducted to evaluate the robustness of the algorithm to form a SPHARM model if the transition point and the lateral point were placed in different locations and to identify at what step in the algorithm it fails. The modeling algorithm can be divided into five major steps: (1) midline (ML) and inframammary fold or inferior breast-chest contour (IMF) detection, (2) breast cropping, (3) creating a closed mesh object, (4) spherical parameterization, and (5) SPHARM expansion.

Figure 31C:
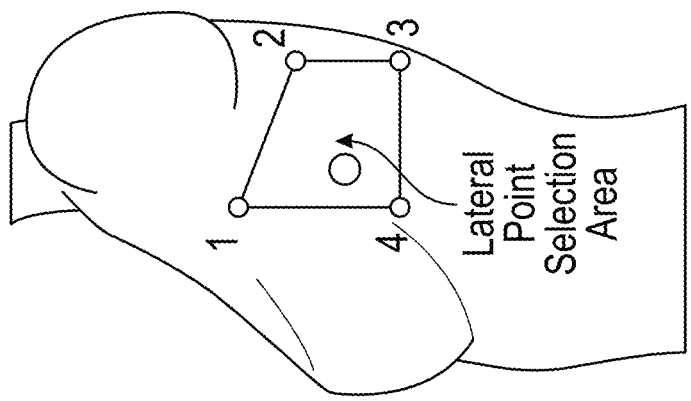
FIGS. 31A-C are diagrams of the selection area of the transition point and lateral point, in accordance with aspects of the present disclosure.
Figure 31B:
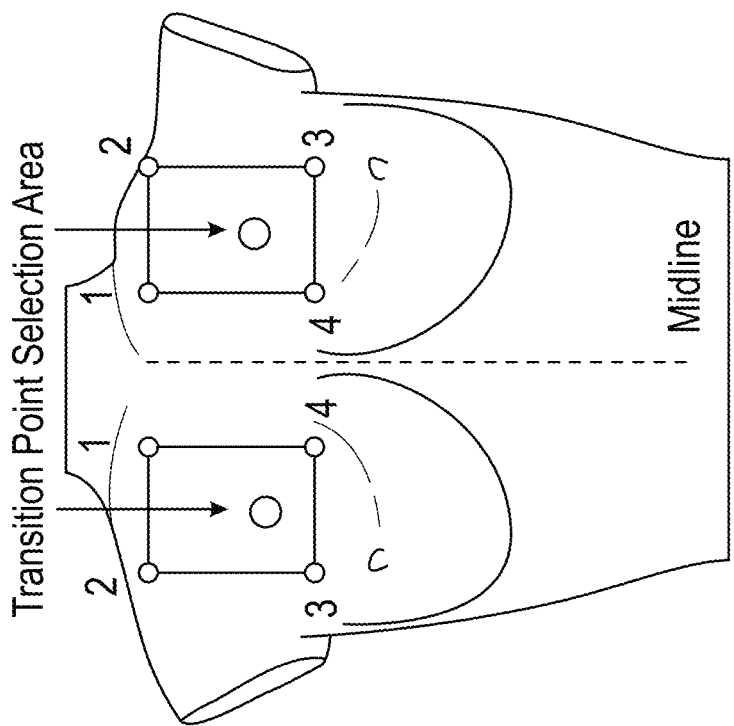
Figure 31A:
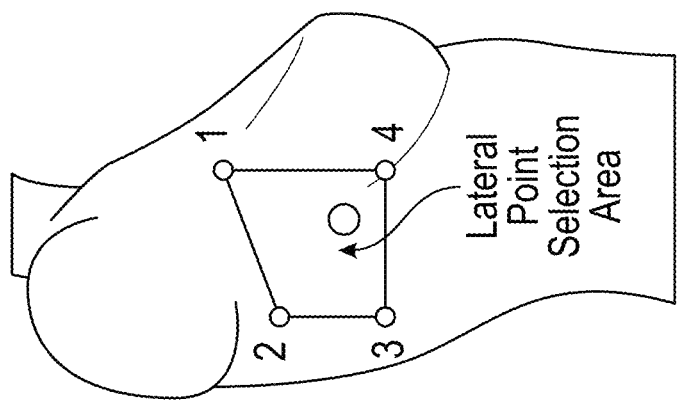

The region in which the transition point and lateral point may be located were identified based on certain criteria, and only the four corners of this region, which are called the extremities, were tested, as presented in FIGS. 31A-C. FIG. 31A shows the lateral point selection area for one breast. FIG. 31B shows the transition point selection area for both breasts. FIG. 31C shows the lateral point selection for the opposite breast. The dots represent the ground truth selection. The criteria for the transition point region were as follows: 1) area below the sternal-notch, 2) above the midline point and above the most projected point, and 3) within the middle 50% of the breast width. The criteria for the lateral point were as follows: 1) area below the armpits, 2) above the lowest point of the inframammary fold, and 3) within 37° ($\cos^{-1}$ 0.8) of the horizontal direction.

Figure 32:
FIG. 32 is a diagram of examples of breast cropping selecting the extreme corners for the transition and lateral points, in accordance with aspects of the present disclosure.
Figures 36, 37:
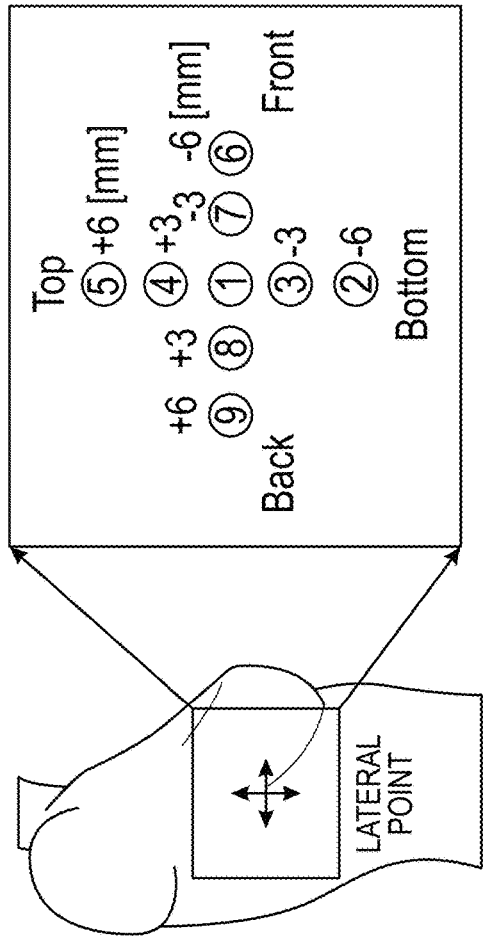
FIG. 36 is a diagram of the lateral point location of the different sets relative to the ground truth, in accordance with aspects of the present disclosure.
FIG. 37 is a table of the rate of successful processing at each step of the algorithm for different lateral point locations based on the 161 breasts, in accordance with aspects of the present disclosure.
Figures 38, 39:
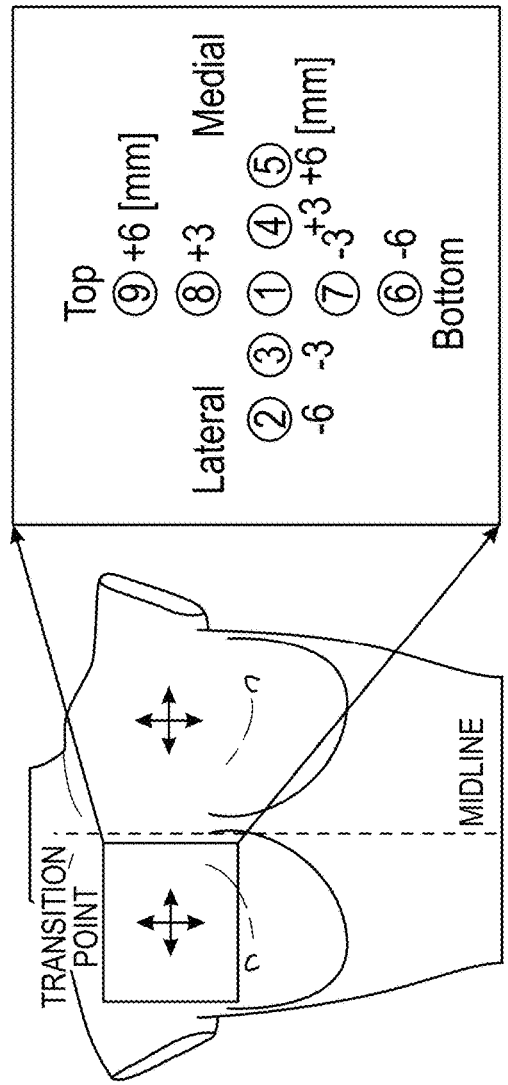
FIG. 38 is a diagram of the transition point location of the different sets relative to the ground truth, in accordance with aspects of the present disclosure.
FIG. 39 is a table of the rate of successful processing at each step of the algorithm for different transition point locations based on 161 breasts, in accordance with aspects of the present disclosure.
Figures 44A, 44B:
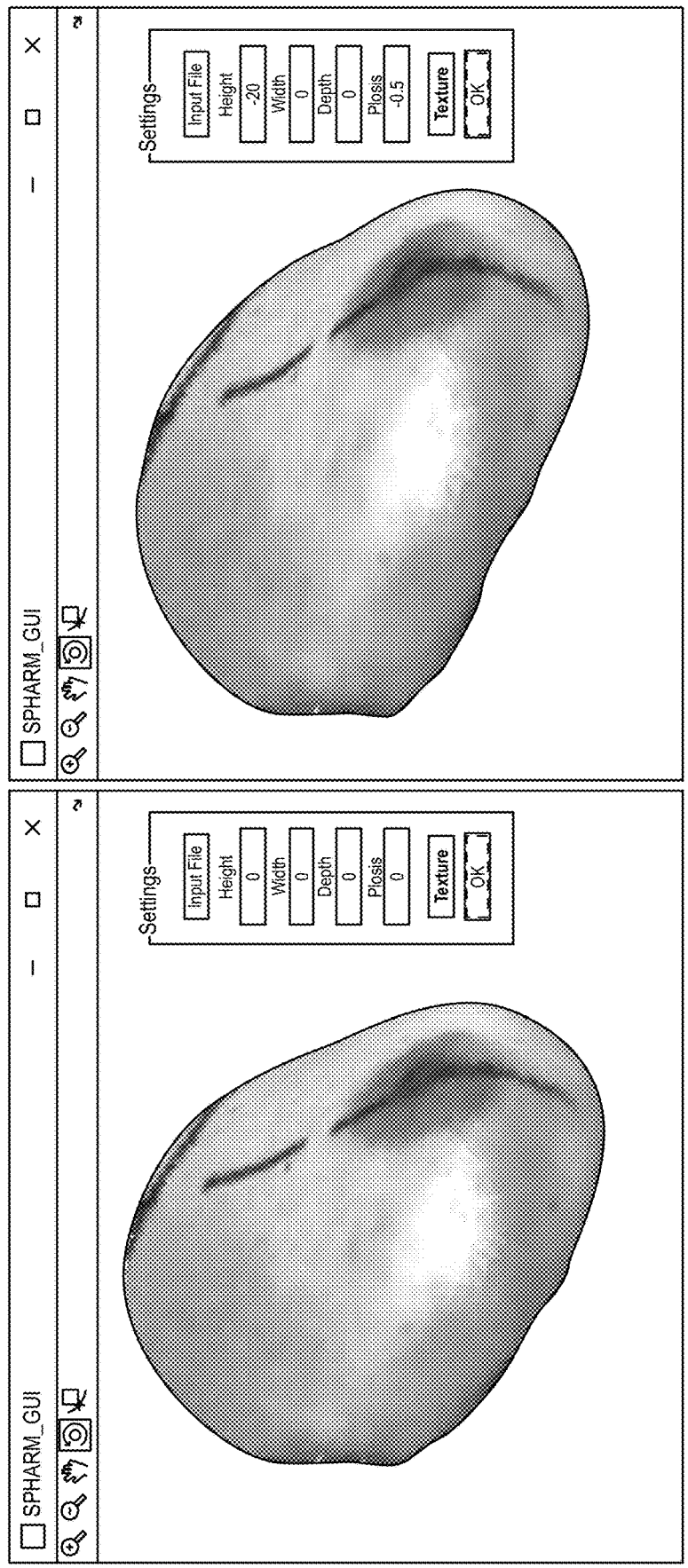
FIGS. 44A-B are images of an original breast (FIG. 44A) and modified breast (FIG. 44B) by changing the SPHARM coefficients for height, width, projection, and ptosis, in accordance with aspects of the present disclosure.

The true transition point and the lateral point will always be within these defined regions, and a properly trained user will not select the fiducial point outside of these regions. The software itself can be designed to limit the choices to these regions. The four corners of the region identified for the transition point and lateral point were tested. The four transition points (TP) and the four lateral points (LP) were paired as follows:

Set 0: Ground truth (Manually selected TP and LP)
Set 1: Top-medial TP and top-front LP
Set 2: Top-lateral TP and top-back LP
Set 3: Bottom-lateral TP and bottom-back LP
Set 4: Bottom-medial TP and bottom-front LP Referring to FIG. 32, a patient's breasts based on these five pairs of points may be modeled. FIG. 33 shows the rate of successful processing at each step of the algorithm for different landmark positions for the modeled breast. FIG. 34 shows the Euclidean distance of the user selection relative to the ground truth selection for ten (10) images. FIG. 35 is a table of the Euclidean distance of the corner (extreme) selections relative to the ground truth selection for 87 images. FIG. 36 is a diagram of the lateral point (LP) location of the different sets relative to the ground truth (set 1). FIG. 37 is a table of the rate of successful processing at each step of the algorithm for different lateral point locations based on 161 breasts. FIG. 38 is a diagram of the transition point (TP) location of the different sets relative to the ground truth (Set 1). FIG. 39 is a table of the rate of successful processing at each step of the algorithm for different transition point locations based on 161 breasts. FIG. 40 is a table of the statistics on the projection percent difference between the ground truth selection and shifting the TP three (3) and six (6) millimeters in different directions including lateral, medial, down and up. FIG. 41 is a table depicting statistics on the volume percent difference between the ground truth selection and shifting the TP three (3) and six (6) millimeters in different directions including lateral, medial, down and up. FIG. 42 is a table depicting statistics on the projection percent difference between the ground truth selection and shifting the LP three (3) and six (6) millimeters in different directions including down, up, forward and backward. FIG. 43 is a table depicting statistics on the volume percent difference between the ground truth selection and shifting the LP three (3) and six (6) millimeters in different directions including down, up, forward and backward Referring to FIGS. 44A-B, a program may be used to adjust the height, width, depth, and ptosis to any loaded breast data. For example, a MATLAB application was created that allows any user to easily apply different settings for adjusting height, width, projection, and ptosis to any loaded breast data that has SPHARM coefficients computed for it. The original texture or a generic texture can be mapped to the breast model. The application takes less than half a second to process the input parameters and display the modified breast model.

Figure 45B:
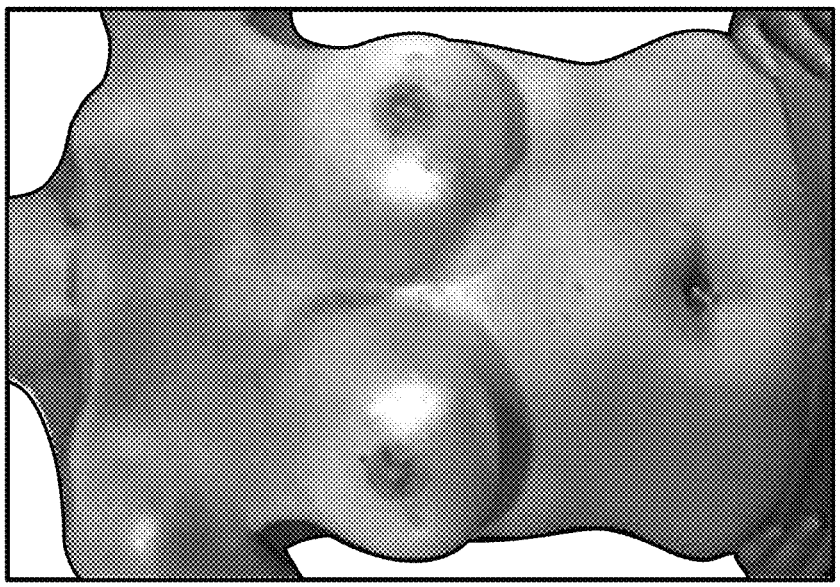
FIGS. 45A-B are images of an example of a bilateral TRAM flap reconstruction (FIG. 45A) and a bilateral implant reconstruction (FIG. 45B), in accordance with aspects of the present disclosure.
Figure 45A:
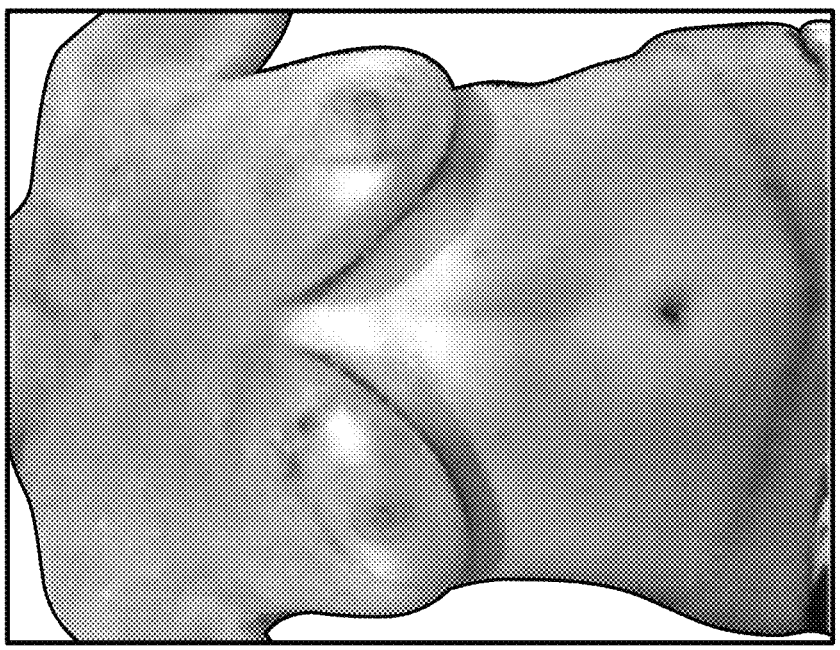

Referring to FIGS. 45A-B, two commonly performed types of breast reconstruction TRAM flap and implant reconstructions are shown. TRAM flaps tend to give breasts a smooth teardrop shape that looks more natural (FIG. 45A), while implants create round and protruded shaped breasts (FIG. 45B).

Referring to FIGS. 46A-B, comparisons using sets of confusion matrices for k-nearest neighbor (k-NN) classification (k=3 and 5), quadratic discriminate analysis (QDA), and Naïve Bayes classifier using the SPHARM coefficients versus matrices for k-NN classification, quadratic discriminate analysis, Naïve Bayes classifier using BMI, breast volume, and breast dimensions were made. Classification was performed to see if the reconstructed breasts can be differentiated by reconstruction type using the SPHARM coefficients as feature vectors. The SPHARM coefficients can differentiate the breasts based on their shapes, which can later be applied in classifying natural breast shapes.

For a standard of comparison, classification using BMI was performed, breast height, width, projection, and volume as measured using customized software. The results shown in FIGS. 46A-B indicated that the SPHARM coefficients has more discriminative ability than only using the BMI, breast height, width, depth, and volume.

Figure 48:
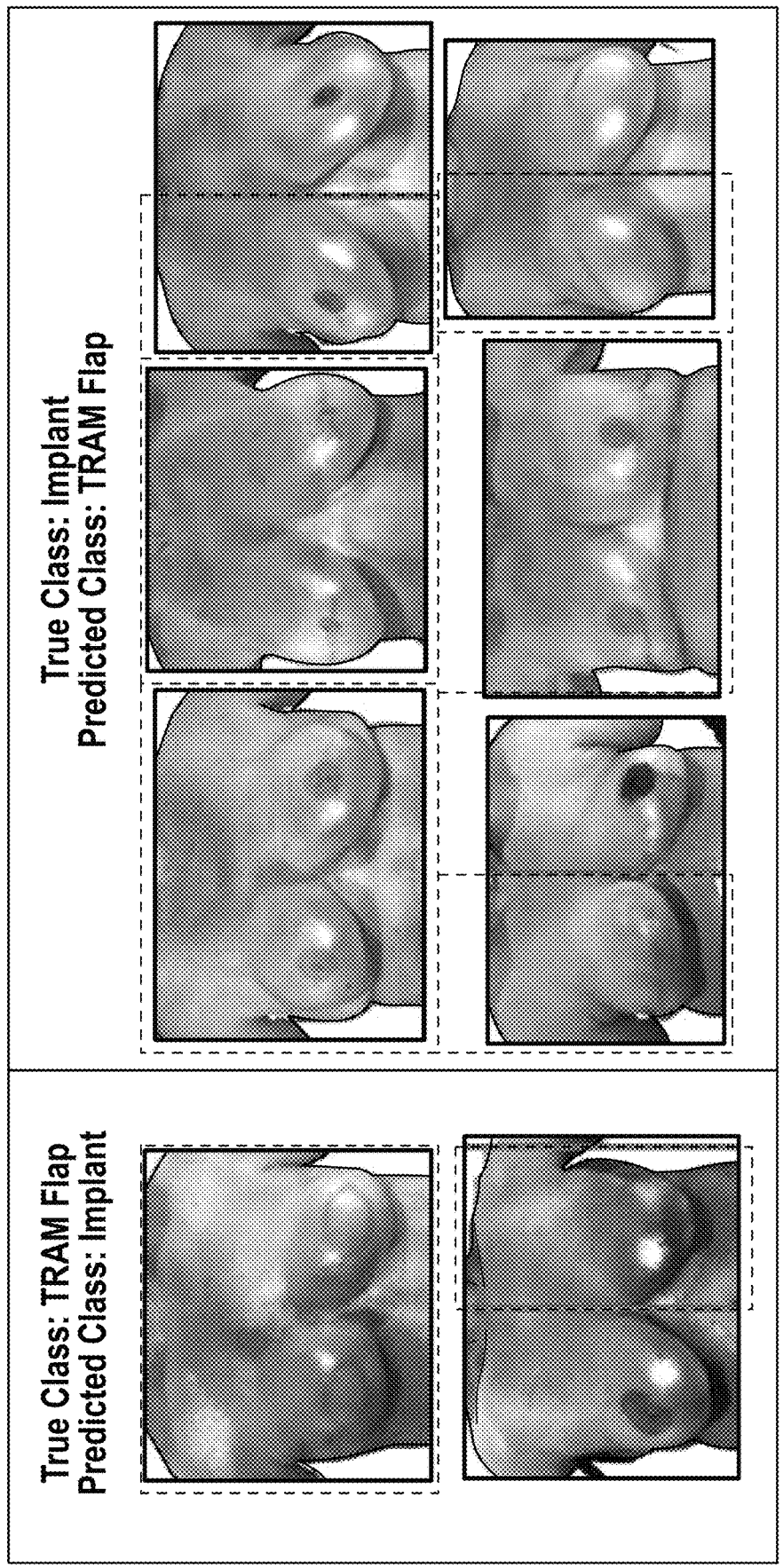
FIG. 48 is a set of images of true versus predicted class reconstructed breasts according to a TRAM flap or implant, in accordance with aspects of the present disclosure.

Referring to FIG. 48, a set of images of true versus predicted class reconstructed breasts according to a TRAM flap or implant are shown.

A template breast model can be created from a set of breast models that are similar in shape using the RMSD. Two examples of the average breast object are shown below. One TRAM flap reconstructed breast model was selected, and four other breast models that were similar in shape (out of 28 TRAM reconstructed breasts) based on the coefficients were also selected. The five breast models shown in FIGS. 49A-B were averaged together to form an average breast model shown in FIG. 51A. The original images are shown in FIG. 49A and the SPHARM models with the original texture applied are shown in FIG. 49B. All right breasts were mirrored in order to compare with the left breasts. The RMSDs were between 5.51 and 7.16 for the first TRAM flap reconstructed breast versus the other four breasts. Relative to the average breast shape, the RMSDs of the five breasts were between 3.83 and 4.66. In another example, an implant reconstructed breast model and its four nearest implant reconstructed breast models (out of 23 implant breasts) were averaged together (FIGS. 50A-B) to form an average breast model (FIG. 51B). FIG. 50A shows the original images and FIG. 50B shows the SPHARM models with the original texture applied. The RMSDs were between 3.89 and 5.54 for the implant reconstructed breast versus the other four implant reconstructed breasts. Relative to the average breast shape, the RMSDs of the five breasts were between 2.57 and 4.38. After demonstrating with two examples that an average breast representing a set of similar breast shapes can be created, the following section shows how the average breast may be used for predictive modeling.

Referring to FIGS. 52A-D, tables of data for a set of patients are shown describing the types of operations undergone (FIG. 52A), the number of patients, the RMSD of various preoperative and postoperative breast comparisons (FIG. 52B), the RMSD for various BMI (FIG. 52C), and the HD for various BMI (FIG. 52D). FIG. 52A is a table of the procedures conducted on the left and right breast of each patient and the average RMSD for each set of patients with the same procedures. FIG. 52B is a table of the statistics on the RMSD comparing preoperative, postoperative, and predicted breast shapes. FIG. 52B is a table of the statistics on the RMSD comparing preoperative, postoperative and predicted breast shapes. FIG. 52C is a table of the RMSD between the true postoperative models and the predicted models organized into three BMI groups. FIG. 52D is a table of the HD between the true postoperative models and the predicted models organized into three BMI groups.

Figure 53:
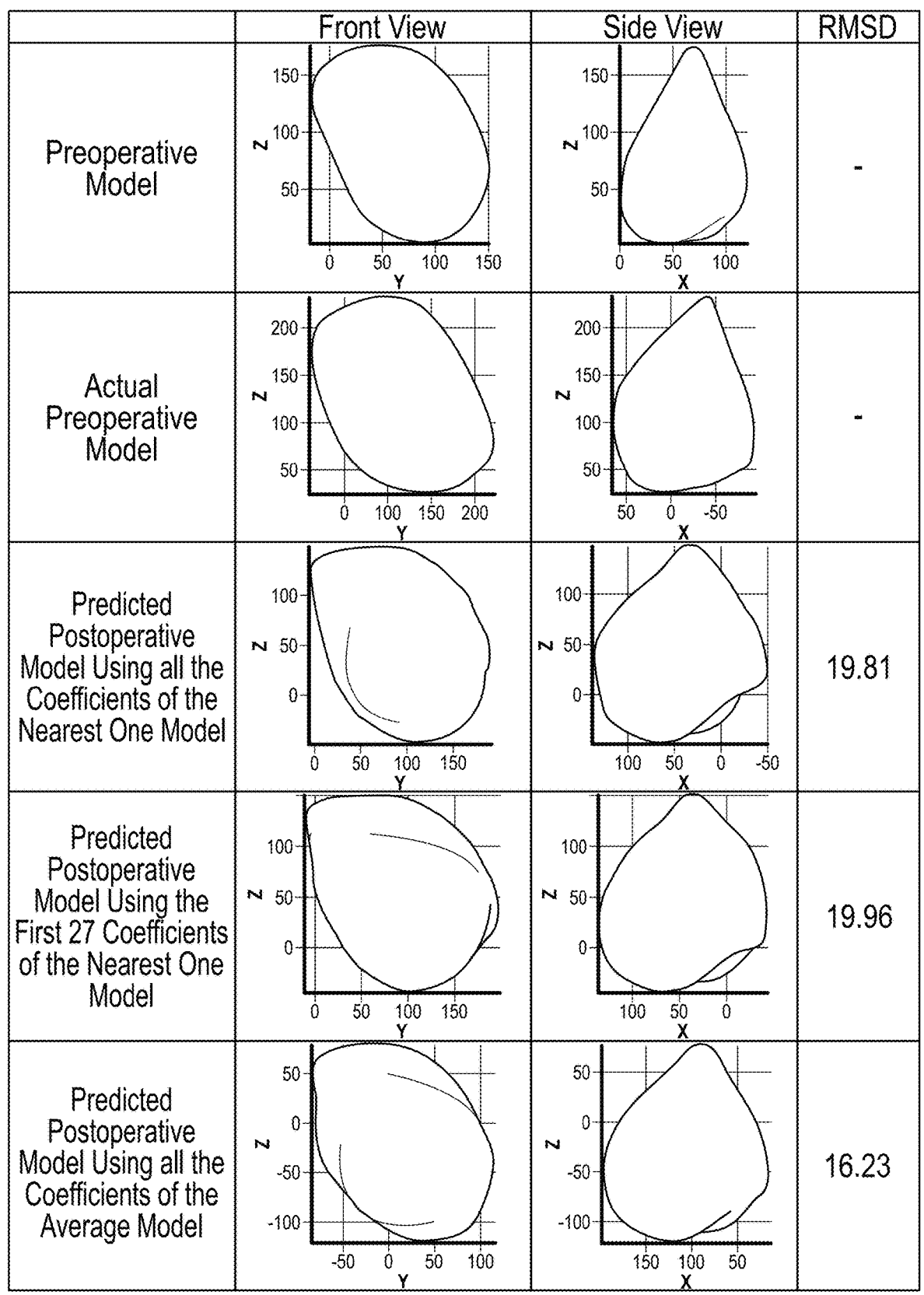
FIG. 53 is a table depicting examples of predicted postoperative models, in accordance with aspects of the present disclosure.
Figure 54:
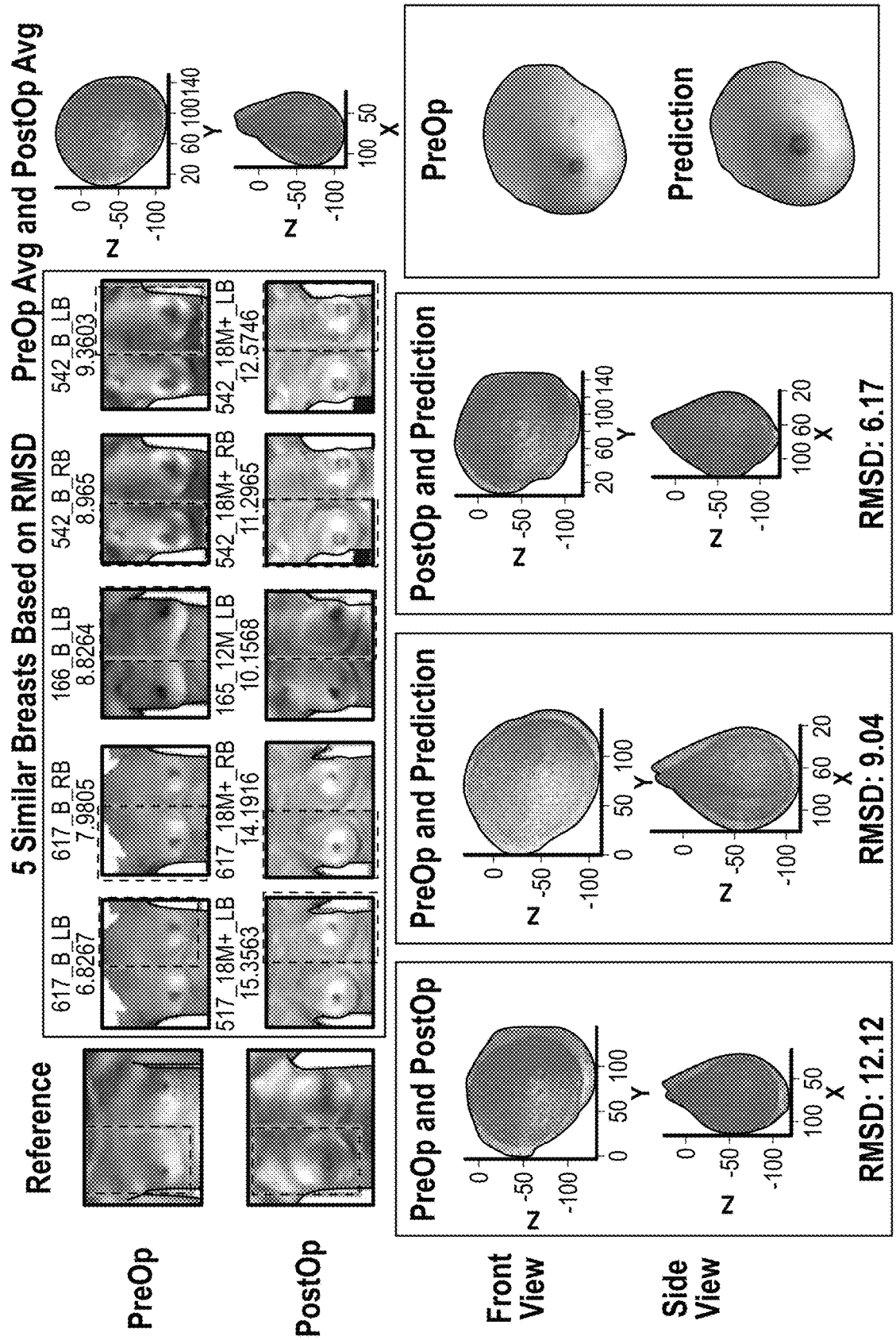
FIG. 54 is a diagram of the best prediction out of 53 reconstructed breasts, in accordance with aspects of the present disclosure.
Figure 55:
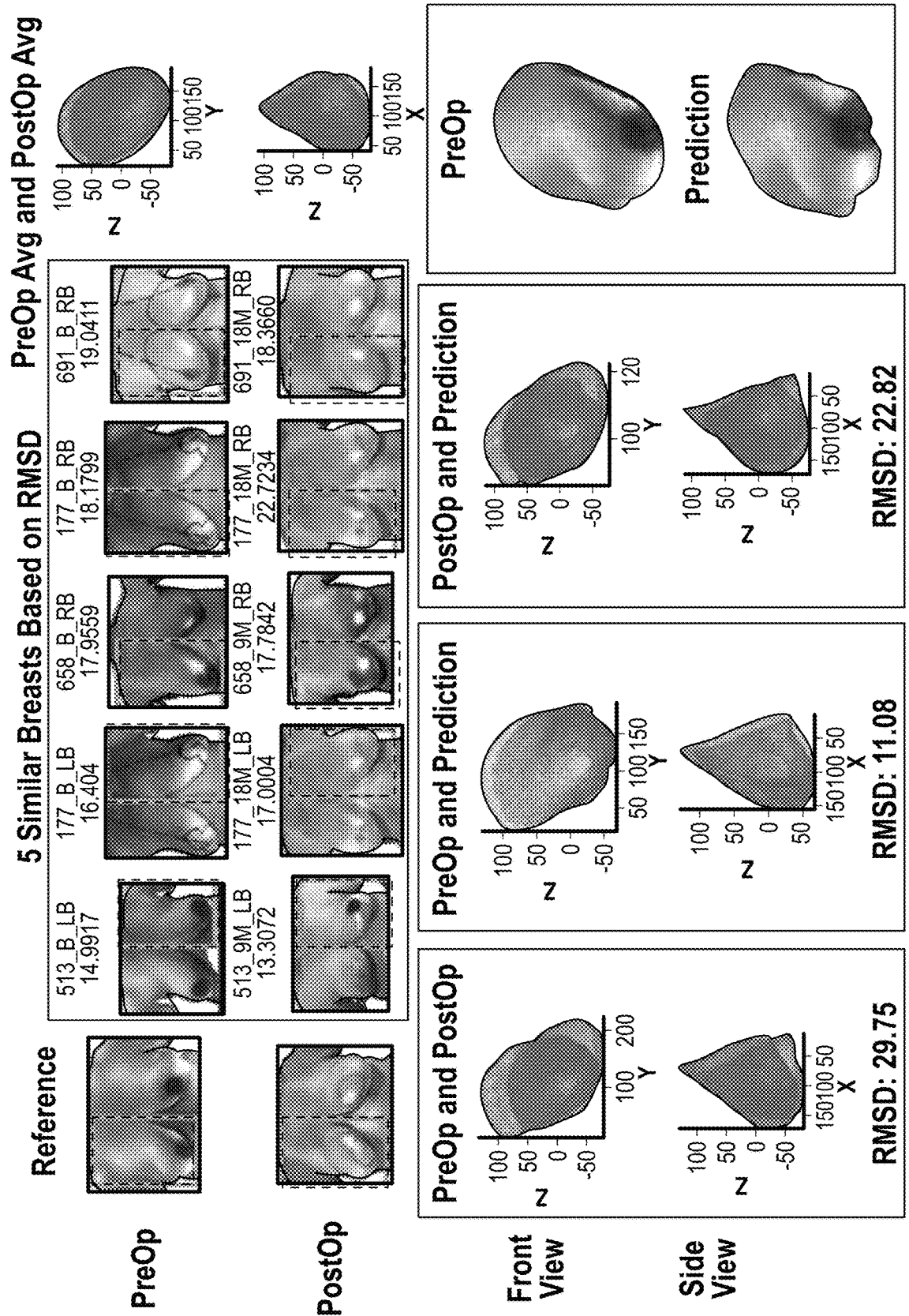
FIG. 55 is a diagram of the worst prediction out of 53 reconstructed breasts, in accordance with aspects of the present disclosure.

Referring to FIG. 53, postoperative models may be predicted. In various embodiments, by using the average breast model described in the previous section, individualistic features may be averaged and/or smoothed out, such as the nipple. In this way, a depression does not get added in the predicted breast, as shown in row 3 of FIG. 53. The RMSD between the predicted and the actual postoperative model also improved. Only the first 27 coefficients were added in order to avoid the depression but found that the RMSD was lower when using the average object approach, as presented in FIG. 52B and exemplified in FIG. 53. For example, a prediction had a RMSD of 6.17 between the true postoperative model and the predicted model as shown in FIG. 54. The five closest breast models had RMSDs between 6.83 and 9.35, so there were relatively similar shaped breasts in the database. On the other hand, in a prediction, the reference image's closest breast models in the database had RMSDs between 14.99 and 19.04, so there were just wasn't a similar breast shape available in the database to make a more accurate prediction (FIG. 55). When the prediction models were separated by BMI, the RMSDs between the true postoperative model and the predicted model were lower for BMI less than 25 and higher for BMI greater than 30 (FIG. 52C). The average Hausdorff distance was also larger for patients with BMI greater than 30 than the patients with lower BMI (FIG. 52D). The Hausdorff distance was computed between the true postoperative SPHARM model and the predicted model that were sampled using a level 5 icosahedral subdivision (10242 vertices and 20480 faces). Larger breasts have poorer predictions since there can be more variability in size and shape than for small breasts. In various embodiments, SPHARM models may be used to predict outcomes, which may be improved with a larger dataset and matching by age, BMI, breast volume, reconstruction type, smoking history, and other factors including patient preferences. All of these factors are discussed during patient consultations, which can be used to help predict the model.

In various embodiments, a method to model the breast that can be used to analyze, compare, and modify its shape, is shown. The algorithm may be robust to small differences in the point selection of the transition point and lateral point. Results on classification for different breast reconstruction types are shown, creating average breast objects that can represent a particular shape, and predictive modeling. The three-dimensional model based on SPHARM and its further development will provide a state-of-the-art surgical planning tool for surgeons to visualize and interactively evaluate the morphology of the breast. It will also help patients in making more informed decisions. In addition, for a patient who is yet to undergo breast reconstruction, her breasts can be shape matched to the preoperative breasts of previous reconstruction patients and then shown their post-surgical outcomes, which may help the patient mentally prepare for possible outcomes.

In various embodiments, a standard may be developed for automatically detecting the lateral and transition points to maintain consistency (increase precision), if not accuracy, across different time points in the reconstructive process (as the patient is imaged every three months before and after mastectomy and reconstruction) as well as across different patients. The model may also be reconnected with the torso to evaluate the overall appearance of the breast in relation to the human body. As demonstrated in the classification results, the SPHARM coefficients has potential for classifying different breast shapes. There are several natural breast shapes that have been identified for women. They may serve as a starting point for helping to objectively categorize the shape of a woman's breasts in order to select the right bra size and type that would fit comfortably.

In various embodiments, a method to predict surgical outcome may include acquiring a 3D pre-op image of a patient, looking at database for similar demographics (e.g., age etc.) and breast size and shape, where the database also includes pre-op and post-op 3D images, find post operation image of those patients, determine new SPHARM coefficients, applying the SPHARM coefficients to the 3D pre-op image of the patient, and morphing the breast based on the new SPHARM coefficients.

In various embodiments, a method to predict surgical outcome may include the generation of template breast shapes that can be then used to predict and/or visualize the breast shape for women seeking a particular option, or to compare different options.

Referring to FIGS. 57A-D, images of frontal and lateral views of pre-op (P1), post-op (P2), estimate (E) and overlay of estimate on the post-op breast for four breasts in the input test set are shown. The post-op images in FIGS. 57A-D are actual reconstruction results obtained by imaging the patient after the surgery at 18 months in a consultation timeline.

In various embodiments, deep learning/AI/machine learning algorithms may be used in the above method to predict surgical outcomes. The predicting may include using a machine learning algorithm, where training data inputs include for example, pre and post operation image data and/or patient demographic data. Machine learning algorithms may include, for example, a neural network, random forest regression, linear regression (LR), ridge regression (RR), least-angle regression (LARS), and/or least absolute shrinkage and selection operator regression (LASSO). The machine learning algorithms may be executed on the controller (see FIG. 3B), and/or on a remote computing system.

In the clinical setting, a 3D surface image of pre-op breast is available before the surgery is scheduled and the surgical option under consideration is known, or to be determined. The shape change of breasts pre- and post-surgery is dependent on surgery type and other medical parameters such as ptosis grade, implant size and weight, skin elasticity. It is not feasible to compute a single generalized transformation for pre-op breast shape to the expected post-op shape for all surgery types. A data-driven approach may be employed to estimate the transformation vector using nonlinear regression for any changes in breast shape, including natural (e.g. aging, pregnancy, or other deformities), or surgical."

SPHARM coefficients of the pre-op breast and the transformation vector required to obtain its post-op shape using least squares optimization for twenty-one pre-op and its corresponding post op breasts and trained a random forest regression function to learn the non-linear relationship between the transformation vectors, are computed. Random regression forest is an ensemble learning method that is a popular model for non-linear regression. Random forest regression efficiently preforms regression for multivariate data. For example, the regression function was trained using bootstrap sample of 21 breasts, with 1320 SPHARM coefficients, $x=[x_1, x_2, \ldots x_{1320}]^T$ of the pre-op breast as the input features and the transformation vector $\beta=[\beta_1 \beta_2 \ldots \beta_{1319} \beta_{1320}]^T$ as the regression output. Random regression forest is made of several individual regression trees. A regression tree is recursively constructed such that at each node the training data is split on a randomly chosen feature variable so that entropy at the node is minimized. In a regression tree the entropy of the feature densities associated with different nodes decreases when going from the root towards the leaves. When presented with an unseen test data, the random forest simply averages the results from individual regression trees to predict the output. The transformation obtained from the regression to the pre-op (P1) breast coefficients to obtain the estimation of post-op shape (see FIG. 57D) was applied.

In various embodiments, the method further includes identifying different types of natural breast shapes and contours, shapes related to breast diseases, and outcomes of surgical procedures, including reconstructed breasts (at least one of autologous or implant reconstructed breasts), and cosmetic procedures (augmentation, reduction, mastopexy), based on spherical harmonic coefficients.

In various embodiments, a method of predicting includes creating a general shape template from images of several women. In an embodiment, the general template may be created using images of other breasts from a group of women (similar in demographics such as BMI, age, etc.). In an embodiment, the general template may be created for specific breast conditions using data from large groups of women (i.e. not the few that have the most similar shape).

It is contemplated that the database for 3D images of patient with similar demographics are not limited to age, breast size, or breast shape, and may contain other demographic data.

Figure 58:
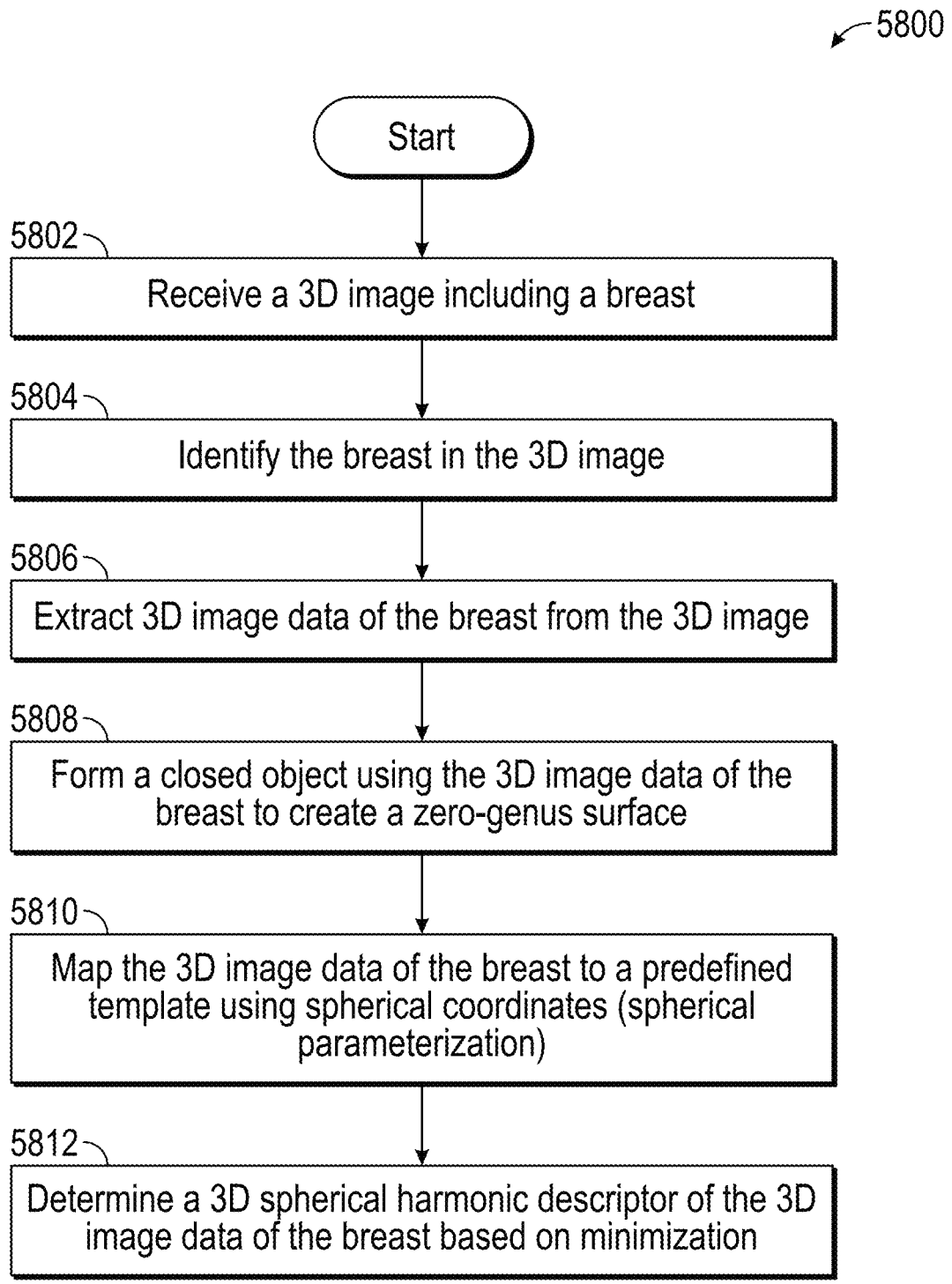
FIG. 58 is a block diagram of a method for modeling a breast, in accordance with the present disclosure.

FIG. 58 is a block diagram of a method for modeling a breast, in accordance with the present disclosure.

The flow diagram of FIG. 58 shows a computer implemented method 900 for modeling a breast. Persons skilled in the art will appreciate that one or more operations of the method 5800 may be performed in a different order, repeated, and/or omitted without departing from the scope of the disclosure. In some methods in accordance with this disclosure, some or all of the operations in the illustrated method 5800 can be operated on the controller 200 (see FIG. 3B). Other variations are contemplated to be within the scope of the disclosure. The operations of FIG. 58 will be described with respect to a computing device, e.g., controller 200 of system 300 (FIG. 3A), or any other suitable computing system device or location thereof including a remotely disposed computing device. It will be understood that the illustrated operations are applicable to other systems and components thereof as well.

Initially, at step 5802, the method receives a 3D image (e.g., a pre-operative image), which includes a breast. Next, at step 5804, the method identifies the breast in the 3D image. Next, at step 5806, the method extracts 3D image data of the breast from the 3D image. Next, at step 5808, the method forms a closed object using 3D image data of the breast to create a zero-genus surface. Forming of a closed object may include identifying holes in a mesh by finding boundary edges, which are edges that are not shared by two faces, calculating the angle between adjacent boundary edges at a vertex, locating the smallest angle and creating a new triangle at the vertex, wherein a location of new vertices is determined by an average edge length and the shortest direction to close a gap across two meshes, computing a distance between every newly created vertex and every related boundary vertex, in a case where the distance between them is less than a predetermined threshold, they are merged, and updating the mesh based on the computed distance. Next, at step 5810, the method maps the 3D image data of the breast to a predefined template using spherical co-ordinates (e.g., spherical parameterization). Next, at step 5812, the method determines a 3D spherical harmonic descriptor of the 3D image data of the breast, for example, based on minimization. The method may include identifying parameters of the 3D spherical harmonic descriptor that represent anatomical breast parameters including height, width, depth, and/or ptosis. The method may include identifying different types of breast shapes, such as autologous and/or implant reconstructed breast or a combination of autologous and implant breasts, based on spherical harmonic (SPHARM) coefficients.

The method may include predicting a post-operative breast shape from the 3D image based on the 3D spherical harmonic (SPHARM) model and outputting a predicted 3D image based on the predicted post-operative breast shape. The method can also be used for predicting any natural breast shape change such as, for example, due to the aging process and weight loss/gain, or pathological breast shape change such as deformities, or any surgical alterations.

The method may include searching a database, of pre-operative and post-operative 3D images, for a 3D image of at least one second patient with similar demographics or medical history, to the received the patient of the 3D image, determining SPHARM coefficients of the received 3D image, locating a pre-operative 3D image of a second patient with a similar age, breast size, and/or breast shape based on the SPHARM coefficients. The method may further include locating a post-operative 3D image of the second patient, generating an average pre-operative 3D image based on the pre-operative 3D images, generating an average post-operative 3D image based on the post-operative 3D images, determining SPHARM coefficients of at least one of an average pre-operative 3D image or a located post-operative 3D image, determining SPHARM coefficients of at least one of an average post-operative 3D image or a located post-operative 3D image. The method may further include determining a difference between SPHARM coefficients of the received 3D image or the average pre-operative image and SPHARM coefficients of the average post-operative 3D image, applying the difference in SPHARM coefficients to the received 3D image, and morphing the breast of the received 3D image based on the determined SPHARM coefficients.

The embodiments disclosed herein are examples of the disclosure and may be embodied in various forms. For instance, although certain embodiments herein are described as separate embodiments, each of the embodiments herein may be combined with one or more of the other embodiments herein. Specific structural and functional details disclosed herein are not to be interpreted as limiting, but as a basis for the claims and as a representative basis for teaching one skilled in the art to variously employ the present disclosure in virtually any appropriately detailed structure. Like reference numerals may refer to similar or identical elements throughout the description of the drawings.

The phrases "in an embodiment," "in embodiments," "in various embodiments," "in some embodiments," or "in other embodiments" may each refer to one or more of the same or different embodiments in accordance with the present disclosure. A phrase in the form "A or B" means "(A), (B), or (A and B)." A phrase in the form "at least one of A, B, or C" means "(A); (B); (C); (A and B); (A and C); (B and C); or (A, B, and C)."

Any of the herein described methods, programs, algorithms or codes may be converted to, or expressed in, a programming language or computer program. The terms "programming language" and "computer program," as used herein, each include any language used to specify instructions to a computer, and include (but is not limited to) the following languages and their derivatives: Assembler, Basic, Batch files, BCPL, C, C+, C++, Delphi, Fortran, Java, JavaScript, machine code, operating system command languages, Pascal, Perl, PL1, scripting languages, Visual Basic, metalanguages which themselves specify programs, and all first, second, third, fourth, fifth, or further generation computer languages. Also included are database and other data schemas, and any other meta-languages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing drawings are presented only to demonstrate certain examples of the disclosure. Other elements, steps, methods, and techniques that are insubstantially different from those described above and/or in the appended claims are also intended to be within the scope of the disclosure.

What is claimed is:

1. A computer implemented method of modeling a breast shape, the method comprising:
    receiving a 3D image including a breast;
    identifying the breast in the 3D image;
    extracting 3D image data of the breast from the 3D image;
    forming a closed object using the 3D image data of the breast to create a zero-genus surface;
    mapping the 3D image data of the breast to a predefined template using spherical coordinates; and
    determining a 3D spherical harmonic (SPHARM) descriptor of the 3D image data of the breast.

2. The method of claim 1, wherein the method further includes identifying parameters of the 3D spherical harmonic descriptor that represent anatomical breast parameters including at least one of a height, a width, a depth, or ptosis.

3. The method of claim 1, wherein the method further includes identifying different types of breast shapes, including at least one of a natural breast, a surgically altered breast, an autologous breast, or an implant reconstructed breast, or a combination of autologous and implant breasts, based on SPHARM coefficients.

4. The method of claim 1, wherein the 3D image is a patient's preoperative image; and
    the method further includes:
        predicting a post-operative breast shape from the 3D image based on the 3D SPHARM descriptor; and
        outputting a predicted 3D image based on the predicted post-operative breast shape.

5. The method of claim 4, wherein the predicting includes:
    searching a database for a 3D image of at least one second patient with similar demographics or medical history to the patient of the received 3D image, wherein the database includes pre-operative and post-operative 3D images;
    determining SPHARM coefficients of the received 3D image;
    locating a pre-operative 3D image of at least one second patient with at least one of a similar age, breast size, or breast shape based on the SPHARM coefficients;
    locating a post-operative 3D image of the at least one second patient;
    generating an average pre-operative 3D image based on the pre-operative 3D images;
    generating an average post-operative 3D image based on the post-operative 3D images;
    determining SPHARM coefficients of at least one of an average pre-operative 3D image or a located post-operative 3D image;
    determining SPHARM coefficients of at least one of an average post-operative 3D image or a located post-operative 3D image;
    determining a difference between SPHARM coefficients of the received 3D image or the average pre-operative image and SPHARM coefficients of the average post-operative 3D image;
    applying the difference in SPHARM coefficients to the received 3D image; and
    morphing the breast of the received 3D image based on the determined SPHARM coefficients.

6. The method of claim 4, wherein the predicting includes:
    identifying, in a database, a post-op 3D image of at least one second patient with similar demographics or medical history, or breast shape to the patient of the received 3D image, wherein the database includes post-operative 3D images of breasts;
    generating a template post-operative 3D image based on the identified post-operative images to represent a particular outcome;
    determining SPHARM coefficients of the received 3D image and SPHARM coefficients of the template;
    determining a difference between the SPHARM coefficients of the received 3D image and the SPHARM coefficients of the template;
    applying the difference in SPHARM coefficients to the received 3D image; and
    morphing the breast of the received 3D image based on the determined SPHARM coefficients.

7. The method of claim 4, wherein the predicting includes using a machine learning algorithm, where training data inputs include at least one of pre operation image data, pre operation model data, post operation image data, post operation model data, or patient demographic data.

8. The method of claim 7, wherein the machine learning algorithm includes at least one of a neural network, random forest regression, linear regression (LR), ridge regression (RR), least-angle regression (LARS), or least absolute shrinkage and selection operator regression (LASSO).

9. The method of claim 4, wherein the method includes identifying different types of breast shapes based on position including at least one of upright, supine prone, or any position there between, generating position specific templates, and
wherein the outputting is based on patient position including at least one of upright, supine, prone, or any position there between.

10. The method of claim 9, wherein the different types of breast shapes include at least one of natural, unnatural, surgically altered, or aged.

11. The method of claim 1, wherein the forming of a closed object includes:
identifying holes in a first mesh by finding boundary edges, which are edges that are not shared by two faces;
calculating an angle between adjacent boundary edges at a vertex;
locating the smallest angle and creating a new triangle at the vertex;
creating a second mesh to substantially fill the identified holes, wherein a location of a second vertex is determined by an average edge length and a shortest direction to close a gap across the two meshes;
computing a distance between every newly created vertex and every related boundary vertex, in a case where the distance between them is less than a predetermined threshold they are merged; and
updating the second mesh based on the computed distance.

12. The method of claim 1, wherein the method further includes identifying different types of breast shapes, including at least one of natural breast shape, cosmetically altered breast shape, surgically reconstructed breast shape, reduction mammoplasty, reduction mastopexy, augmentation mammoplasty, augmentation mastopexy, or correction of any breast shape deformities, based on spherical harmonic coefficients.

13. A system for modeling a breast shape, the system comprising:
a processor; and
a memory, including instructions, which when executed by the processor, cause the system to:
receive a 3D image including a breast;
identify the breast in the 3D image;
extract 3D image data of the breast from the 3D image;
form a closed object using the 3D image data of the breast to create a zero-genus surface;
map the 3D image data of the breast to a predefined template using spherical coordinates; and
determine a 3D spherical harmonic (SPHARM) descriptor of the 3D image data of the breast.

14. The system of claim 13, wherein the instructions, when executed, further cause the system to identify parameters of the 3D spherical harmonic descriptor that represent anatomical breast parameters including at least one of a height, a width, a depth, or ptosis.

15. The system of claim 13, wherein the instructions, when executed, further cause the system to identify different types of breast shapes, including at least one of autologous or implant reconstructed breast or a combination of autologous and implant breasts, based on SPHARM coefficients.

16. The system of claim 13, wherein the 3D image is a patient's preoperative image; and
wherein the instructions, when executed, further cause the system to:
predict a post-operative breast shape from the 3D image based on the 3D SPHARM model; and
output a predicted 3D image based on the predicted post-operative breast shape.

17. The system of claim 16, wherein when predicting, the instructions, when executed, further cause the system to:
search a database for a 3D image of at least one second patient with similar demographics or medical history to the patient of the received 3D image, wherein the database includes pre-operative and post-operative 3D images;
determine SPHARM coefficients of the received 3D image;
locate a pre-operative 3D image of at least one second patient with at least one of a similar age, breast size, or breast shape based on the SPHARM coefficients;
locate a post-operative 3D image of the at least one second patient;
generate an average pre-operative 3D image based on the pre-operative 3D images;
generate an average post-operative 3D image based on the post-operative 3D images;
determine SPHARM coefficients of at least one of the average pre-operative 3D image determine SPHARM coefficients of at least one of the average post-operative 3D image or a located post-operative 3D image;
determine a difference between SPHARM coefficients of the received 3D image or the average pre-operative image and SPHARM coefficients of the average post-operative 3D image;
apply the difference in SPHARM coefficients to the received 3D image; and
morph the breast of the received 3D image based on the determined SPHARM coefficients.

18. The system of claim 16, wherein when predicting, the instructions, when executed, further cause the system to:
identify, in a database, a post-op 3D image of at least one second patient with similar demographics or medical history, or breast shape to the patient of the received 3D image, wherein the database includes post-operative 3D images of breasts;
generate a template post-operative 3D image based on the identified post-operative images to represent a particular outcome;
determine SPHARM coefficients of the received 3D image and the SPHARM coefficients of the template;
determine a difference between the SPHARM coefficients of the received 3D image and the SPHARM coefficients of the template;
apply the difference in SPHARM coefficients to the received 3D image; and
morph the breast of the received 3D image based on the determined SPHARM coefficients.

19. The system of claim 16, wherein the predicting includes using a machine learning algorithm, where training data inputs include at least one of pre and post operation image data or patient demographic data, wherein the machine learning algorithm includes at least one of a neural network, random forest regression, linear regression (LR), ridge regression (RR), least-angle regression (LARS), or least absolute shrinkage and selection operator regression (LASSO).

20. A non-transitory storage medium that stores a program causing a computer to execute a method for modeling a breast shape, the method comprising:
- receiving a 3D image including a breast;
- identifying the breast in the 3D image;
- extracting 3D image data of the breast from the 3D image;
- forming a closed object using the 3D image data of the breast to create a zero-genus surface;
- mapping the 3D image data of the breast to a predefined template using spherical coordinates; and
- determining a 3D spherical harmonic (SPHARM) descriptor of the 3D image data of the breast.

* * * * *